US008697842B2

(12) United States Patent
Dhugga et al.

(10) Patent No.: US 8,697,842 B2

(45) Date of Patent: Apr. 15, 2014

(54) MAIZE CELLULOSE SYNTHASES AND USES THEREOF

(71) Applicant: Pioneer Hi Bred International Inc, Johnston, IA (US)

(72) Inventors: Kanwarpal Singh Dhugga, Johnston, IA (US); Haiyin Wang, Johnston, IA (US); Dwight Tomes, Grimes, IA (US); Timothy George Helentjaris, Tucson, AZ (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/887,430

(22) Filed: May 6, 2013

(65) Prior Publication Data

US 2013/0230900 A1 Sep. 5, 2013

Related U.S. Application Data

(60) Continuation of application No. 13/459,370, filed on Apr. 30, 2012, now Pat. No. 8,481,682, which is a continuation of application No. 13/079,071, filed on Apr. 4, 2011, now Pat. No. 8,207,302, which is a division of application No. 12/903,472, filed on Oct. 13, 2010, now Pat. No. 7,982,009, which is a division of application No. 12/782,738, filed on May 19, 2010, now Pat. No. 7,838,632, which is a division of application No. 12/486,129, filed on Jun. 17, 2009, now Pat. No. 7,851,597, which is a division of application No. 12/277,418, filed on Nov. 25, 2008, now Pat. No. 7,579,443, which is a division of application No. 11/859,968, filed on Sep. 24, 2007, now Pat. No. 7,524,933, which is a division of application No. 10/963,217, filed on Oct. 12, 2004, now Pat. No. 7,307,149, which is a continuation-in-part of application No. 10/209,059, filed on Jul. 31, 2002, now Pat. No. 6,930,225, which is a continuation-in-part of application No. 09/550,483, filed on Apr. 14, 2000, now abandoned, which is a continuation-in-part of application No. 09/371,383, filed on Aug. 6, 1999, now abandoned.

(60) Provisional application No. 60/096,822, filed on Aug. 17, 1998.

(51) Int. Cl.

| | |
|---|---|
| ***C07K 4/10*** | (2006.01) |
| ***C07K 17/12*** | (2006.01) |
| ***C12N 15/09*** | (2006.01) |

(52) U.S. Cl.

USPC .......................... 530/372; 530/350; 435/69.1

(58) Field of Classification Search

None

See application file for complete search history.

(56) References Cited

U.S. PATENT DOCUMENTS 5,723,764 A 3/1998 Nichols

FOREIGN PATENT DOCUMENTS

| | | |
|---|---|---|
| WO | 9800546 A1 | 1/1998 |
| WO | 9818949 A2 | 5/1998 |
| WO | 0004166 A2 | 1/2000 |
| WO | 0009706 A2 | 2/2000 |

OTHER PUBLICATIONS

Amor, Y., et al.; "A membrane-associated form of sucrose and its potential role in synthesis of cellulose and callose in plants"; PNAS (Sep. 1995) 92:9353-9357; National Academy of Sciences; Washington, DC US.

AC 048947 "*A. thaliana* cellulose synthase catalytic subunit EMBL database entry" (Jun. 1998).

AF 027174 "*A. thaliana* cellulose synthase catalytic subunit EMBL/GeneBank/DDBJ database entry" (Feb. 1999).

Amor, Y., et al.; "Evidence for a cyclic diguanylic acid-dependent cellulose synthase in plants"; Plant Cell (1991) 3(9)898-995; American Society of plant Physiologists; Rockville, MD, US.

Arioli, et al.; "Accession No. AC048946 Molecular Analysis of Cellulose Biosynthesis in *Arabidopsis*"; Science (1998) 279:717-720 (XP-002140499); American Association for the Advancement of Science; Washington, DC US.

Arioli, et al.; "Accession No. AF027173 Molecular Analysis of Cellulose Biosynthesis in *Arabidopsis*" Science (1998) 279:717-720 (XP-002140700); American Association for the Advancement of Science; Washington, DC US.

Arioli, et al.; "Accession No. AF030052 Molecular Analysis of Cellulose Biosynthesis in *Arabidopsis*" Science (1998) 279:717-720 (XP-002140698); American Association for the Advancement of Science; Washington, DC US.

Arioli, et al.; "Accession No. AC048948 Molecular Analysis of Cellulose Biosynthesis in *Arabidopsis*" Science (1998) 279:717-720 (XP-002140697); American Association for the Advancement of Science; Washington, DC US.

Arioli, T., et al.; "Molecular Analysis of Celluose Biosynthesis in *Arabidopsis*" Science (Jan. 1998) 279:717-720; American Association for the Advancement of Science; Washington, DC, US.

Delmer, D.; "Cellulose Biosynthesis: Exciting Times for a Difficult Field of Study" Ann Rev Plant Physiol Plant Mol Bio (1999) 50:245-276; Springer, The Netherlands.

(Continued)

*Primary Examiner* — Medina A Ibrahim

(74) *Attorney, Agent, or Firm* — Pioneer Hi-Bred International

(57) ABSTRACT

The invention provides isolated cellulose synthase nucleic acids and their encoded proteins. The present invention provides methods and compositions relating to altering cellulose synthase levels in plants. The invention further provides recombinant expression cassettes, host cells, and transgenic plants comprising cellulose synthase nucleic acids. The invention provides isolated products from the processing of transgenic plants comprising cellulose synthase nucleic acids.

7 Claims, 9 Drawing Sheets

(56) References Cited

OTHER PUBLICATIONS

Haigler, C., et al.; "New hope for old dreams: Evidence that plant cellulose synthesis genes have finally been identified"; PNAS (Oct. 1996) 93:12082-12085; National Academy of Sciences; Washington, DC.

Holland, et al.; "A comparative analysis of the plant cellulose synthase (CesA) gene family"; Plant Physiology (Aug. 2000) 123:113-1323; American Society of Plant Biologists; Rockville, MD, US.

Holland, et al.; "Accession No. AF200527, A comparative analysis of the plant cellulose synthase (CesA) gene family"; Plant Physiology (Aug. 2000) 123:113-1323; American Society of Plant Biologists; Rockville, MD, US.

Holland, et al.; "Accession No. AF200533, A comparative analysis of the plant cellulose synthase (CesA) gene family"; Plant Physiology (Aug. 2000) 123:113-1323; American Society of Plant Biologists; Rockville, MD, US.

Holland, et al.,; "Accession No. Q9LLI1, A comparative analysis of the plant cellulose synthase (CesA) gene family"; Plant Physiology (Aug. 2000) 123:113-1323; American Society of Plant Biologists; Rockville, MD, US.

Holland, et al.,; "Accession No. Q9LLI7, A comparative analysis of the plant cellulose synthase (CesA) gene family"; Plant Physiology (Aug. 2000) 123:113-1323; American Society of Plant Biologists; Rockville, MD, US.

Pear, J.R., et al.; "Higher plants contain homologs of the bacterial CelA genes encoding the catalytic subunit of cellulose synthase"; PNAS (Oct. 1996) 93:12637-12642; National Academy of Sciences; Washington, DC.

Wu, et al.; "Accession No. AC065338" (1998) (XP-002140701).

MAIZE CELLULOSE SYNTHASES AND USES THEREOF

RELATED APPLICATIONS

This application is a continuation of U.S. patent application Ser. No. 13/459,370 filed Apr. 30, 2013, now issued as U.S. Pat. No. 8,481,682, which is a continuation of U.S. patent application Ser. No. 13/079,071 filed Apr. 4, 2011, now issued as U.S. Pat. No. 8,207,302, which is a divisional of Ser. No. 12/903,472 filed Oct. 13, 2010, now issued as U.S. Pat. No. 7,982,009, which is a divisional of Ser. No. 12/782,738 filed May 19, 2010, now issued as U.S. Pat. No. 7,838,632, which is a divisional of Ser. No. 12/486,129 filed Jun. 17, 2009, now issued as U.S. Pat. No. 7,851,597, which is a divisional of U.S. patent application Ser. No. 12/277,418 filed Nov. 25, 2008, now issued as U.S. Pat. No. 7,579,443, which is a divisional of U.S. patent application Ser. No. 11/859,968 filed Sep. 24, 2007, now issued as U.S. Pat. No. 7,524,933, which is a divisional of U.S. patent application Ser. No. 10/963,217 filed Oct. 12, 2004, now issued as U.S. Pat. No. 7,307,149, which is a continuation-in-part of U.S. patent application Ser. No. 10/209,059, filed Jul. 31, 2002, now issued as U.S. Pat. No. 6,930,225, which is a continuation-in-part of U.S. patent application Ser. No. 09/550,483, filed Apr. 14, 2000, now abandoned, which is a continuation-in-part of U.S. patent application Ser. No. 09/371,383, filed Aug. 6,1999, now abandoned, which claims benefit of U.S. Provisional Patent Application Ser. No. 60/096,822, filed Aug. 17,1998, all of which are incorporated herein by reference. Also incorporated by reference are U.S. patent application Ser. No. 11/493,187, filed Jul. 26, 2006, now issued as U.S. Pat. No. 7,312,377 and U.S. patent application Ser. No. 10/961,254 filed Oct. 8, 2004, now issued as U.S. Pat. No.7, 214,852, U.S. patent application Ser. No. 10/160,719, filed Jun. 3, 2002, now issued as U.S. Pat. No. 6,803,498, which is a continuation of U.S. patent application Ser. No. 09/371,383, filed Aug. 6, 1999, now abandoned, which claims benefit of U.S. Provisional Patent Application Ser. No. 60/096,822, filed Aug. 17, 1998, now abandoned.

TECHNICAL FIELD

The present invention relates generally to plant molecular biology. More specifically, it relates to nucleic acids and methods for modulating their expression in plants.

BACKGROUND OF THE INVENTION

Polysaccharides constitute the bulk of the plant cell walls and have been traditionally classified into three categories: cellulose, hemicellulose and pectin. Fry, (1988) The growing plant cell wall: Chemical and metabolic analysis, New York: Longman Scientific & Technical. Whereas cellulose is made at the plasma membrane and directly laid down into the cell wall, hemicellulosic and pectic polymers are first made in the Golgi apparatus and then exported to the cell wall by exocytosis. Ray, et al., (1976) *Ber. Deutsch. Bot. Ges. Bd.* 89:121-146. The variety of chemical linkages in the pectic and hemicellulosic polysaccharides indicates that there must be tens of polysaccharide synthases in the Golgi apparatus. Darvill, et al., (1980) The primary cell walls of flowering plants. In The Plant Cell (NE Tolbert, ed.), Vol. 1 in Series: The biochemistry of plants: A comprehensive treatise, eds. Stumpf and Conn, (New York: Academic Press), pp. 91-162.

Even though sugar and polysaccharide compositions of the plant cell walls have been well characterized, very limited progress has been made toward identification of the enzymes involved in polysaccharides formation, the reason being their labile nature and recalcitrance to solubilization by available detergents. Sporadic claims for the identification of cellulose synthase from plant sources were made over the years. Callaghan and Benziman, (1984) *Nature* 311:165-167; Okuda, et al., (1993) *Plant Physiol.* 101:1131-1142. However, these claims were met with skepticism. Callaghan and Benziman, (1985), *Nature* 314:383-384; Delmer, et al., (1993) *Plant Physiol.* 103:307-308. It was only relatively recently that a putative gene for plant cellulose synthase (CesA) was cloned from the developing cotton fibers based on homology to the bacterial gene. Pear, et al., *Proc. Natl. Acad. Sci. USA* 93:12637-12642; Saxena, et al., (1990) *Plant Molecular Biology* 15:673-684; see also, WO 1998/18949; see also, Arioli, et al., (1998). Molecular analysis of cellulose biosynthesis in *Arabidopsis. Science* Washington, D.C. January 279:717-720. A number of genes for cellulose synthase family were later isolated from other plant species based on sequence homology to the cotton gene (Richmond and Somerville, (2000) *Plant Physiology* 124:495-498.)

Cellulose, by virtue of its ability to form semicrystalline microfibrils, has a very high tensile strength which approaches that of some metals. Niklas, (1992), Plant Biomechanics: An engineering approach to plant form and function, The University of Chicago Press, p. 607. Bending strength of the culm of normal and brittle-culm mutants of barley has been found to be directly correlated with the concentration of cellulose in the cell wall. Kokubo, et al., (1989), *Plant Physiology* 91:876-882; Kokubo, et al., (1991) *Plant Physiology* 97:509-514.

Although stalk composition contributes to numerous quality factors important in maize breeding, little is known in the art about the impact of cellulose levels on such agronomically important traits as stalk lodging, silage digestibility or downstream processing. The present invention provides these and other advantages.

SUMMARY OF THE INVENTION

Generally, it is the object of the present invention to provide nucleic acids and proteins relating to cellulose synthases. It is an object of the present invention to provide transgenic plants comprising the nucleic acids of the present invention and methods for modulating, in a transgenic plant, expression of the nucleic acids of the present invention.

Therefore, in one aspect the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a) and (c) a polynucleotide comprising a specified number of contiguous nucleotides from a polynucleotide of (a) or (b). The isolated nucleic acid can be DNA.

In other aspects the present invention relates to: 1) recombinant expression cassettes, comprising a nucleic acid of the present invention operably linked to a promoter, 2) a host cell into which has been introduced the recombinant expression cassette, 3) a transgenic plant comprising the recombinant expression cassette and 4) a transgenic plant comprising a recombinant expression cassette containing more than one nucleic acid of the present invention each operably linked to a promoter. Furthermore, the present invention also relates to combining by crossing and hybridization recombinant cassettes from different transformants. The host cell and plant are optionally from maize, wheat, rice or soybean.

In other aspects the present invention relates to methods of altering stalk lodging and other standability traits, including, but not limited to brittle snap and improving stalk digestibility, through the introduction of one or more of the polynucleotides that encode the polypeptides of the present invention. Additional aspects of the present invention include methods and transgenic plants useful in the end use processing of compounds such ads cellulose or use of transgenic plants as end products either directly, such as silage, or indirectly following processing, for such uses known to those of skill in the art, such as, but not limited to, ethanol. Also, one of skill in the art would recognize that the polynucleotides and encoded polypeptides of the present invention can be introduced into an host cell or transgenic plant wither singly or in multiples, sometimes referred to in the art as "stacking" of sequences or traits. It is intended that these compositions and methods be encompassed in the present invention.

DETAILED DESCRIPTION OF THE INVENTION

Overview

A. Nucleic Acids and Protein of the Present Invention

Unless otherwise stated, the polynucleotide and polypeptide sequences identified in Table 1 represent polynucleotides and polypeptides of the present invention. Table 1 cross-references these polynucleotide and polypeptides to their gene name and internal database identification number (SEQ ID NO.). A nucleic acid of the present invention comprises a polynucleotide of the present invention. A protein of the present invention comprises a polypeptide of the present invention.

TABLE 1

| Gene Name | Database ID NO: | Polynucleotide SEQ ID NO: | Polypeptide SEQ ID NO: |
|---|---|---|---|
| Cellulose synthase | CesA-1 | 1 | 2 |
| Cellulose synthase | CesA-2 | 45 | 46 |
| Cellulose synthase | CesA-3 | 5 | 6 |
| Cellulose synthase | CesA-4 | 9 | 10 |
| Cellulose synthase | CesA-5 | 13 | 14 |
| Cellulose synthase | CesA-6 | 41 | 42 |
| Cellulose synthase | CesA-7 | 49 | 50 |
| Cellulose synthase | CesA-8 | 17 | 18 |
| Cellulose synthase | CesA-9 | 21 | 22 |
| Cellulose synthase | CesA-10 | 25 | 26 |
| Cellulose synthase | CesA-11 | 27 | 28 |
| Cellulose synthase | CesA-12 | 29 | 30 |

Table 2 further provides a comparison detailing the homology as a percentage of the 12 CesA genes from maize that have been described herein (see, also, "Related Applications" above).

TABLE 2

| | CesA1 | CesA2 | CesA3 | CesA4 | CesA5 | CesA6 | CesA7 | CesA8 | CesA9 | CesA10 | CesA11 | CesA12 |
|---|---|---|---|---|---|---|---|---|---|---|---|---|
| CesA1 | | 93 | 60 | 59 | 60 | 55 | 55 | 57 | 61 | 51 | 51 | 46 |
| CesA2 | | | 60 | 59 | 61 | 55 | 55 | 57 | 61 | 51 | 51 | 47 |
| CesA3 | | | | 47 | 48 | 49 | 45 | 46 | 49 | 46 | 52 | 50 |
| CesA4 | | | | | 77 | 54 | 52 | 58 | 86 | 54 | 53 | 52 |
| CesA5 | | | | | | 55 | 53 | 57 | 75 | 52 | 52 | 51 |
| CesA6 | | | | | | | 74 | 73 | 56 | 56 | 55 | 53 |

TABLE 2-continued

| | CesA1 | CesA2 | CesA3 | CesA4 | CesA5 | CesA6 | CesA7 | CesA8 | CesA9 | CesA10 | CesA11 | CesA12 |
|---|---|---|---|---|---|---|---|---|---|---|---|---|
| CesA7 | | | | | | | | 70 | 54 | 50 | 48 | 46 |
| CesA8 | | | | | | | | | 59 | 55 | 52 | 51 |
| CesA9 | | | | | | | | | | 52 | 52 | 50 |
| CesA10 | | | | | | | | | | | 53 | 64 |
| CesA11 | | | | | | | | | | | | 56 |
| CesA12 | | | | | | | | | | | | |

Figure 4:
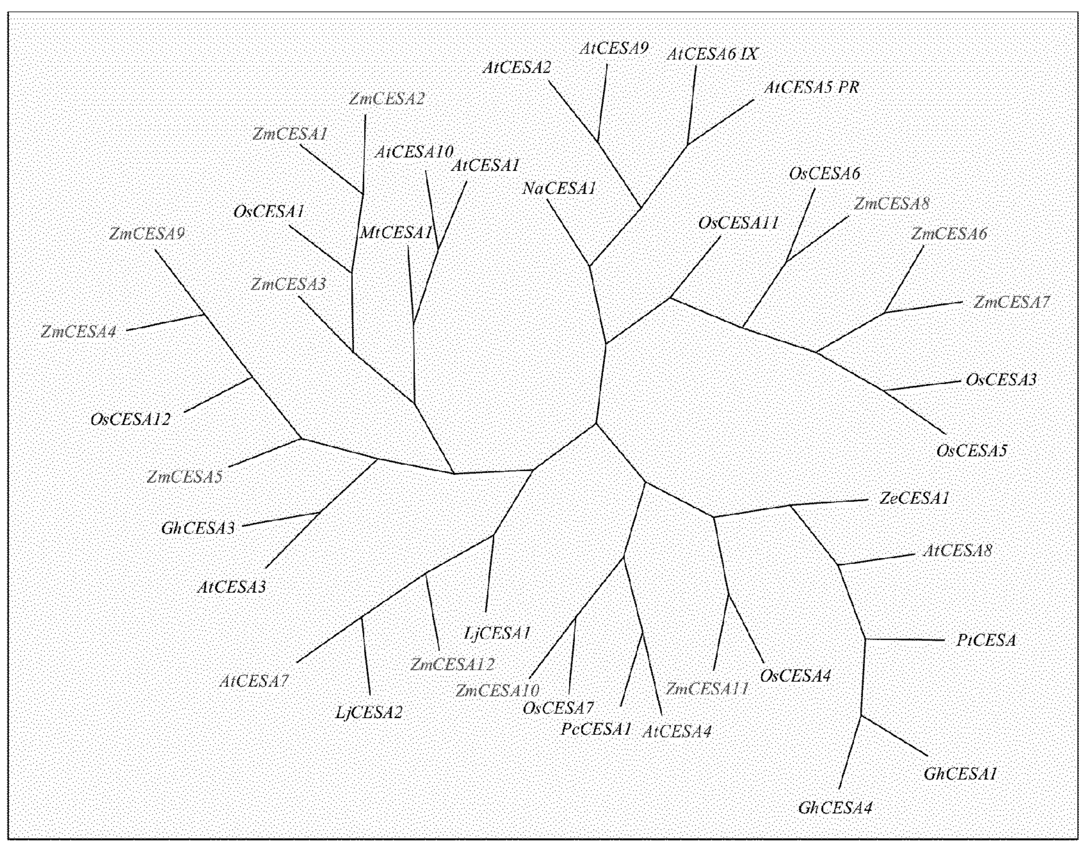
FIG. 4: Unrooted cladogram of CesA proteins from different species. Sequences are labeled by prefixes. This cladogram demonstrates the relevance of the maize genes to those of *Arabidopsis* and rice. Prefixes: At, *Arabidopsis thaliana*; Gh, *Gossypium herbaceum*; Lj, *Lotus japonicus*; Mt, *Medicago truncatula*; Na, *Nicotiana alata*; Os, *Oriza sativa*; Pc, *Populus canescens*; Ptr, *Populus tremula×tremuloides*; Ze, *Zinnia elegans*; Zm, *Zea mays.*

Further characterization of the CesA group is provided in FIG. 4, as a consensus tree for plant Ces A proteins. It describes the relationship between Ces A from maize, rice and *Arabidopsis* sources.

B. Exemplary Utility of the Present Invention

The present invention provides utility in such exemplary applications as improvement of stalk quality for improved stand lodging or standability or silage digestibility. Further, the present invention provides for an increased concentration of cellulose in the pericarp, hardening the kernel and thus improving its handling ability. Stalk lodging at maturity can cause significant yield losses in corn. Environmental stresses from flowering to harvest, such as drought and nutrient deficiency, further worsen this problem. The effect of abiotic stresses is exacerbated by biotic factors, such as stalk rot resulting from the soil-living pathogens growing through the ground tissue.

Maize hybrids known to be resistant to stalk lodging have mechanically stronger stalks. At the compositional level, cellulose in a unit stalk length is highly correlated with breaking strength. The present invention provides for modulation of cellulose synthase composition leading to increased stalk strength.

Definitions

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise provided for, software, electrical and electronics terms as used herein are as defined in The New IEEE Standard Dictionary of Electrical and Electronics Terms (5th edition, 1993). The terms defined below are more fully defined by reference to the specification as a whole. Section headings provided throughout the specification are not limitations to the various objects and embodiments of the present invention.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., *Diagnostic Molecular Microbiology Principles and Applications*, Persing, et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal and fungal mitochondria, the bacterium *Mycoplasma capricolumn* or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17:477-498). Thus, the maize preferred codon for a particular amino acid may be derived from known gene sequences from maize. Maize codon usage for 28 genes from maize plants is listed in Table 4 of Murray, et al., supra.

As used herein "full-length sequence" in reference to a specified polynucleotide or its encoded protein means having the entire amino acid sequence of a native (non-synthetic), endogenous, biologically (e.g., structurally or catalytically) active form of the specified protein. Methods to determine whether a sequence is full-length are well known in the art, including such exemplary techniques as northern or western blots, primer extension, S1 protection and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by human intervention.

By "host cell" is meant a cell which contains a vector and supports the replication and/or expression of the vector. Host cells may be prokaryotic cells such as *E. coli*, or eukaryotic cells such as yeast, insect, amphibian or mammalian cells. Preferably, host cells are monocotyledonous or dicotyledonous plant cells. A particularly preferred monocotyledonous host cell is a maize host cell.

The term "introduced" includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection", "transformation" and "transduction".

The term "isolated" refers to material, such as a nucleic acid or a protein, which is: (1) substantially or essentially free from components which normally accompany or interact with it as found in its natural environment. The isolated material optionally comprises material not found with the material in its natural environment or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells, Zarling, et al., WO 1993/22443 (PCT/US93/03868).

As used herein, "nucleic acid" includes reference to a deoxyribonucleotide or ribonucleotide polymer or chimeras thereof in either single- or double-stranded form and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism, tissue or of a cell type from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook, et al., *Molecular Cloning—A Laboratory Manual*, 2$^{nd}$ ed., Vol. 1-3 (1989) and *Current Protocols in Molecular Biology*, Ausubel, et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide or chimeras or analogs thereof that have the essential nature of a natural deoxy- or ribo-nucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gammacarboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses and bacteria which comprise genes expressed in plant cells such *Agrobacterium* or *Rhizobium*. Examples of promoters under developmental control include promoters that preferentially initiate transcription in certain tissues, such as leaves, roots or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of human intervention. The term "recombinant" as used herein does not encompass the alteration of the cell or vector by naturally occurring events (e.g., spontaneous mutation, natural transformation/transduction/transposition) such as those occurring without human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The terms "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity and most preferably 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ("$T_m$") for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120 or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity" and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100 or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA and TFASTA in the Wisconsin Genetics Software Package®, Genetics Computer Group (GCG®), 575 Science Dr., Madison, Wis., USA; the CLUSTAL program is well described by Higgins and Sharp, (1988) *Gene* 73:237-244; Higgins and Sharp, (1989) *CABIOS* 5:151-153; Corpet, et al., (1988) Nucleic Acids Research 16:10881-90; Huang, et al., (1992) *Computer Applications in the Biosciences* 8:155-65 and Pearson, et al., (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology, Chapter* 19, Ausubel, et al., Eds., Greene Publishing and Wiley-Interscience, New York (1995); Altschul, et al., (1990) *J. Mol. Biol.,* 215:403-410 and Altschul, et al., (1997) *Nucleic Acids Res.* 25:3389-3402.

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff and Henikoff, (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-163) and XNU (Claverie and States, (1993) *Comput. Chem* 17:191-201) low-complexity filters can be employed alone or in combination.

Unless otherwise stated, nucleotide and protein identity/similarity values provided herein are calculated using GAP (GCG® Version 10) under default values.

GAP (Global Alignment Program) can also be used to compare a polynucleotide or polypeptide of the present invention with a reference sequence. GAP uses the algorithm of Needleman and Wunsch, (*J. Mol. Biol.* 48: 443-453 (1970)) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Multiple alignment of the sequences can be performed using the CLUSTAL method of alignment (Higgins and Sharp, (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17 e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Utilities

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues and/or in quantities, which are uncharacteristic of non-recombinantly engineered plants.

The present invention also provides isolated nucleic acids comprising polynucleotides of sufficient length and complementarity to a polynucleotide of the present invention to use as probes or amplification primers in the detection, quantitation or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions or additions), for monitoring upregulation of expression or changes in enzyme activity in screening assays of compounds, for detection of any number of allelic variants (polymorphisms), orthologs or paralogs of the gene or for site directed mutagenesis in eukaryotic cells (see, e.g., U.S. Pat. No. 5,565,350). The isolated nucleic acids of the present invention can also be used for recombinant expression of their encoded polypeptides or for use as immunogens in the preparation and/or screening of antibodies. The isolated nucleic acids of the present invention can also be employed for use in sense or antisense suppression of one or more genes of the present invention in a host cell, tissue or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme or enzymes). The present invention also provides proteins comprising at least one epitope from a polypeptide of the present invention. The proteins of the present invention can be employed in assays for enzyme agonists or antagonists of enzyme function or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species or for purification of polypeptides of the present invention.

The isolated nucleic acids and polypeptides of the present invention can be used over a broad range of plant types, particularly monocots such as the species of the family *Gramineae* including *Hordeum, Secale, Oryza, Triticum, Sorghum* (e.g., *S. bicolor*) and *Zea* (e.g., *Z. mays*) and dicots such as *Glycine.*

The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Pisum, Phaseolus, Lolium* and *Avena.*

Nucleic Acids

The present invention provides, among other things, isolated nucleic acids of RNA, DNA and analogs and/or chimeras thereof, comprising a polynucleotide of the present invention.

A polynucleotide of the present invention is inclusive of those in Table 1 and:

(a) an isolated polynucleotide encoding a polypeptide of the present invention such as those referenced in Table 1, including exemplary polynucleotides of the present invention;

(b) an isolated polynucleotide which is the product of amplification from a plant nucleic acid library using primer pairs which selectively hybridize under stringent conditions to loci within a polynucleotide of the present invention;

(c) an isolated polynucleotide which selectively hybridizes to a polynucleotide of (a) or (b);

(d) an isolated polynucleotide having a specified sequence identity with polynucleotides of (a), (b) or (c);

(e) an isolated polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d) or (e);

(g) an isolated polynucleotide comprising at least a specific number of contiguous nucleotides from a polynucleotide of (a), (b), (c), (d), (e) or (f);

(h) an isolated polynucleotide from a full-length enriched cDNA library having the physico-chemical property of selectively hybridizing to a polynucleotide of (a), (b), (c), (d), (e), (f) or (g);

(i) an isolated polynucleotide made by the process of: 1) providing a full-length enriched nucleic acid library, 2) selectively hybridizing the polynucleotide to a polynucleotide of (a), (b), (c), (d), (e), (f), (g) or (h), thereby isolating the polynucleotide from the nucleic acid library.

A. Polynucleotides Encoding a Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include maize, sorghum, alfalfa, canola, wheat or rice. The plant nucleic acid library can also be constructed from a dicot such as soybean. *Zea mays* lines B73, PHRE1, A632, BMS-P2#10, W23 and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama and Sugano, (1994) *Gene* 138:171-174), Biotinylated CAP Trapper (Carninci, et al., (1996) *Genomics* 37:327-336) and CAP Retention Procedure (Edery, et al., (1995) *Molecular and Cellular Biology* 15:3363-3371). Rapidly growing tissues or rapidly dividing cells are preferred for use as an mRNA source for construction of a cDNA library. Growth stages of maize are described in "How a Corn Plant Develops," Special Report Number 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention or to two sites within the nucleic acid which flank and comprise a polynucleotide of the present invention or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, in PCR Protocols: A Guide to Methods and Applications, Innis, et al., Eds. (Academic Press, Inc., San Diego), pp. 28-38 (1990)); see, also, U.S. Pat. No. 5,470,722 and *Current Protocols in Molecular Biology*, Unit 15.6, Ausubel, et al., Eds., Greene Publishing and Wiley-Interscience, New York (1995); Frohman and Martin, *Techniques* 1:165 (1989).

Optionally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40 or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity) or verifying the presence of one or more epitopes which are specific to a polypeptide of the present invention. Methods for protein synthesis from PCR derived templates are known in the art and available commercially. See, e.g., Amersham Life Sciences, Inc, Catalog '97, p. 354.

C. Polynucleotides which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting and/or quantifying nucleic acids comprising the polynucleotides of (A) or (B). For example, polynucleotides of the present invention can be used to identify, isolate or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley and rice. The cDNA library comprises at least 50% to 95% full-length sequences (for example, at least 50%, 60%, 70%, 80%, 90% or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B) or (C), above. Identity can be calculated using, for example, the BLAST, CLUSTALW or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 60%, 70%, 75%, 80%, 85%, 90% or 95%.

Optionally, the polynucleotides of this embodiment will encode a polypeptide that will share an epitope with a polypeptide encoded by the polynucleotides of sections (A), (B) or (C). Thus, these polynucleotides encode a first polypeptide which elicits production of antisera comprising antibodies which are specifically reactive to a second polypeptide encoded by a polynucleotide of (A), (B) or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B) or (C), or for purification of, or in immunoassays for, polypeptides encoded by the polynucleotides of (A), (B) or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Numbers 1991/17271, 1991/18980, 1991/19818 and 1993/08278. Other systems for generating libraries of peptides have aspects of both in vitro chemical synthesis and recombinant methods. See, PCT Patent Publication Numbers 1992/05258, 1992/14843 and 1997/20078. See also, U.S. Pat. Nos. 5,658,754 and 5,643,768. Peptide display libraries, vectors and screening kits are commercially available from such suppliers as Invitrogen (Carlsbad, Calif.).

E. Polynucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45 or 50, contiguous amino acids from the prototype polypeptide. Further, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2% or 1% of a full length polypeptide of the present invention.

Optionally, the polynucleotides of this embodiment will encode a protein having a specific enzymatic activity at least 50%, 60%, 80% or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50% and most preferably at least 60%, 70%, 80%, 90% or 95% the $k_{cat}/K_m$ value of the full-length polypeptide of the present invention. Determination of $k_{cat}$, $K_m$ and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow or rapid quenching techniques), flash photolysis or relaxation methods (e.g., temperature jumps) in conjunction with such exemplary methods of measuring as spectrophotometry, spectrofluorimetry, nuclear magnetic resonance or radioactive procedures. Kinetic values are conveniently obtained using a Lineweaver-Burk or Eadie-Hofstee plot.

F. Polynucleotides Complementary to the Polynucleotides of (A)-(E)

As indicated in (f), above, the present invention provides isolated nucleic acids comprising polynucleotides complementary to the polynucleotides of paragraphs A-E, above. As those of skill in the art will recognize, complementary sequences base-pair throughout the entirety of their length with the polynucleotides of sections (A)-(E) (i.e., have 100% sequence identity over their entire length). Complementary bases associate through hydrogen bonding in double stranded nucleic acids. For example, the following base pairs are complementary: guanine and cytosine; adenine and thymine and adenine and uracil.

G. Polynucleotides which are Subsequences of the Polynucleotides of (A)-(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75 or 100 contiguous nucleotides in length from the polynucleotides of (A)-(F). Optionally, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

Subsequences can be made by in vitro synthetic, in vitro biosynthetic or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides from a Full-Length Enriched cDNA Library Having the Physico-Chemical Property of Selectively Hybridizing to a Polynucleotide of (A)-(G)

As indicated in (h), above, the present invention provides an isolated polynucleotide from a full-length enriched cDNA library having the physico-chemical property of selectively hybridizing to a polynucleotide of paragraphs (A), (B), (C), (D), (E), (F) or (G) as discussed above. Methods of constructing full-length enriched cDNA libraries are known in the art and discussed briefly below. The cDNA library comprises at least 50% to 95% full-length sequences (for example, at least 50%, 60%, 70%, 80%, 90% or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95% or 98% sequence identity over the length of the hybridized region. Full-length enriched cDNA libraries can be normalized to increase the representation of rare sequences.

I Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G) or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art. Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)-(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis and the like.

Construction of Nucleic Acids

The isolated nucleic acids of the present invention can be made using (a) standard recombinant methods, (b) synthetic techniques or combinations thereof. In some embodiments, the polynucleotides of the present invention will be cloned, amplified or otherwise constructed from a monocot such as maize, rice or wheat or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.) and Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995).

A1. Full-Length Enriched cDNA Libraries

A number of cDNA synthesis protocols have been described which provide enriched full-length cDNA libraries. Enriched full-length cDNA libraries are constructed to comprise at least 600%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci, et al., (1996) Genomics, 37:327-336. Other methods for producing full-length libraries are known in the art. See, e.g., Edery, et al., (1995) *Mol. Cell. Biol.* 15(6):3363-3371 and PCT Application Number WO 1996/34981.

A2 Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, (1990) *Nucl. Acids. Res.* 18(19):5705-5711; Patanjali, et al., (1991) *Proc. Natl. Acad. U.S.A.* 88:1943-1947; U.S. Pat. Nos. 5,482,685, 5,482,845 and 5,637,685. In an exemplary method described by Soares, et al., normalization resulted in reduction of the abundance of clones from a range of four orders of magnitude to a narrow range of only 1 order of magnitude. *Proc. Natl. Acad. Sci. USA,* 91:9228-9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote, et al., in, *Plant Molecular Biology: A Laboratory Manual*, Clark, Ed., Springer-Verlag, Berlin (1997); Kho and Zarbl, (1991) *Technique* 3(2):58-63; Sive and St. John, (1988) *Nucl. Acids Res.,* 16(22):10937; *Current Protocols in Molecular Biology*, Ausubel, et al., Eds., Greene Publishing and Wiley-Interscience, New York (1995) and Swaroop, et al., (1991) *Nucl. Acids Res.,* 19(8):1954. cDNA subtraction kits are commercially available. See, e.g., PCR-Select (Clontech, Palo Alto, Calif.).

To construct genomic libraries, large segments of genomic DNA are generated by fragmentation, e.g., using restriction endonucleases, and are ligated with vector DNA to form concatemers that can be packaged into the appropriate vector. Methodologies to accomplish these ends and sequencing methods to verify the sequence of nucleic acids are well known in the art. Examples of appropriate molecular biological techniques and instructions sufficient to direct persons of skill through many construction, cloning and screening methodologies are found in Sambrook, et al., *Molecular Cloning A Laboratory Manual,* 2nd Ed., Cold Spring Harbor Laboratory Vols. 1-3 (1989), Methods in Enzymology, Vol. 152*: Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing or for other purposes. The T4 gene 32 protein (Boehringer Mannheim) can be used to improve yield of long PCR products.

PCR-based screening methods have been described. Wilfinger, et al., describe a PCR-based method in which the longest cDNA is identified in the first step so that incomplete clones can be eliminated from study. *BioTechniques,* 22(3): 481-486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68: 90-99; the phosphodiester method of Brown, et al., (1979) *Meth. Enzymol.* 68:109-151; the diethylphosphoramidite method of Beaucage, et al., (1981) *Tetra. Lett.* 22:1859-1862; the solid phase phosphoramidite triester method described by Beaucage and Caruthers, (1981) *Tetra. Letts.* 22(20):1859-1862, e.g., using an automated synthesizer, e.g., as described in Needham-VanDevanter, et al., (1984) *Nucleic Acids Res.,* 12:6159-6168 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as “constitutive” promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter and the GRP1-8 promoter.

Alternatively, the plant promoter can direct expression of a polynucleotide of the present invention in a specific tissue or may be otherwise under more precise environmental or developmental control. Such promoters are referred to here as “inducible” promoters. Environmental conditions that may effect transcription by inducible promoters include pathogen attack, anaerobic conditions or the presence of light. Examples of inducible promoters are the Adh1 promoter which is inducible by hypoxia or cold stress, the Hsp70 promoter which is inducible by heat stress and the PPDK promoter which is inducible by light.

Examples of promoters under developmental control include promoters that initiate transcription only, or preferentially, in certain tissues, such as leaves, roots, fruit, seeds or flowers. Exemplary promoters include the anther-specific promoter 5126 (U.S. Pat. Nos. 5,689,049 and 5,689,051), glb-1 promoter and gamma-zein promoter. Also see, for example, U.S. Patent Application Ser. Nos. 60/155,859 and 60/163,114. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase or alter concentration and/or composition of the proteins of the present invention in a desired tissue. Thus, in some embodiments, the nucleic acid construct will comprise a promoter, functional in a plant cell, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion and/or substitution (see, Kmiec, U.S. Pat. No. 5,565,350; Zarling, et al., PCT/US93/03868) or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes or from T-DNA. The 3' end sequence to be added can be derived from, for example, the nopaline synthase or octopine synthase genes or alternatively from another plant gene or less preferably from any other eukaryotic gene.

An intron sequence can be added to the 5' untranslated region or the coding sequence of the partial coding sequence to increase the amount of the mature message that accumulates in the cytosol. Inclusionon of a spliceable intron in the transcription unit in both plant and animal expression constructs has been shown to increase gene expression at both the mRNA and protein levels up to 1000-fold. Buchman and Berg, (1988) *Mol. Cell Biol.* 8:4395-4405; Callis, et al., (1987) *Genes Dev.* 1:1183-1200. Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994). The vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers, et al., (1987) *Meth. in Enzymol.* 153:253-277.

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy, et al., (1988) *Proc. Nat'l. Acad. Sci.* (*USA*) 85:8805-8809 and Hiatt, et al., U.S. Pat. No. 4,801,340.

Another method of suppression is sense suppression (i.e., co-supression). Introduction of nucleic acid configured in the sense orientation has been shown to be an effective means by which to block the transcription of target genes. For an example of the use of this method to modulate expression of endogenous genes see, Napoli, et al., (1990) *The Plant Cell* 2:279-289 and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff, et al., (1988) *Nature* 334:585-591.

A variety of cross-linking agents, alkylating agents and radical generating species as pendant groups on polynucleotides of the present invention can be used to bind, label, detect and/or cleave nucleic acids. For example, Vlassov, et al., (1986) *Nucleic Acids Res* 14:4065-4076, describe covalent bonding of a single-stranded DNA fragment with alkylating derivatives of nucleotides complementary to target sequences. A report of similar work by the same group is that by Knorre, et al., (1985) *Biochimie* 67:785-789. Iverson and Dervan also showed sequence-specific cleavage of single-stranded DNA mediated by incorporation of a modified nucleotide which was capable of activating cleavage (*J Am Chem Soc* (1987) 109:1241-1243). Meyer, et al., (1989) *J Am Chem Soc* 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, et al., (1988) *Biochemistry* 27:3197-3203. Use of crosslinking in triple-helix forming probes was also disclosed by Home, et al., (1990) *J Am Chem Soc* 112:2435-2437. Use of N4, N4-ethanocytosine as an alkylating agent to crosslink to single-stranded oligonucleotides has also been described by Webb and Matteucci, (1986) *J Am Chem Soc* 108:2764-2765; Nucleic Acids Res (1986) 14:7661-7674; Feteritz, et al., (1991) *J. Am. Chem. Soc.* 113:4000. Various compounds to bind, detect, label and/or cleave nucleic acids are known in the art. See, for example, U.S. Pat. Nos. 5,543,507; 5,672,593; 5,484,908; 5,256,648 and 5,681,941.

Proteins

The isolated proteins of the present invention comprise a polypeptide having at least 10 amino acids from a polypeptide of the present invention (or conservative variants thereof) such as those encoded by any one of the polynucleotides of the present invention as discussed more fully above (e.g., Table 1). The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35 or 40 amino acids in length, often at least 50, 60, 70, 80 or 90 amino acids in length. Further, the number of such subsequences can be any integer selected from the group consisting of from 1 to 20, such as 2, 3, 4 or 5.

The present invention further provides a protein comprising a polypeptide having a specified sequence identity/similarity with a polypeptide of the present invention. The percentage of sequence identity/similarity is an integer selected from the group consisting of from 50 to 99. Exemplary sequence identity/similarity values include 55%, 60%, 65%, 70%, 75%, 80%, 85%, 90% and 95%. Sequence identity can be determined using, for example, the GAP, CLUSTALW or BLAST algorithms.

As those of skill will appreciate, the present invention includes, but is not limited to, catalytically active polypeptides of the present invention (i.e., enzymes). Catalytically active polypeptides have a specific activity of at least 20%, 30% or 40% and preferably at least 50%, 60% or 70% and most preferably at least 80%, 90% or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80% or 90%. Methods of assaying and quantifying measures of enzymatic activity and substrate specificity ($k_{cat}/K_m$) are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located purification sequences. Restriction sites or termination codons can also be introduced.

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology Vol. 2: Special Methods in Peptide Synthesis, Part A*.; Merrifield, et al., (1963) *J. Am. Chem. Soc.* 85:2149-2156 and Stewart, et al., *Solid Phase Peptide Synthesis, 2nd ed*., Pierce Chem. Co., Rockford, III. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods and others. See, for instance, Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Introduction of Nucleic Acids into Host Cells

The method of introducing a nucleic acid of the present invention into a host cell is not critical to the instant invention. Transformation or transfection methods are conveniently used. Accordingly, a wide variety of methods have been developed to insert a DNA sequence into the genome of a host cell to obtain the transcription and/or translation of the sequence to effect phenotypic changes in the organism. Thus, any method which provides for effective introduction of a nucleic acid may be employed.

A. Plant Transformation

A nucleic acid comprising a polynucleotide of the present invention is optionally introduced into a plant. Generally, the polynucleotide will first be incorporated into a recombinant expression cassette or vector. Isolated nucleic acid acids of the present invention can be introduced into plants according to techniques known in the art. Techniques for transforming a wide variety of higher plant species are well known and described in the technical, scientific, and patent literature. See, for example, Weising, et al., (1988) *Ann. Rev. Genet.* 22:421-477. For example, the DNA construct may be introduced directly into the genomic DNA of the plant cell using techniques such as electroporation, polyethylene glycol (PEG) poration, particle bombardment, silicon fiber delivery or microinjection of plant cell protoplasts or embryogenic callus. See, e.g., Tomes, et al., Direct DNA Transfer into Intact Plant Cells Via Microprojectile Bombardment. pp. 197-213 in Plant Cell, Tissue and Organ Culture, Fundamental Methods. eds. Gamborg and Phillips. Springer-Verlag Berlin Heidelberg New York, 1995; see, U.S. Pat. No. 5,990, 387. The introduction of DNA constructs using PEG precipitation is described in Paszkowski, et al., (1984) *Embo J.* 3:2717-2722. Electroporation techniques are described in Fromm, et al., (1985) *Proc. Natl. Acad. Sci.* (USA) 82:5824. Ballistic transformation techniques are described in Klein, et al., (1987) *Nature* 327:70-73.

*Agrobacterium tumefaciens*-mediated transformation techniques are well described in the scientific literature. See, for example, Horsch, et al., (1984) *Science* 233:496-498; Fraley, et al., (1983) *Proc. Natl. Acad. Sci.* (USA) 80:4803 and *Plant Molecular Biology: A Laboratory Manual*, Chapter 8, Clark, Ed., Springer-Verlag, Berlin (1997). The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591, 616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, Rigby, Ed., London, Academic Press, 1987; and Lichtenstein, and Draper, In: DNA Cloning, Vol. II, Glover, Ed., Oxford, IRI Press, 1985), PCT Application Number PCT/US87/ 02512 (WO 1988/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman, et al., (1984) *Plant Cell Physiol.* 25:1353), (3) the vortexing method (see, e.g., Kindle, (1990) *Proc. Natl. Acad. Sci.*, (USA) 87:1228).

DNA can also be introduced into plants by direct DNA transfer into pollen as described by Zhou, et al., (1983) *Methods in Enzymology* 101:433; Hess, (1987) *Intern Rev. Cytol.* 107:367; Luo, et al., (1988) *Plant Mol. Biol. Reporter* 6:165. Expression of polypeptide coding genes can be obtained by injection of the DNA into reproductive organs of a plant as described by Pena, et al., (1987) *Nature,* 325.274. DNA can also be injected directly into the cells of immature embryos and the rehydration of desiccated embryos as described by Neuhaus, et al., (1987) *Theor. Appl. Genet.,* 75:30 and Benbrook, et al., in *Proceedings Bio Expo* 1986, Butterworth, Stoneham, Mass., pp. 27-54 (1986). A variety of plant viruses that can be employed as vectors are known in the art and include cauliflower mosaic virus (CaMV), geminivirus, brome mosaic virus and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics and micro-injection of the DNA directly into the cells. The transfected cells are cultured by means well known in the art. Kuchler, *Biochemical Methods in Cell Culture and Virology*, Dowden, Hutchinson and Ross, Inc. (1977).

Transgenic Plant Regeneration

Plant cells which directly result or are derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans, et al., *Protoplasts Isolation and Culture, Handbook of Plant Cell Culture*, Macmillan Publishing Company, New York, pp. 124-176 (1983) and Binding, *Regeneration of Plants, Plant Protoplasts*, CRC Press, Boca Raton, pp. 21-73 (1985).

The regeneration of plants from either single plant protoplasts or various explants is well known in the art. See, for example, *Methods for Plant Molecular Biology*, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement,* 3rd edition, Sprague and Dudley Eds., American Society of Agronomy, Madison, Wis. (1988). For transformation and regeneration of maize see, Gordon-Kamm, et al., (1990) *The Plant Cell* 2:603-618.

The regeneration of plants containing the polynucleotide of the present invention and introduced by *Agrobacterium* from leaf explants can be achieved as described by Horsch, et al., (1985) *Science,* 227:1229-1231. In this procedure, transformants are grown in the presence of a selection agent and in a medium that induces the regeneration of shoots in the plant species being transformed as described by Fraley, et al., (1983) *Proc. Natl. Acad. Sci*. (U.S.A.) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell a recombinant expression cassette comprising a polynucleotide of the present invention as described above to obtain a transgenic plant cell, culturing the transgenic plant cell under transgenic plant cell growing conditions and inducing or repressing expression of a polynucleotide of the present invention in the transgenic plant for a time sufficient to modulate concentration and/or the ratios of the polypeptides in the transgenic plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion or deletion to decrease activity of the encoded enzyme. (See, e.g., Kmiec, U.S. Pat. No. 5,565,350; Zarling, et al., PCT/US93/03868.) And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80% or 90% relative to a native control plant, plant part or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 7-methylguanosine cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell.*

*Biol.* 8:284). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as “Codon Preference” available from the University of Wisconsin Genetics Computer Group (see, Devereaux, et al., (1984) *Nucleic Acids Res.* 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication Number WO 1997/20078. See also, Zhang, et al., (1997) *Proc. Natl. Acad. Sci. USA* 94:4504-4509. Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system and may include properties of: an encoded protein, a transcriptional element, a sequence controlling transcription, RNA processing, RNA stability, chromatin conformation, translation or other expression property of a gene or transgene, a replicative element, a protein-binding element or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla or kingdoms. For example, a polynucleotide having a consensus sequence from a gene family of *Zea mays* can be used to generate antibody or nucleic acid probes or primers to other *Gramineae* species such as wheat, rice or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30 or 40 amino acids in length, or 20, 30, 40, 50, 100 or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001 and most preferably less than about 0.0001 or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Machine Applications

The present invention provides machines, data structures, and processes for modeling or analyzing the polynucleotides and polypeptides of the present invention.

A. Machines: Data, Data Structures, Processes and Functions

The present invention provides a machine having a memory comprising: 1) data representing a sequence of a polynucleotide or polypeptide of the present invention, 2) a data structure which reflects the underlying organization and structure of the data and facilitates program access to data elements corresponding to logical sub-components of the sequence, 3) processes for effecting the use, analysis, or modeling of the sequence, and 4) optionally, a function or utility for the polynucleotide or polypeptide. Thus, the present invention provides a memory for storing data that can be accessed by a computer programmed to implement a process for affecting the use, analyses or modeling of a sequence of a polynucleotide, with the memory comprising data representing the sequence of a polynucleotide of the present invention.

The machine of the present invention is typically a digital computer. The term “computer” includes one or several desktop or portable computers, computer workstations, servers (including intranet or internet servers), mainframes and any integrated system comprising any of the above irrespective of whether the processing, memory, input or output of the computer is remote or local, as well as any networking interconnecting the modules of the computer. The term "computer" is exclusive of computers of the United States Patent and Trademark Office or the European Patent Office when data representing the sequence of polypeptides or polynucleotides of the present invention is used for patentability searches.

The present invention contemplates providing as data a sequence of a polynucleotide of the present invention embodied in a computer readable medium. As those of skill in the art will be aware, the form of memory of a machine of the present invention or the particular embodiment of the computer readable medium, are not critical elements of the invention and can take a variety of forms. The memory of such a machine includes, but is not limited to, ROM or RAM or computer readable media such as, but not limited to, magnetic media such as computer disks or hard drives or media such as CD-ROMs, DVDs and the like.

The present invention further contemplates providing a data structure that is also contained in memory. The data structure may be defined by the computer programs that define the processes (see below) or it may be defined by the programming of separate data storage and retrieval programs subroutines or systems. Thus, the present invention provides a memory for storing a data structure that can be accessed by a computer programmed to implement a process for affecting the use, analysis or modeling of a sequence of a polynucleotide. The memory comprises data representing a polynucleotide having the sequence of a polynucleotide of the present invention. The data is stored within memory. Further, a data structure, stored within memory, is associated with the data reflecting the underlying organization and structure of the data to facilitate program access to data elements corresponding to logical sub-components of the sequence. The data structure enables the polynucleotide to be identified and manipulated by such programs.

In a further embodiment, the present invention provides a data structure that contains data representing a sequence of a polynucleotide of the present invention stored within a computer readable medium. The data structure is organized to reflect the logical structuring of the sequence, so that the sequence is easily analyzed by software programs capable of accessing the data structure. In particular, the data structures of the present invention organize the reference sequences of the present invention in a manner which allows software tools to perform a wide variety of analyses using logical elements and sub-elements of each sequence.

An example of such a data structure resembles a layered hash table, where in one dimension the base content of the sequence is represented by a string of elements A, T, C, G and N. The direction from the 5' end to the 3' end is reflected by the order from the position 0 to the position of the length of the string minus one. Such a string, corresponding to a nucleotide sequence of interest, has a certain number of substrings, each of which is delimited by the string position of its 5' end and the string position of its 3' end within the parent string. In a second dimension, each substring is associated with or pointed to one or multiple attribute fields. Such attribute fields contain annotations to the region on the nucleotide sequence represented by the substring.

For example, a sequence under investigation is 520 bases long and represented by a string named SeqTarget. There is a minor groove in the 5' upstream non-coding region from position 12 to 38, which is identified as a binding site for an enhancer protein HM-A, which in turn will increase the transcription of the gene represented by SeqTarget. Here, the substring is represented as (12, 38) and has the following attributes: [upstream uncoded], [minor groove], [HM-A binding] and [increase transcription upon binding by HM-A]. Similarly, other types of information can be stored and structured in this manner, such as information related to the whole sequence, e.g., whether the sequence is a full length viral gene, a mammalian house keeping gene or an EST from clone X, information related to the 3' down stream non-coding region, e.g., hair pin structure and information related to various domains of the coding region, e.g., Zinc finger.

This data structure is an open structure and is robust enough to accommodate newly generated data and acquired knowledge. Such a structure is also a flexible structure. It can be trimmed down to a 1-D string to facilitate data mining and analysis steps, such as clustering, repeat-masking, and HMM analysis. Meanwhile, such a data structure also can extend the associated attributes into multiple dimensions. Pointers can be established among the dimensioned attributes when needed to facilitate data management and processing in a comprehensive genomics knowledgebase. Furthermore, such a data structure is object-oriented. Polymorphism can be represented by a family or class of sequence objects, each of which has an internal structure as discussed above. The common traits are abstracted and assigned to the parent object, whereas each child object represents a specific variant of the family or class. Such a data structure allows data to be efficiently retrieved, updated and integrated by the software applications associated with the sequence database and/or knowledgebase.

The present invention contemplates providing processes for effecting analysis and modeling, which are described in the following section.

Optionally, the present invention further contemplates that the machine of the present invention will embody in some manner a utility or function for the polynucleotide or polypeptide of the present invention. The function or utility of the polynucleotide or polypeptide can be a function or utility for the sequence data, per se, or of the tangible material. Exemplary function or utilities include the name (per International Union of Biochemistry and Molecular Biology rules of nomenclature) or function of the enzyme or protein represented by the polynucleotide or polypeptide of the present invention; the metabolic pathway of the protein represented by the polynucleotide or polypeptide of the present invention; the substrate or product or structural role of the protein represented by the polynucleotide or polypeptide of the present invention or the phenotype (e.g., an agronomic or pharmacological trait) affected by modulating expression or activity of the protein represented by the polynucleotide or polypeptide of the present invention.

B. Computer Analysis and Modeling

The present invention provides a process of modeling and analyzing data representative of a polynucleotide or polypeptide sequence of the present invention. The process comprises entering sequence data of a polynucleotide or polypeptide of the present invention into a machine having a hardware or software sequence modeling and analysis system, developing data structures to facilitate access to the sequence data, manipulating the data to model or analyze the structure or activity of the polynucleotide or polypeptide and displaying the results of the modeling or analysis. Thus, the present invention provides a process for affecting the use, analysis or modeling of a polynucleotide sequence or its derived peptide sequence through use of a computer having a memory. The process comprises: 1) placing into the memory data representing a polynucleotide having the sequence of a polynucleotide of the present invention, developing within the memory a data structure associated with the data and reflecting the underlying organization and structure of the data to facilitate program access to data elements corresponding to logical sub-components of the sequence, 2) programming the computer with a program containing instructions sufficient to implement the process for effecting the use, analysis or modeling of the polynucleotide sequence or the peptide sequence and 3) executing the program on the computer while granting the program access to the data and to the data structure within the memory.

A variety of modeling and analytic tools are well known in the art and available commercially. Included amongst the modeling/analysis tools are methods to: 1) recognize overlapping sequences (e.g., from a sequencing project) with a polynucleotide of the present invention and create an alignment called a "contig"; 2) identify restriction enzyme sites of a polynucleotide of the present invention; 3) identify the products of a T1 ribonuclease digestion of a polynucleotide of the present invention; 4) identify PCR primers with minimal self-complementarity; 5) compute pairwise distances between sequences in an alignment, reconstruct phylogentic trees using distance methods and calculate the degree of divergence of two protein coding regions; 6) identify patterns such as coding regions, terminators, repeats and other consensus patterns in polynucleotides of the present invention; 7) identify RNA secondary structure; 8) identify sequence motifs, isoelectric point, secondary structure, hydrophobicity and antigenicity in polypeptides of the present invention; 9) translate polynucleotides of the present invention and back-translate polypeptides of the present invention and 10) compare two protein or nucleic acid sequences and identifying points of similarity or dissimilarity between them.

The processes for effecting analysis and modeling can be produced independently or obtained from commercial suppliers. Exemplary analysis and modeling tools are provided in products such as InforMax's (Bethesda, Md.) Vector NTI Suite (Version 5.5), Intelligenetics' (Mountain View, Calif.) PC/Gene program and Genetics Computer Group's (Madison, Wis.) Wisconsin Package® (Version 10.0); these tools, and the functions they perform, (as provided and disclosed by the programs and accompanying literature) are incorporated herein by reference and are described in more detail in section C which follows.

Thus, in a further embodiment, the present invention provides a machine-readable media containing a computer program and data, comprising a program stored on the media containing instructions sufficient to implement a process for affecting the use, analysis or modeling of a representation of a polynucleotide or peptide sequence. The data stored on the media represents a sequence of a polynucleotide having the sequence of a polynucleotide of the present invention. The media also includes a data structure reflecting the underlying organization and structure of the data to facilitate program access to data elements corresponding to logical sub-components of the sequence, the data structure being inherent in the program and in the way in which the program organizes and accesses the data.

C. Homology Searches

As an example of such a comparative analysis, the present invention provides a process of identifying a candidate homologue (i.e., an ortholog or paralog) of a polynucleotide or polypeptide of the present invention. The process comprises entering sequence data of a polynucleotide or polypeptide of the present invention into a machine having a hardware or software sequence analysis system, developing data structures to facilitate access to the sequence data, manipulating the data to analyze the structure the polynucleotide or polypeptide and displaying the results of the analysis. A candidate homologue has statistically significant probability of having the same biological function (e.g., catalyzes the same reaction, binds to homologous proteins/nucleic acids, has a similar structural role) as the reference sequence to which it is compared. Accordingly, the polynucleotides and polypeptides of the present invention have utility in identifying homologs in animals or other plant species, particularly those in the family *Gramineae* such as, but not limited to, sorghum, wheat or rice.

The process of the present invention comprises obtaining data representing a polynucleotide or polypeptide test sequence. Test sequences can be obtained from a nucleic acid of an animal or plant. Test sequences can be obtained directly or indirectly from sequence databases including, but not limited to, those such as: GenBank, EMBL, GenSeq, SWISS-PROT or those available on-line via the UK Human Genome Mapping Project (HGMP) GenomeWeb. In some embodiments the test sequence is obtained from a plant species other than maize whose function is uncertain but will be compared to the test sequence to determine sequence similarity or sequence identity. The test sequence data is entered into a machine, such as a computer, containing: i) data representing a reference sequence and ii) a hardware or software sequence comparison system to compare the reference and test sequence for sequence similarity or identity.

Exemplary sequence comparison systems are provided for in sequence analysis software such as those provided by the Genetics Computer Group (Madison, Wis.) or InforMax (Bethesda, Md.) or Intelligenetics (Mountain View, Calif.). Optionally, sequence comparison is established using the BLAST or GAP suite of programs. Generally, a smallest sum probability value (P(N)) of less than 0.1, or alternatively, less than 0.01, 0.001, 0.0001 or 0.00001 using the BLAST 2.0 suite of algorithms under default parameters identifies the test sequence as a candidate homologue (i.e., an allele, ortholog or paralog) of the reference sequence. Those of skill in the art will recognize that a candidate homologue has an increased statistical probability of having the same or similar function as the gene/protein represented by the test sequence.

The reference sequence can be the sequence of a polypeptide or a polynucleotide of the present invention. The reference or test sequence is each optionally at least 25 amino acids or at least 100 nucleotides in length. The length of the reference or test sequences can be the length of the polynucleotide or polypeptide described, respectively, above in the sections entitled "Nucleic Acids" (particularly section (g)) and "Proteins". As those of skill in the art are aware, the greater the sequence identity/similarity between a reference sequence of known function and a test sequence, the greater the probability that the test sequence will have the same or similar function as the reference sequence. The results of the comparison between the test and reference sequences are outputted (e.g., displayed, printed, recorded) via any one of a number of output devices and/or media (e.g., computer monitor, hard copy or computer readable medium).

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a cognate gene of a polynucleotide of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result. Detection of the hybridization complex can be achieved using any number of well known methods. For example, the nucleic acid sample, or a portion thereof, may be assayed by hybridization formats including but not limited to, solution phase, solid phase, mixed phase or in situ hybridization assays.

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes, radiolabels, enzymes and colorimetric labels. Other labels include ligands which bind to antibodies labeled with fluorophores, chemiluminescent agents and enzymes. Labeling the nucleic acids of the present invention is readily achieved such as by the use of labeled PCR primers.

Although the present invention has been described in some detail by way of illustration and example for purposes of clarity of understanding, it will be obvious that certain changes and modifications may be practiced within the scope of the appended claims.

EXAMPLE 1

This example describes the construction of a cDNA library.

Total RNA can be isolated from maize tissues with TRIzol Reagent (Life Technology Inc. Gaithersburg, Md.) using a modification of the guanidine isothiocyanate/acid-phenol procedure described by Chomczynski and Sacchi (Chomczynski and Sacchi, (1987) *Anal. Biochem.* 162:156). In brief, plant tissue samples is pulverized in liquid nitrogen before the addition of the TRIzol Reagent and then further homogenized with a mortar and pestle. Addition of chloroform followed by centrifugation is conducted for separation of an aqueous phase and an organic phase. The total RNA is recovered by precipitation with isopropyl alcohol from the aqueous phase.

The selection of poly(A)+ RNA from total RNA can be performed using PolyATact system (Promega Corporation. Madison, Wis.). Biotinylated oligo(dT) primers are used to hybridize to the 3' poly(A) tails on mRNA. The hybrids are captured using streptavidin coupled to paramagnetic particles and a magnetic separation stand. The mRNA is then washed at high stringency conditions and eluted by RNase-free deionized water.

cDNA synthesis and construction of unidirectional cDNA libraries can be accomplished using the SuperScript Plasmid System (Life Technology Inc. Gaithersburg, Md.). The first strand of cDNA is synthesized by priming an oligo(dT) primer containing a Not I site. The reaction is catalyzed by SuperScript Reverse Transcriptase II at 45° C. The second strand of cDNA is labeled with alpha-$^{32}$P-dCTP and a portion of the reaction analyzed by agarose gel electrophoresis to determine cDNA sizes. cDNA molecules smaller than 500 base pairs and unligated adapters are removed by Sephacryl-5400 chromatography. The selected cDNA molecules are ligated into pSPORT1 vector in between of Not I and Sal I sites.

Alternatively, cDNA libraries can be prepared by any one of many methods available.

For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see, Adams, et al., (1991) *Science* 252:1651-1656). The resulting ESTs are analyzed using a Perkin Elmer Model 377 fluorescent sequencer.

EXAMPLE 2

This method describes construction of a full-length enriched cDNA library.

An enriched full-length cDNA library can be constructed using one of two variations of the method of Carninci, et al., (1996) *Genomics* 37:327-336. These variations are based on chemical introduction of a biotin group into the diol residue of the 5' cap structure of eukaryotic mRNA to select full-length first strand cDNA. The selection occurs by trapping the biotin residue at the cap sites using streptavidin-coated magnetic beads followed by RNase I treatment to eliminate incompletely synthesized cDNAs. Second strand cDNA is synthesized using established procedures such as those provided in Life Technologies' (Rockville, Md.) "SuperScript Plasmid System for cDNA Synthesis and Plasmid Cloning" kit. Libraries made by this method have been shown to contain 50% to 70% full-length cDNAs.

The first strand synthesis methods are detailed below. An asterisk denotes that the reagent was obtained from Life Technologies, Inc.

A. First Strand cDNA Synthesis Method 1 (with Trehalose)

| | |
|---|---|
| mRNA (10 ug) | 25 μl |
| *Not I primer (5 ug) | 10 μl |
| *5x 1$^{st}$ strand buffer | 43 μl |
| *0.1 m DTT | 20 μl |
| *dNTP mix 10 mm | 10 μl |
| BSA 10 ug/μl | 1 μl |
| Trehalose (saturated) | 59.2 μl |
| RNase inhibitor (Promega) | 1.8 μl |
| *Superscript II RT 200 u/μl | 20 μl |
| 100% glycerol | 18 μl |
| Water | 7 μl |

The mRNA and Not I primer are mixed and denatured at 65° C. for 10 min. They are then chilled on ice and other components added to the tube. Incubation is at 45° C. for 2 min. Twenty microliters of RT (reverse transcriptase) is added to the reaction and start program on the thermocycler (MJ Research, Waltham, Mass.):

| | | |
|---|---|---|
| Step 1 | 45° C. | 10 min |
| Step 2 | 45° C. | −0.3° C./cycle, 2 seconds/cycle |
| Step 3 | go to 2 for 33 cycles | |
| Step 4 | 35° C. | 5 min |
| Step 5 | 45° C. | 5 min |
| Step 6 | 45° C. | 0.2° C./cycle, 1 sec/cycle |
| Step 7 | go to 7 for 49 cycles | |
| Step 8 | 55° C. | 0.1° C./cycle, 12 sec/cycle |
| Step 9 | go to 8 for 49 cycles | |
| Step 10 | 55° C. | 2 min |
| Step 11 | 60° C. | 2 min |
| Step 12 | go to 11 for 9 times | |
| Step 13 | 4° C. forever | |
| Step 14 | end | |

B. First Strand cDNA Synthesis Method 2

| | |
|---|---|
| mRNA (10 μg) | 25 μl |
| water | 30 μl |
| *Not I adapter primer (5 μg) | 10 μl |
| 65° C. for 10 min, chill on ice, then add following reagents, | |
| *5x first buffer | 20 μl |
| *0.1M DTT | 10 μl |
| *10 mM dNTP mix | 5 μl |

Incubate at 45° C. for 2 min, then add 10 μl of *Superscript II RT (200 u/μl), start the following program:

| | |
|---|---|
| Step 1 | 45° C. for 6 sec, −0.1° C./cycle |
| Step 2 | go to 1 for 99 additional cycles |
| Step 3 | 35° C. for 5 min |
| Step 4 | 45° C. for 60 min |
| Step 5 | 50° C. for 10 min |
| Step 6 | 4° C. forever |
| Step 7 | end |

After the 1st strand cDNA synthesis, the DNA is extracted by phenol according to standard procedures, and then precipitated in NaOAc and ethanol, and stored in −20° C.

C. Oxidization of the Diol Group of mRNA for Biotin Labeling

First strand cDNA is spun down and washed once with 70% EtOH. The pellet resuspended in 23.2 μl of DEPC treated water and put on ice. Prepare 100 mM of NaIO4 freshly and then add the following reagents:

| | |
|---|---|
| mRNA:1st cDNA (start with 20 μg mRNA) | 46.4 μl |
| 100 mM NaIO4 (freshly made) | 2.5 μl |
| NaOAc 3M pH 4.5 | 1.1 μl |

To make 100 mM $NaIO_4$, use 21.39 μg of $NaIO_4$ for 1 μl of water.

Wrap the tube in a foil and incubate on ice for 45 min.

After the incubation, the reaction is then precipitated in:

| | |
|---|---|
| 5M NaCl | 10 μl |
| 20% SDS | 0.5 μl |
| isopropanol | 61 μl |

Incubate on ice for at least 30 min, then spin it down at max speed at 4° C. for 30 min and wash once with 70% ethanol and then 80% EtOH.

D. Biotinylation of the mRNA Diol Group

Resuspend the DNA in 110 μl DEPC treated water, then add the following reagents:

| | |
|---|---|
| 20% SDS | 5 μl |
| 2M NaOAc pH 6.1 | 5 μl |
| 10 mm biotin hydrazide (freshly made) | 300 μl |

Wrap in a foil and incubate at room temperature overnight.

E. RNase I Treatment

Precipitate DNA in:

| | |
|---|---|
| 5M NaCl | 10 μl |
| 2M NaOAc pH 6.1 | 75 μl |
| biotinylated mRNA:cDNA | 420 μl |
| 100% EtOH (2.5 Vol) | 1262.5 μl |

(Perform this precipitation in two tubes and split the 420 μl of DNA into 210 μl each, add 5 μl of 5M NaCl, 37.5 μl of 2M NaOAc pH 6.1 and 631.25 μl of 100% EtOH).

Store at −20° C. for at least 30 min. Spin the DNA down at 4° C. at maximal speed for 30 min. and wash with 80% EtOH twice, then dissolve DNA in 70 μl RNase free water. Pool two tubes and end up with 140 μl.

Add the following reagents:

| | |
|---|---|
| RNase One 10 U/μl | 40 μl |
| 1st cDNA:RNA | 140 μl |
| 10X buffer | 20 μl |

Incubate at 37° C. for 15 min.

Add 5 μl of 40 μg/μl yeast tRNA to each sample for capturing.

F. Full Length 1st cDNA Capturing

Blocking the beads with yeast tRNA:

| | |
|---|---|
| Beads | 1 ml |
| Yeast tRNA 40 μg/μl | 5 μl |

Incubate on ice for 30 min with mixing, wash 3 times with 1 ml of 2M NaCl, 50 mmEDTA, pH 8.0.

Resuspend the beads in 800 μl of 2M NaCl, 50 mm EDTA, pH 8.0, add RNase I treated sample 200 μl, and incubate the reaction for 30 min at room temperature.

Capture the beads using the magnetic stand, save the supernatant, and start following washes:

2 washes with 2M NaCl, 50 mm EDTA, pH 8.0, 1 ml each time, 1 wash with 0.4% SDS, 50 μg/ml tRNA, 1 wash with 10 mm Tris-Cl pH 7.5, 0.2 mm EDTA, 10 mm NaCl, 20% glycerol, 1 wash with 50 μg/ml tRNA, 1 wash with 1st cDNA buffer G. Second Strand cDNA Synthesis Resuspend the beads in:

| | |
|---|---|
| *5X first buffer | 8 μl |
| *0.1 mM DTT | 4 μl |

-continued

| | |
|---|---|
| *10 mm dNTP mix | 8 µl |
| *5X 2nd buffer | 60 µl |
| **E. coli* Ligase 10 U/µl | 2 µl |
| **E. coli* DNA polymerase 10 U/µl | 8 µl |
| **E. coli* RNaseH 2 U/µl | 2 µl |
| P32 dCTP 10 µci/µl | 2 µl |
| Or water up to 300 µl | 208 µl |

Incubate at 16° C. for 2 hr with mixing the reaction in every 30 min.

Add 4 µl of T4 DNA polymerase and incubate for additional 5 min at 16° C.

Elute $2^{nd}$ cDNA from the beads.

Use a magnetic stand to separate the $2^{nd}$ cDNA from the beads, then resuspend the beads in 200 µl of water, and then separate again, pool the samples (about 500 µl), Add 200 µl of water to the beads, then 200 µl of phenol: chloroform, vortex and spin to separate the sample with phenol.

Pool the DNA together (about 700 µl) and use phenol to clean the DNA again, DNA is then precipitated in 2 µg of glycogen and 0.5 vol of 7.5M NH4OAc and 2 vol of 100% EtOH. Precipitate overnight. Spin down the pellet and wash with 70% EtOH, air-dry the pellet.

| | | | |
|---|---|---|---|
| DNA | 250 µl | DNA | 200 µl |
| 7.5M NH4OAc | 125 µl | 7.5M NH4OAc | 100 µl |
| 100% EtOH | 750 µl | 100% EtOH | 600 µl |
| glycogen 1 µg/µl | 2 µl | glycogen 1 µg/µl | 2 µl |

H. Sal I Adapter Ligation

Resuspend the pellet in 26 µl of water and use 1 µl for TAE gel.

Set up reaction as following:

| | |
|---|---|
| $2^{nd}$ strand cDNA | 25 µl |
| *5X T4 DNA ligase buffer | 10 µl |
| *Sal I adapters | 10 µl |
| *T4 DNA ligase | 5 µl |

Mix gently, incubate the reaction at 16° C. overnight.

Add 2 µl of ligase second day and incubate at room temperature for 2 hrs (optional).

Add 50 µl water to the reaction and use 100 µl of phenol to clean the DNA, 90 µl of the upper phase is transferred into a new tube and precipitate in:

| | |
|---|---|
| Glycogen 1µg/µl | 2 µl |
| Upper phase DNA | 90 µl |
| 7.5M NH4OAc | 50 µl |
| 100% EtOH | 300 µl |

precipitate at −20° C. overnight

Spin down the pellet at 4° C. and wash in 70% EtOH, dry the pellet.

I. Not I Digestion

| | |
|---|---|
| $2^{nd}$ cDNA | 41 µl |
| *Reaction 3 buffer | 5 µl |
| *Not I 15 u/µl | 4 µl |

Mix gently and incubate the reaction at 37° C. for 2 hr.

Add 50 µl of water and 100 µl of phenol, vortex, and take 90 µl of the upper phase to a new tube, then add 50 µl of $NH_40Ac$ and 300 µl of EtOH. Precipitate overnight at −20° C.

Cloning, ligation and transformation are performed per the Superscript cDNA synthesis kit.

EXAMPLE 3

This example describes cDNA sequencing and library subtraction.

Individual colonies can be picked and DNA prepared either by PCR with M13 forward primers and M13 reverse primers or by plasmid isolation. cDNA clones can be sequenced using M13 reverse primers.

cDNA libraries are plated out on 22×22 $cm^2$ agar plate at density of about 3,000 colonies per plate. The plates are incubated in a 37° C. incubator for 12-24 hours. Colonies are picked into 384-well plates by a robot colony picker, Q-bot (GENETIX Limited). These plates are incubated overnight at 37° C. Once sufficient colonies are picked, they are pinned onto 22×22 $cm^2$ nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40-50 minutes. The filters are placed on dry filter papers to dry overnight. DNA is then cross-linked to nylon membrane by UV light treatment Colony hybridization is conducted as described by Sambrook, et al., (in Molecular Cloning: A laboratory Manual, $2^{nd}$ Edition). The following probes can be used in colony hybridization:

1. First strand cDNA from the same tissue as the library was made from to remove the most redundant clones.
2. 48-192 most redundant cDNA clones from the same library based on previous sequencing data.
3. 192 most redundant cDNA clones in the entire maize sequence database.
4. A Sal-A20 oligo nucleotide: TCG ACC CAC GCG TCC GAA AAA AAA AAA AAA AAA AAA, SEQ ID NO: 31, removes clones containing a poly A tail but no cDNA.
5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.

EXAMPLE 4

This example describes identification of the gene from a computer homology search.

Gene identities can be determined by conducting BLAST (Basic Local Alignment Search Tool; Altschul, et al., (1993) *J. Mol. Biol.* 215:403-410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish and States, (1993) *Nature Genetics* 3:266-272) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignments of the sequences can be performed using the Clustal method of alignment (Higgins and Sharp, (1989) *CABIOS*. 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

Other methods of sequence alignment and percent identity analysis known to those of skill in the art, including those disclosed herein, can also be employed.

EXAMPLE 5

This example describes expression of transgenes in monocot cells.

A transgene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209) and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue; Stratagene). Bacterial transformants can be screened by restriction enzyme digestion of plasmid DNA and limited nucleotide sequence analysis using the dideoxy chain termination method (Sequenase DNA Sequencing Kit; US Biochemical). The resulting plasmid construct would comprise a transgene encoding, in the 5' to 3' direction, the maize 27 kD zein promoter, a cDNA fragment encoding the instant polypeptides and the 10 kD zein 3' region.

The transgene described above can then be introduced into maize cells by the following procedure. Immature maize embryos can be dissected from developing caryopses derived from crosses of the inbred maize lines H99 and LH132. The embryos are isolated 10 to 11 days after pollination when they are 1.0 to 1.5 mm long. The embryos are then placed with the axis-side facing down and in contact with agarose-solidified N6 medium (Chu, et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (Hoechst Ag, Frankfurt, Germany) or equivalent may be used in transformation experiments in order to provide for a selectable marker. This plasmid contains the Pat gene (see, EP Patent Publication Number 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, et al., (1985) *Nature* 313:810-812) and the 3' region of the nopaline synthase gene from the T-DNA of the Ti plasmid of *Agrobacterium tumefaciens*.

The particle bombardment method (Klein, et al., (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton flying disc (Bio-Rad Labs). The particles are then accelerated into the maize tissue with a Biolistic PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

EXAMPLE 6

This example describes expression of transgenes in dicot cells.

A seed-specific expression cassette composed of the promoter and transcription terminator from the gene encoding the β subunit of the seed storage protein phaseolin from the bean *Phaseolus vulgaris* (Doyle, et al., (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) *Nature* (London) 327:70-73, U.S. Pat. No. 4,945,050). A DuPont Biolistic PDS1000/HE instrument (helium retrofit) can be used for these transformations.

A selectable marker gene which can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μmgold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 7

This example describes expression of a transgene in microbial cells.

The cDNAs encoding the instant polypeptides can be inserted into the T7 *E. coli* expression vector pBT430. This vector is a derivative of pET-3a (Rosenberg, et al., (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG low melting agarose gel (FMC). Buffer and agarose contain 10 μg/ml ethidium bromide for visualization of the DNA fragment. The fragment can then be purified from the agarose gel by digestion with GELase (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16°

C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier, et al., (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One microgram of protein from the soluble fraction of the culture can be separated by SDS-polyacrylamide gel electrophoresis. Gels can be observed for protein bands migrating at the expected molecular weight.

EXAMPLE 8

Isolation of the CesA10, 11 and 12 genes and their relevance to cell wall synthesis and stalk strength in maize All three genes were isolated from a library made from the zone of an elongating corn stalk internode between the elongation zone and the most mature part of the internode, the "transition zone". The library was made, subtracted, and sequenced as described in the preceding Examples 1, 2 and 3. A genomic database search was conducted as described in Example 4. Derived polypeptide sequences of all the Expressed Tag Sequences (ESTs) showing homology to the 1 kb 5'-end of any of the 9 previously known ZmCesA genes were aligned with the protein sequences of the latter. The sequences that did not fully match any of the known genes were sequenced from both ends of the respective cDNA clones. Three new, full-length genes, ZmCesA10 (SEQ ID NO: 25), ZmCesA11 (SEQ ID NO: 27) and ZmCesA12 (SEQ ID NO: 29) were isolated by this method.

The polypeptide sequences of the three genes derived from the cDNA sequences (SEQ ID NOS: 26, 28 and 30, respectively) clustered with the CesA genes from other species where they are known to be involved in secondary wall formation (FIG. 4). AtCesA7 and AtCesA8 have been found to make secondary wall in the vascular bundles (Taylor, et al., (2000). Multiple cellulose synthase catalytic subunits are required for cellulose synthesis in *Arabidopsis*. *Plant Cell*, (2000) 12:2529-2539). Retrotransposon insertions into OsCesA4 and OsCesA7 resulted in a brittle culm phenotype in rice (Katsuyuki Tanaka, Akio Miyao, Kazumasa Murata, Katsura Onosato, Naoko Kojima, Yumiko Yamashita, Mayuko Harada, Takuji Sasaki, Hirohiko Hirochika, 2002, Analysis of rice brittle mutants caused by disruption of cellulose synthase genes OsCesA4 and OsCesA11 with the retrotransposon tos17. Plant, Animal & Microbe Genomes X. San Diego, Calif. Abs. Number 324). Each of the genes, ZmCesA 10, 11 or 12, groups with one or the other CesA gene from *Arabidopsis* or rice known to be involved in secondary wall formation and thus in determining tissue strength (FIG. 4). The CesA genes derived from the tissues specializing in secondary wall formation from other species (*Gossypium, Zinnia, Populus*) also group into the same clades with the aforementioned genes.

Figure 5:
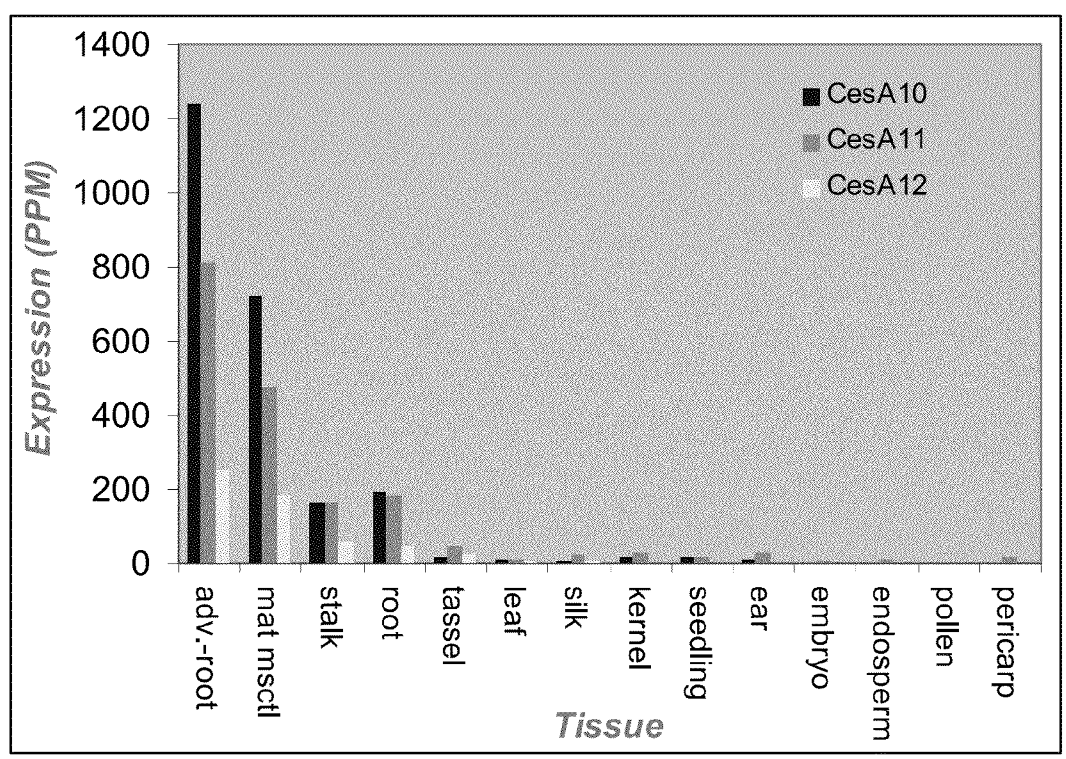
FIG. 5: Expression pattern of CesA10, 11 and 12 in different maize tissues. All three genes are nearly synchronously expressed in tissues rich in secondary wall.

Further evidence that the maize genes are involved in secondary wall formation and thus in determining stalk strength was obtained from their expression pattern using the Massively Parallel Signature Sequencing (MPSS) technology (Brenner, et al., (2000), In vitro cloning of complex mixtures of DNA on microbeads: Physical separation of differentially expressed cDNAs. *Proceedings-of-the-National-Academy-of-Sciences-of-the-United-States-of-America* (Feb. 15, 2000) 97:1665-1670; see also, Brenner, et al., (2000) Gene expression analysis by massively parallel signature sequencing (MPSS) on microbead arrays. *Nature-Biotechnolog*, [print] (June 2000) 18:630-634; see also, Dhugga, (2001), Building the wall: genes and enzyme complexes for polysaccharide synthases, *Curr. Opin. Plant Biol.* 4:488-493). All three genes are expressed in the tissues rich in cell wall content, supporting their involvement in secondary wall formation as deduced from their relationship to the genes from the other, aforementioned species know to play this role (FIG. 5). All three genes are expressed nearly identically across multiple tissues as seen from the correlation coefficient matrix (Table 3), further strengthening the argument that they are involved in secondary wall formation in the vascular bundles and thus in determining tissue strength.

Correlation among the expression level of the different CesA genes from maize as studied from Lynx are shown in Table 3.

TABLE 3

| | CesA1 | CesA2 | CesA3 | CesA4 | CesA5 | CesA6 | CesA7 | CesA8 | CesA10 | CesA11 | CesA12 |
|---|---|---|---|---|---|---|---|---|---|---|---|
| CesA1 | 1 | | | | | | | | | | |
| CesA2 | 0.59 | 1.00 | | | | | | | | | |
| CesA3 | 0.07 | −0.15 | 1.00 | | | | | | | | |
| CesA4 | 0.44 | 0.55 | −0.10 | 1.00 | | | | | | | |
| CesA5 | −0.20 | −0.29 | 0.45 | −0.33 | 1.00 | | | | | | |
| CesA6 | 0.56 | 0.14 | 0.14 | 0.08 | −0.13 | 1.00 | | | | | |
| CesA7 | 0.68 | 0.76 | −0.06 | 0.57 | −0.29 | 0.32 | 1.00 | | | | |
| CesA8 | 0.59 | 0.73 | −0.16 | 0.58 | −0.36 | 0.26 | 0.61 | 1.00 | | | |
| CesA10 | 0.27 | 0.37 | −0.27 | 0.33 | −0.26 | 0.02 | 0.33 | 0.36 | 1.00 | | |
| CesA11 | 0.39 | 0.47 | −0.22 | 0.38 | −0.28 | 0.11 | 0.40 | 0.42 | 0.95 | 1.00 | |
| CesA12 | 0.34 | 0.49 | −0.27 | 0.37 | −0.31 | 0.08 | 0.44 | 0.45 | 0.95 | 0.95 | 1 |

The correlation matrix was derived from the expression, measured in PPM, from 65 different tissue libraries. Note the nearly perfect correlation among the expression pattern of the CesA10, 11 and 12 genes.

EXAMPLE 9

This example describes a procedure to identify plants containing Mu inserted into genes of interest and a strategy to identify the function of those genes. This procedure was also described in U.S. patent application Ser. No. 09/371,383 which disclosed members of the same gene family as the present application. One of skill in the art could readily conceive of use of this procedure with the any of the Cellulose Synthase (CesA) sequences disclosed in the current application. The current example is based on work with the CesA11 gene, identified as SEQ ID NO: 27 herein.

The Trait Utility System for Corn (TUSC) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods that are designed to identify and isolate the gene(s) responsible for a particular trait (phenotype).

Pioneer Hi-Bred International, Inc., has a proprietary collection of maize genomic DNA from approximately 42,000 individual $F_1$ plants (Reverse genetics for maize, Meeley and Briggs, (1995) *Maize Genet. Coop. Newslett.* 69:67-82). The genome of each of these individuals contains multiple copies of the transposable element family, Mutator (Mu). The Mu family is highly mutagenic; in the presence of the active element Mu-DR, these elements transpose throughout the genome, inserting into genic regions, and often disrupting gene function. By collecting genomic DNA from a large number (42,000) of individuals, Pioneer has assembled a library of the mutagenized maize genome.

Mu insertion events are predominantly heterozygous; given the recessive nature of most insertional mutations, the $F_1$ plants appear wild-type. Each of the $F_1$ plants is selfed to produce $F_2$ seed, which is collected. In generating the $F_2$ progeny, insertional mutations segregate in a Mendelian fashion so are useful for investigating a mutant allele's effect on the phenotype. The TUSC system has been successfully used by a number of laboratories to identify the function of a variety of genes (Cloning and characterization of the maize An1 gene, Bensen, et al., (1995) *Plant Cell* 7:75-84; Diversification of C-function activity in maize flower development, Mena, et al., (1996) Science 274:1537-1540; Analysis of a chemical plant defense mechanism in grasses, Frey, et al., (1997) *Science* 277:696-699; The control of maize spikelet meristem fate by the APETALA2-like gene Indeterminate spikelet 1, Chuck, et al., (1998) *Genes and Development* 12:1145-1154; A SecY homologue is required for the elaboration of the chloroplast thylakoid membrane and for normal chloroplast gene expression, Roy and Barkan, (1998) *J. Cell Biol.* 141:1-11).

PCR Screening for Mu insertions in CesA11:

Two primers were designed from within the CesA11 cDNA and designated as gene-specific primers (GSPs):

```
Forward primer (GSP1/SEQ ID NO. 32):
5'-TACGATGAGTACGAGAGGTCCATGCTCA-3'

Reverse primer (GSP2/SEQ ID NO. 33):
5'-GGCAAAAGCCCAGATGCGAGATAGAC-3'

Mu TIR primer (SEQ ID NO. 34):
5'-AGAGAAGCCAACGCCAWCGCCTCYATTTCGTC-3'
```

Pickoligo was used to select primers for PCR. This program chooses the Tm according to the following equation:

$$Tm=[((GC*3+AT*2)*37-562)/\text{length}]-5$$

PCR reactions were run with an annealing temperature of 62° C. and a thermocycling profile as follows:

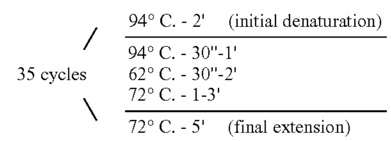

Gel electrophoresis of the PCR products confirmed that there was no false priming in single primer reactions and that only one fragment was amplified in paired GSP reactions.

The genomic DNA from 42,000 plants, combined into pools of 48 plants each, was subjected to PCR with either GSP1 or GSP2 and Mu TIR. The pools that were confirmed to be positive by dot-blot hybridization using CesA11 cDNA as a probe were subjected to gel-blot analysis in order to determine the size of fragments amplified. The pools in which clean fragments were identified were subjected to further analysis to identify the individual plants within those pools that contained Mu insertion(s).

Seed from $F_1$ plants identified in this manner was planted in the field. Leaf discs from twenty plants in each $F_2$ row were collected and genomic DNA was isolated. The same twenty plants were selfed and the $F_3$ seed saved. Pooled DNA (from 20 plants) from each of twelve rows was subjected to PCR using GSP1 or GSP2 and Mu TIR primer as mentioned above. Three pools identified to contain Mu insertions were subjected to individual plant analysis and homozygotes identified. The Mu insertion sites with the surrounding signature sequences are identified below:

```
Allele 1: 5'-TGGCGGCCG(SEQ ID NO: 35)-Mu-TCTGAAATG(SEQ ID NO: 36)-3'

Allele 2: 5'-GCCCACAAG(SEQ ID NO: 37)-Mu-CATCCTGGT(SEQ ID NO: 38)-3'

Allele 3: 5'-GTGTTCTTC(SEQ ID NO: 39)-Mu-GCCATGTGG(SEQ ID NO: 40)-3'
```

All three insertions are within 500 nucleotides of each other in the open reading frame, suggesting that this region in the gene might represent a hot spot for Mu insertion. One of the insertions, allele 1, is in the region upstream of the predicted six transmembrane domains near the C-terminal end of the protein. Each of these insertions is expected to inactivate the gene since they are all in the exonic regions of the gene.

EXAMPLE 10

This example describes the method used to measure mechanical strength of the maize stalks as well as the effect of the overexpression of different CesA genes on stalk strength. The mechanical strength of the mature corn stalks was measured with an electromechanical test system. The internodes below the ear were subjected to a 3-point bend test using an Instron, model 4411 (Instron Corporation, 100 Royall Street, Canton, Mass. 02021), with a span-width of 200 mm between the anchoring points and a speed of 200 mm/min of the $3^{rd}$ point attached to a load cell. For measuring rind puncture strength, a needle was mounted on the load cell of the Instron and the load taken to puncture the rind was used as a measure of rind puncture strength.

Figure 1:
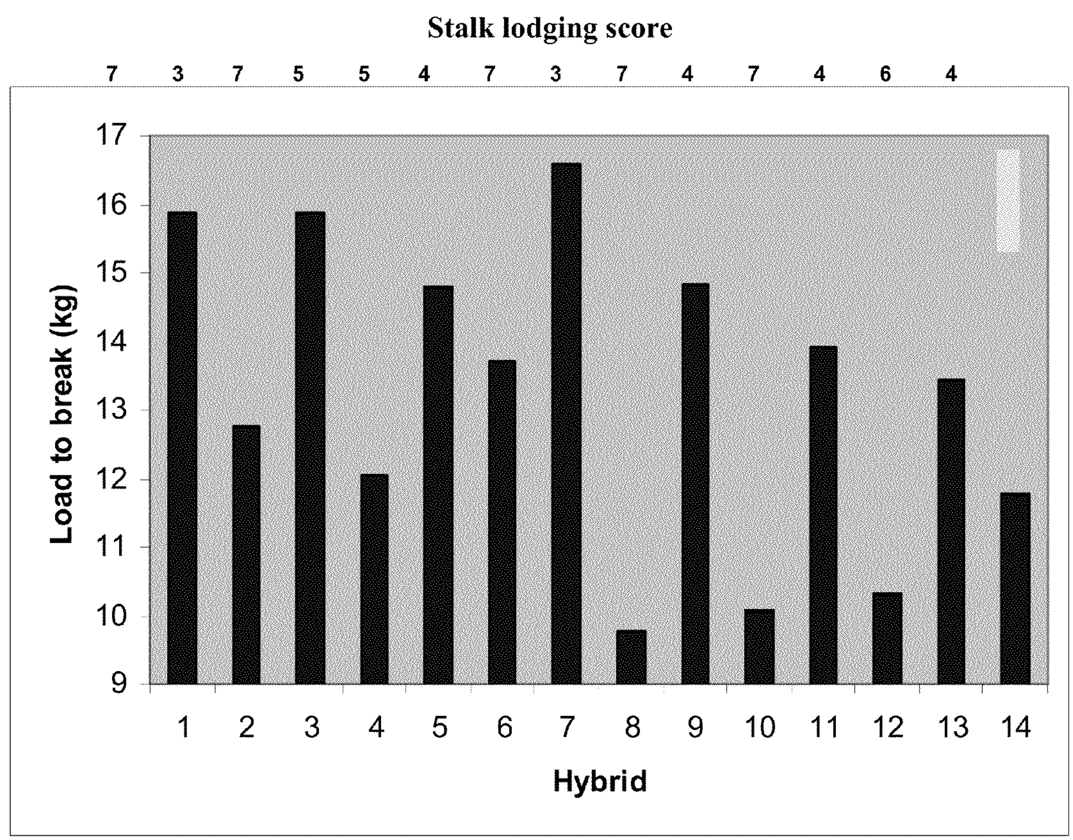
FIG. 1: Stalk breaking strength of hybrids and its comparison with the lodging scores. The mechanical strength is very similar to the lodging scores that have been assigned based on field observations. The vertical light-colored bar in the upper right corner of the figure is the least significant difference (LSD) estimate at 5% level.

Load needed to break the internode was used as a measure of mechanical strength. The internodes are stronger toward the base of the stalk. This mechanical stalk breaking strength or the "load to break" was used to classify the hybrids with known stalk characteristics into respective categories based on the internodal breaking strength. The load to break the internodal zone was very similar to the lodging score that had been assigned to the hybrids based on field observations (see, FIG. 1). Approximately 90% of the variation for internodal breaking strength was explained by unit stalk dry matter below the ear (47%), stalk diameter (30%) and rind puncture resistance (10%). Moisture levels above 30% in the stalk tissue masked the contribution of the rind tissue to breaking strength. The internodal breaking strength was highly correlated with the amount of cellulose per unit length of the stalk.

Four of the CesA genes were expressed under the control of a weak constitutive promoter, F3.7 (see, Coughlin, et al., U.S. patent application Ser. No. 09/387,720, filed Aug. 30, 1999). Table 4 discloses the construct numbers, corresponding sequence IDs from the patent, promoters, and the gene names. In2 is an inducible promoter from the In2 gene from maize. The In2 promoter responds to benzenesulfonamide herbicide safeners (see, Hershey, et al., (1991) *Mol. Gen. Genetics* 227:229-237 and Gatz, et al., (1994) *Mol. Gen Genetics* 243: 32-38).

TABLE 4

| Construct | CesA SEQ ID NO. | Promoter | Gene name |
|---|---|---|---|
| 1 | 1 | F3.7 | CesA1 |
| 2 | 9 | F3.7 | CesA4 |
| 3 | 13 | F3.7 | CesA5 |
| 4 | 17 | F3.7 | CesA8 |
| 5 | Control | IN2 | GUSINT |

Twenty-five individual $T_0$ events for each construct were generated in a hybrid maize background using *Agrobacterium*-mediated transformation. Data for various traits, such as plant height, stalk mass below ear, stalk diameter, internodal breaking strength and structural material and cellulose percentages in the internodal tissue were collected.

Figure 6:
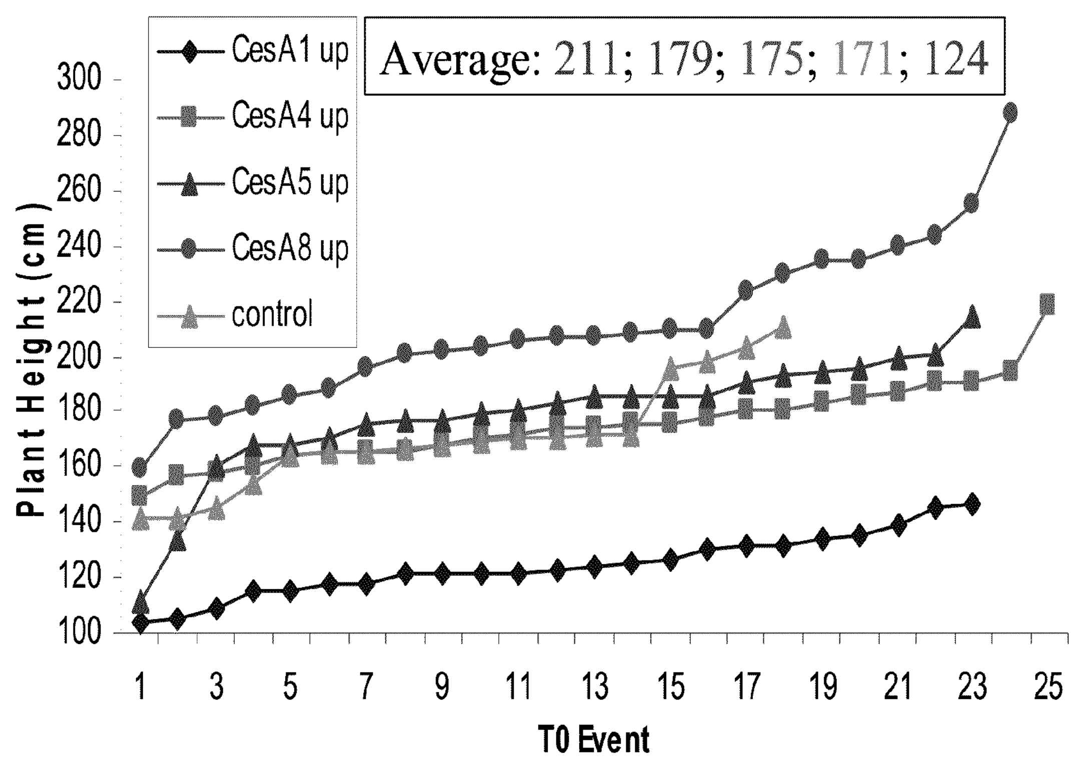
FIG. 6: Effect of overexpression of different CesA genes on plant height in corn. Whereas the overexpression of CesA8 led to an increase in height, CesA4 and CesA5 had not effect. Overexpression of CesA1 resulted in stunted plants.

The plants from the transgenic events generated using the CesA8 gene were significantly taller in comparison to the control plants containing a GUS gene. Interestingly, a reduction in height was observed when the CesA1 gene was introduced. The other two genes, CesA4 and CesA5, did not differ from the control plants. (See, FIG. 6.) It has long been known that cellulose synthase occurs as a terminal rosette complex consisting of multiple functional cellulose synthase polypeptides that are organized in a ring with a hexagonal symmetry. Each of the six members of the ring is believed to contain six or more functional enzyme units. In general, 36 or more cellulose chains are extruded simultaneous to their synthesis through the plasma membrane into the apoplast. These chains are crystallized into a microfibril right as they come in contact with each other after extrusion through the rosette complex. A functional cellulose synthase is believed to consist of two polypeptides derived form different CesA genes, forming a heterodimer, resulting in a total of 72 or more CesA polypeptides in each rosette.

While not intending to be limited to a single theory, it is possible that a homodimer could also form a functional enzyme. Therefore, the possible reasons for a reduction in plant height in the events where CesA1 was overexpressed are: 1) the other CesA gene with which its polypeptide forms a heterodimer is down-regulated and 2) the expression of the other gene is not affected but the CESA1 homodimer forms a nonfunctional enzyme, in which case the functional dimers are competed out of the rosette complex. In the latter case, the overexpressed gene behaves as a dominant repressor of cellulose synthesis. This should manifest in the form of microfibrils with fewer cellulose chains. This could be detected by some physical techniques such as differential scanning calorimetry (DSC). The reverse could be true for the CesA8 gene whose homodimers may be functional, and/or whose overexpression might induce the expression of its partner gene the product of which it uses to make a functional enzyme. The fact that an increase in height is observed may result from stalk becoming an active sink when CesA8 is overexpressed. Stalk is usually considered to be a passive sink which cannot compete well with the developing ear. This argument is supported by the observation that the plants containing CesA8 as a transgene had smaller ears.

Figure 3:
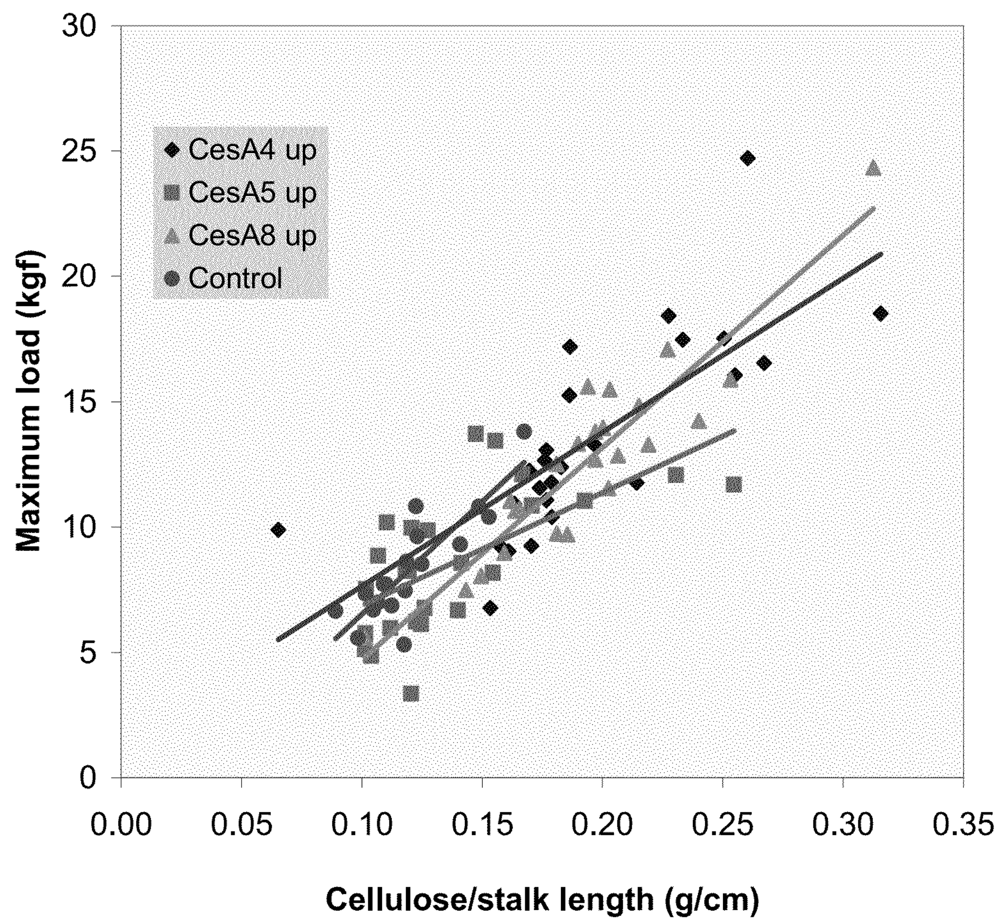
FIG. 3: Correlation between unit cellulose and stalk breaking strength. Stalk breaking strength was highly correlated with the amount of cellulose in a unit stalk length (correlation coefficient, r: 0.76; 0.63; 0.92; 0.86.) While these correlations are specifically related to the different CesA genes, it should be noted that in general the same correlation would apply. In other words, it is expected this would apply to low cellulose levels as well as higher cellulose levels.
Figure 7:
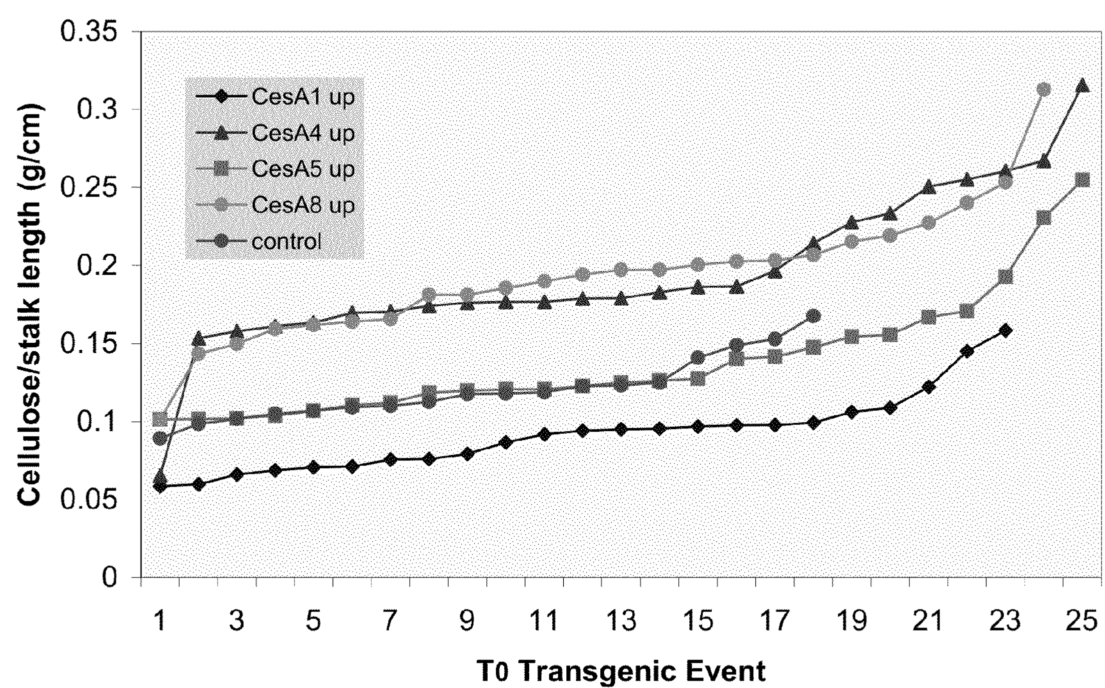
FIG. 7: Effect of the overexpression of different CesA genes on the amount of cellulose in a unit length of the stalk tissue below ear in corn. CesA4 and CesA8, when overexpressed, resulted in an increased cellulose/length, CesA5 had no effect and CesA1 resulted in reduced cellulose/length.

Cellulose content and stalk length below the ear is highly correlated with the breaking strength of the stalk (see, FIG. 3). An increase in cellulose production can be accommodated by the following alterations: 1) synthesis of the other cell wall constituents stays constant, leading to an increased cellulose percentage in the wall and 2) increase in cellulose synthesis upregulates the synthesis of the other cell wall constituents as well, in which case the percentage of cellulose does not change in the wall but the amount of cellulose in a unit length does. Two of the CesA genes, CesA4 and CesA8, showed an increase in the amount of cellulose in a unit length of the stalk below the ear (see, FIG. 7). One of the genes, CesA5, did not have any effect on the amount of cellulose in the stalk. It was recently suggested, based on its expression pattern in different tissues, that CesA5 might actually be involved in the formation of some non-cellulosic polysaccharide, most probably mixed-linked glucan (Dhugga, (2001) *Curr. Opin. Plant Biol.* 4:488-493). The data in the accompanying figure seem to support this argument.

Figure 2:
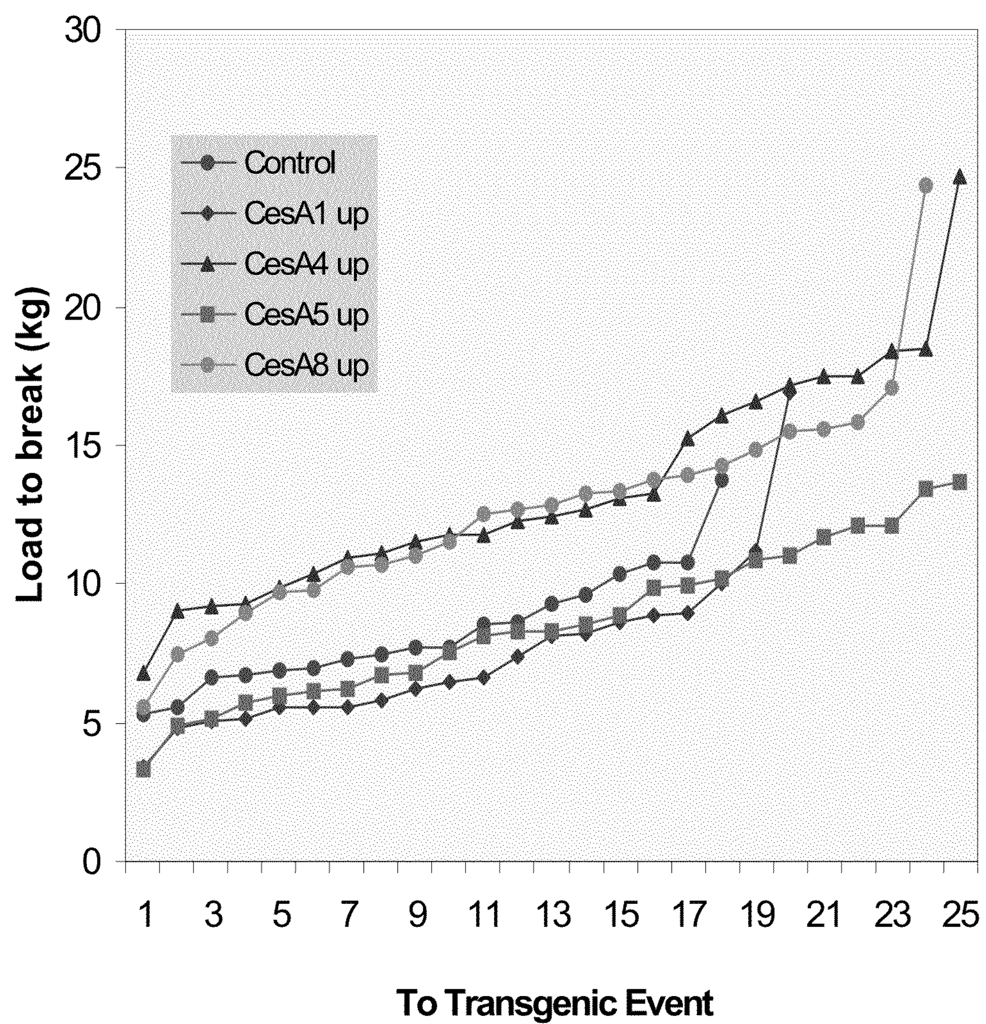
FIG. 2: Stalk strength of $T_0$ transgenic plants. Plants overexpressing ("up") ZmCesA4 and ZmCesA8 had significantly stronger stalks than the controls. Overexpression of CesA5 did not alter stalk strength whereas the overexpression of CesA1 led to weaker and stunted stalks.

The internodes were subjected to breakage with a 3-point Instron and the load to break plotted as a function of unit cellulose amount. (See, FIG. 2.) A high correlation between these two traits is observed from the multiple events, particularly for CesA8 (FIG. 3). We have found from other studies that this gene is involved in cellulose synthesis in the vascular bundles in the elongating cells (Holland, et al., (2000) *Plant Physiol.* 123:1313-1323). These data support our previous observations and supports the observation that the amount of cellulose in a unit length of stalk below the ear results in an increased stalk strength.

EXAMPLE 11

This example describes the method used to overexpress CesA genes which will increase the quality of harvested stover, leading to an increase in ethanol yield per unit stover.

Transgenic plants expressing the Ces A gene of interest could be produced by the method outlined in Example 5 or other suitable methods. These plants containing increased quantities of cellulose would then be used to produce higher quality stover.

The following is an example of the applications of the present invention in applications of ethanol biorefineries. In addition the cellulose biosynthetic pathway's role as primary determinant of tissue strength, a trait that is of significant interest in agriculture, where cellulose constitutes the most abundant renewable energy resource. More than 200 million metric tons of stover is produced just from maize in the United States every year. About one-third of this could potentially be utilized in ethanol biorefineries (Kadam and McMillan, 2003). The worldwide production of lignocellulosic wastes from cereal stover and straw is estimated to be ~3 billion tons per year (Kuhad and Singh, 1993). Stover material containing higher amounts of cellulose and lower amounts of lignin is expected to increase ethanol production in the biorefineries. Lignin is a target for reduction because it is an undesirable constituent in paper industry as well as in silage digestibility (Hu, et al., 1999; Li, et al., 2003).

Corn stover alone offers a significant target as a feedstock for the ethanol biorefineries (see, the World Wide Web at ctic.purdue.edu/Core4/ctic-dc.ppt; and bioproducts-bioenergy.gov/pdfs/bcota/abstracts/31/z263.pdf.) Aside from its use in biorefineries, it can substitute hardwood fiber for paper production. With rapid progress being made in streamlining the process of fermentation of stover material and increasing cost of imported oil, corn stover is expected to become a key feedstock in ethanol and paper production (Wheals, et al., 1999; Atistidou and Penttila, 2000). In addition to supplying 5-8 billion gallons of ethanol per year with no additional land use, it is expected to contribute to an annual farm income of $2.3 billion and reduce the greenhouse gases by 60-95 million metric tons, which is 12-20% of the US-Kyoto commitment (see, the World Wide Web at ctic.purdue.edu/Core4/ctic-dc.ppt; and bioproducts-bioenergy.gov/pdfs/bcota/abstracts/31/z263.pdf). Ethanol combustion results in carbon dioxide and water, the same molecules plant primarily uses to make biomass.

The concern about there being an effect on the soil organic matter by the removal of the aboveground biomass is mitigated by the findings that over a 30-year period, no significant difference was observed in the soil organic matter between a field where the aboveground stover was removed for silage and the one where the stover was ploughed into the ground after grain harvest. Most of the ploughed stover is lost as carbon dioxide into the atmosphere.

During pretreatment of the corn stover for enzymatic digestion, the soluble sugars are discarded. Also, pentose sugars are not as well fermented as the hexose sugars despite the progress made in the fermentation process, which involves using *Zymomonas* bacteria instead of the traditional yeast (Atistidou and Penttila, 2000; Badger, 2002). The polysaccharide fraction of the corn stalk contains ~20% pentose sugars, the remainder being hexose sugars (Dhugga, unpublished). Also, the free sugar concentration ranges from 4-12%. Lignin content averages ~19% and ranges from 18-23%. By overexpressing the CesA genes of the present invention, the free sugars can be converted into polymeric (cellulosic) form, which will increase ethanol yield per unit of the harvested stover. The claimed invention also teaches an increase cellulose at the expense of pentose-containing polymers (e.g., arabinoxylan) and lignin.

EXAMPLE 12

This example discusses the application of CesA genes in late season stalk strength.

Stalk lodging results in significant yield losses in crop plants, particularly in cereals (Duvick and Cassman, 1999). Stalk standability is dependent upon the amount of dry matter per unit length of the stalk and is thus a function of resource partitioning and allocation. Harvest index, the ratio of the grain to total aboveground biomass, is an indicator of dry matter partitioning efficiency. It has remained around 50% for over a hundred years in maize (Sinclair, 1998). In comparison to maize, harvest index acquired a different role in increasing plant standability in small grain cereals where it was significantly increased with the introduction of dwarfing genes. Reduced stature made these cereals less likely to lodge by reducing torque on the top-heavy straw, which allowed for higher inputs such as fertilizers and irrigation, resulting in increased biomass production per unit land area. Whereas yield increases in small grain cereals have resulted from an increase in both harvest index and total biomass production per unit land area, those in maize have been the consequence of mainly an increase in total biomass. Increased planting density as a means of increasing grain yield in maize has affected changes in leaf angle and shape as adaptations to this environment and has in general resulted in increased plant and ear heights (Duvick and Cassman, 1999). The stalk becomes mechanically weaker with increasing planting density because of reduction in individual plant vigor that results from a nonlinear relationship between planting density and biomass increase.

Figure 8:
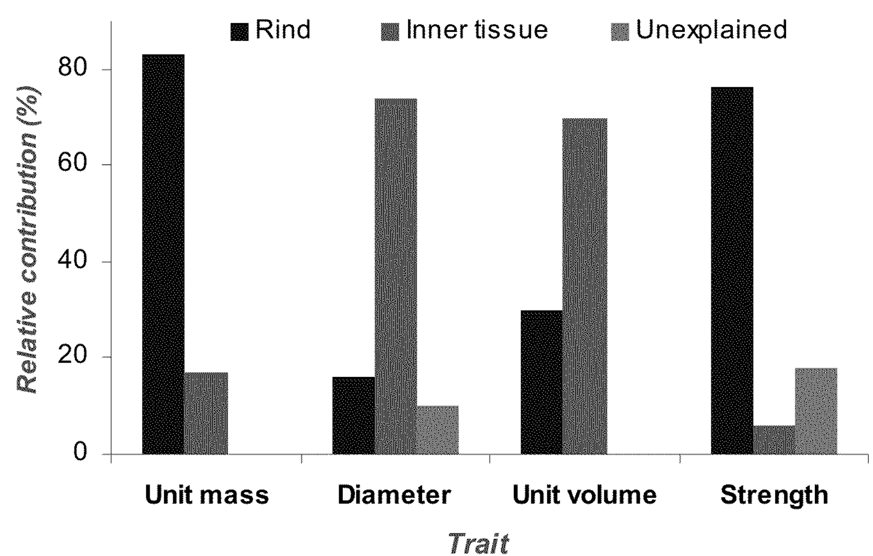
FIG. 8: Contribution of different stalk components to dry matter, diameter, volume and stalk strength in maize hybrids. The data are derived from seven hybrids grown at three densities (27, 43 and 59 K per acre) in three replications each in 2001. Two stalks were sampled from each replication. Internodes 3 and 4 below the ear were broken with Instron model 4411 (Instron Corporation, 100 Royall Street, Canton, Mass. 02021). After breaking, the 3rd internode was separated into rind and inner tissue. Path coefficient analyses were performed using rind and inner tissue as independent variables ($X_1$ and $X_2$, respectively) and the whole stalk as the dependent variable (Y). The multiple regression equation: $Y=a+b_1X_1+b_2X_2+e$ where a is the intercept and e error. Path coefficients were calculated as follows: $\rho_{YXn}=b_n*\delta_n/\delta_Y$ where n is 1 or 2. The contribution of each independent variable to whole stalk (Y) was calculated as follows: $\rho_{Yxn}*r_{Yxn}$ where r is the correlation coefficient.

The understanding that cellulose in a unit length of the stalk is indeed the main determinant of mechanical strength had been proposed. (Appenzeller, et al., 2004). Most of the dry matter and thus cellulose in the stalk is concentrated in the outer layers, collectively referred to as rind, which is composed of densely packed vascular bundles. Vascular bundles are surrounded by sclerenchymatous cells. Although vascular bundles are also sparsely distributed in the internal tissue, a great majority of them are present in the outer layers as judged from the dry matter distribution (FIG. 8). FIG. 8 describes the contribution of different stalk components to dry matter, diameter, volume and stalk strength in maize hybrids. The data are derived from seven hybrids grown at three densities (27, 43 and 59 K per acre) in three replications each in 2001. Two stalks were sampled from each replication. Internodes 3 and 4 below the ear were broken with Instron. After breaking, the 3rd internode was separated into rind and inner tissue. Path coefficient analyses were performed using rind and inner tissue as independent variables ($X_1$ and $X_2$, respectively) and the whole stalk as the dependent variable (Y). The multiple regression equation: $Y=a+b_1X_1+b_2X_2+e$ where a is the intercept and e error. Path coefficients were calculated as follows: $\rho_{YXn}=b_n*\delta_n/\delta_Y$ where n is 1 or 2. The contribution of each independent variable to whole stalk (Y) was calculated as follows: $\rho_{Yxn}*r_{Yxn}$ where r is the correlation coefficient. Note: the unexplained variation for diameter is attributable to the corn stalk not being perfectly round and the difficulty thus associated with determining the cross-sectional area accurately. Some other variable, like size and number of vascular bundles and their density, may account for the remaining variation in strength. The introduced transgene, by removing the limitation of the particular step it encodes the enzyme for catalyzing, may either lead to an increase in the percentage of that particular polysaccharide (composition changed) or of the whole cell wall (composition not changed). In the latter case, the additional dry matter could be accommodated in enlarged vascular bundles which could, in turn, result in an increased diameter.

Isolation of genes that affect cellulose formation has made it possible to test their respective roles in stalk strength by transgenic and reverse genetics approaches (Appenzeller, et al., 2004). Transgenic plants expressing the Ces A gene of interest are produced by the method outlined in Example 5 or other suitable methods. Expression of the cellulose synthase gene is measuredThree of the twelve cellulose synthase genes are preferentially expressed in the secondary wall-forming cells (Appenzeller, et al., 2004). Whereas two of these genes, CesA10 and CesA11, are expressed more highly in the vascular bundles, CesA12 appears to be more highly expressed in the surrounding, sclerenchymatous cells (Appenzeller, et al., 2004). Overexpression of the three CesA genes individually and in combinations is used to increase cellulose production in the rind cells as well as the internal tissue cells. Internal tissue cells, as shown in FIG. 8, account for a majority of the volume but only a small amount of biomass and thus offer suitable targets for making more cellulose. Isolated promoters for each of these genes are used to drive the expression of these genes in different cell types. In addition, promoters from other genes can be used to express the CesA genes in other cell types.

EXAMPLE 13

This example discusses the application of the CesA genes in improving nodal strength to reduce mid-season green snap.

Mid-season green snap is a significant problem in the Western plains, e.g., Nebraska, North and South Dakota and Western Minnesota, whereby the stalk snaps at the nodal plate before flowering in a severe windstorm at or below the ear node, resulting in yield losses of up to 80%. The underlying reason for this lesion is the disparity in the rates of elongation growth and dry matter deposition in the corn plant before flowering. Whereas a plant doubles in height in approximately two weeks before flowering, the most rapid rate of elongation growth, it accumulates only 30% additional dry matter during the same period, resulting in a 3-fold disparity (Dhugga, unpublished data). The plant thus becomes susceptible to breakage. It has been determined that the breakage occurs through the pulvinal zone at the base of the leaf sheath.

Figure 9:
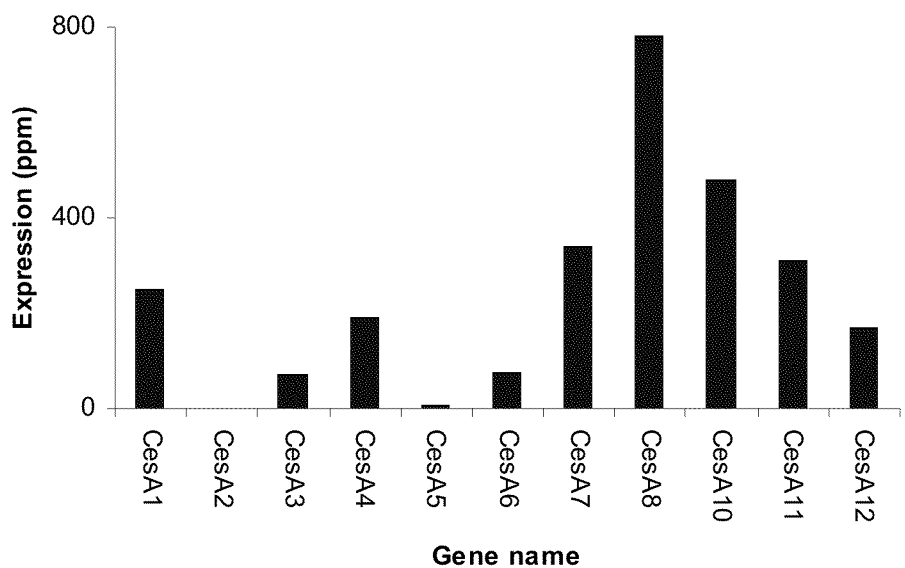
FIG. 9: Expression of the maize CesA genes in the pulvinal tissue of leaf derived from an elongating internode. The expression was studied by the Lynx MPSS technology.

Transgenic plants expressing the Ces A genes are produced by the method outlined in Example 5 or other suitable methods. The expression pattern of eleven of the twelve maize CesA genes in the pulvinal zone tissue is shown in FIG. 9. The twelfth, CesA9, had the same tag at CesA4 to which it is very highly related. Seven of the genes, CesA1, 4, 7, 8, 10, 11 and 12 are expressed at a higher level than the remaining genes. CesA8 shows the highest expression in this tissue. The expression of the various CesA genes, particularly CesA8, in this tissue can be used to increase its strength.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. A cellulose synthase product derived from the method of processing of plant tissues expressing an isolated polynucleotide encoding a functional cellulose synthase, the method comprising:

a) transforming a plant cell with a recombinant expression cassette comprising a polynucleotide having at least 90% sequence identity to the full length sequence of a polynucleotide selected from the group consisting of SEQ ID NO: 21, operably linked to a promoter; and b) culturing the transformed plant cell under plant cell growing conditions; wherein the level of cellulose synthase in said transformed plant cell is modulated;

c) growing the plant cell under plant-forming conditions to express the polynucleotide in the plant tissue; and d) processing the plant tissue to obtain a cellulose synthase product.

2. An isolated cellulose synthase product obtained from a transformed plant cell expressing an isolated polynucleotide that encodes a functional cellulose synthase polypeptide consisting of SEQ ID NO: 22.

3. The cellulose synthase product according to claim 1, wherein the transformed plant cell is a monocot cell.

4. The cellulose synthase product of claim 1, wherein the plant cell is selected from the group consisting of: maize, soybean, sunflower, sorghum, canola, wheat, alfalfa, cotton, rice, barley and millet.

5. The cellulose synthase product according to claim 1, which improves stalk strength of a plant by overexpression of the polynucleotide.

6. The cellulose synthase product according to claim 1, which reduces green snap by improving nodal strength.

7. The cellulose synthase product according to claim 1, which is a constituent of ethanol.

* * * * *

SEQUENCE LISTING

```
<160> NUMBER OF SEQ ID NOS: 52

<210> SEQ ID NO 1
<211> LENGTH: 3780
<212> TYPE: DNA
<213> ORGANISM: Zea mays

<400> SEQUENCE: 1

gtcgacccac gcgtccgcag cagcagaagc actgcgcggc attgcagcga tcgagcggga      60

ggaatttggg gcatggtggt cgccaacgcc gctcggatct agaggcccgc acgggccgat     120

tggtctccgc ccgcctcgtc ggtgttggtg tcgttggcgt gtggagccgt ctcggtggga     180

gcagcgggga gggagcggag atggcggcca acaaggggat ggtggcgggc tcgcacaacc     240

gcaacgagtt cgtcatgatc cgccacgacg gcgatgtgcc gggctcggct aagcccacaa     300

agagtgcgaa tggacaggtc tgccagattt gcggtgactc tgtgggtgtt tcagccactg     360

gtgatgtctt tgttgcctgc aatgagtgtg ccttccctgt ctgccgccca tgctatgagt     420

atgagcgcaa ggaggggaac caatgctgcc cccagtgcaa gactagatac aagagacaga     480

aaggtagccc tcgagttcat ggtgatgagg atgaggaaga tgttgatgac ctagacaatg     540

aattcaacta caagcaaggc agtgggaaag gcccagagtg gcaactgcaa ggagatgatg     600

ctgatctgtc ttcatctgct cgccatgagc cacatcatcg gattccacgc ctgacaagcg     660

gtcaacagat atctggagag attcctgatg cttcccctga ccgtcattct atccgcagtc     720

caacatcgag ctatgttgat ccaagcgtcc cagttcctgt gaggattgtg gacccctcga     780
```

```
aggacttgaa ttcctatggg cttaatagtg ttgactggaa ggaaagagtt gagagctgga    840
gggttaaaca ggacaaaaat atgatgcaag tgactaataa atatccagag gctagaggag    900
gagacatgga ggggactggc tcaaatggag aagatatgca aatggttgat gatgcacggc    960
tacctttgag ccgtatcgtg ccaatttcct caaaccagct caacctttac cgggtagtga   1020
tcattctccg tcttatcatc ctgtgcttct tcttccagta tcgtgtcagt catccagtgc   1080
gtgatgctta tggattatgg ctagtatctg ttatctgcga ggtctggttt gccttgtctt   1140
ggcttctaga tcagttccca aaatggtatc caatcaaccg tgagacatat cttgacaggc   1200
ttgcattgag gtatgataga gagggagagc catcacagct ggctcccatt gatgtcttcg   1260
tcagtacagt ggatccattg aaggaacctc cactgatcac agccaacact gttttgtcca   1320
ttctttctgt ggattaccct gttgacaaag tgtcatgcta tgtttctgat gatggttcag   1380
ctatgctgac ttttgagtct ctctcagaaa ccgcagaatt tgctagaaag tgggttccct   1440
tttgtaagaa gcacaatatt gaaccaagag ctccagaatt ttactttgct caaaaaatag   1500
attacctgaa ggacaaaatt caaccttcat ttgttaagga aagacgcgca atgaagaggg   1560
agtatgaaga attcaaagta agaatcaatg cccttgttgc caaagcacag aaagtgcctg   1620
aagaggggtg gaccatggct gatggaactg catggcctgg gaataatcct agggaccatc   1680
ctggcatgat tcaggttttc ttggggcaca gtggtgggct cgacactgat ggaaatgagt   1740
taccacgtct tgtctatgtc tctcgtgaaa agagaccagg ctttcagcat cacaagaagg   1800
ctggtgcaat gaatgcgctg attcgtgtat ctgctgtgct gacaaatggt gcctatcttc   1860
tcaatgtgga ttgcgaccat tacttcaata gcagcaaagc tcttagagaa gcaatgtgct   1920
tcatgatgga tccggctcta ggaaggaaaa cttgttatgt acaatttcca cagagatttg   1980
atggcattga cttgcacgat cgatatgcta atcggaacat agttttcttt gatatcaaca   2040
tgaaaggtct ggatggcatt cagggtccag tttacgtggg aacaggatgc tgtttcaata   2100
gacaggcttt gtatggatac gatcctgttt tgactgaagc tgatctggag ccaaacattg   2160
ttattaagag ctgctgtggt agaaggaaga aaaagaacaa gagttatatg gatagtcaaa   2220
gccgtattat gaagagaaca gaatcttcag ctcccatctt caatatggaa gacatcgaag   2280
agggtattga aggttacgag gatgaaaggt cagtgcttat gtcccagagg aaattggaga   2340
aacgctttgg tcagtctcct attttcattg catccacctt tatgacacaa ggtggcatac   2400
caccttcaac aaacccagct tctctactaa aggaagctat ccatgtcatc agttgtggat   2460
atgaggacaa aactgaatgg ggaaaagaga ttggctggat ctatggttca gtaacggagg   2520
atattctgac tgggtttaaa atgcatgcaa ggggctggca atcaatctac tgcatgccac   2580
cacgaccttg tttcaagggt tctgcaccaa tcaatctttc cgatcgtctt aatcaggtgc   2640
tccgttgggc tcttgggtca gtggaaattc tgcttagtag acattgtcct atctggtatg   2700
gttacaatgg acgattgaag cttttggaga ggctggctta catcaacact attgtatatc   2760
caatcacatc cattccgctt attgcctatt gtgtgcttcc cgctatctgc ctccttacca   2820
ataaatttat cattcctgag attagcaatt atgctgggat gttcttcatt cttcttttcg   2880
cctccatttt tgccactggt atattggagc ttagatggag tggtgttggc attgaagatt   2940
ggtggagaaa tgagcagttt tgggttattg gtggcacctc tgcccatctc ttcgcagtgt   3000
tccagggtct gctgaaagtg ttggctggga ttgataccaa cttcacagtt acctcaaagg   3060
catctgatga ggatggcgac tttgctgagc tatatgtgtt caagtggacc agtttgctca   3120
ttcctccgac cactgttctt gtcattaacc tggtcggaat ggtggcagga atttcttatg   3180
```

```
ccattaacag tggctaccaa tcctggggtc cgctctttgg aaagctgttc ttctcgatct   3240

gggtgatcct ccatctctac cccttcctca agggtctcat gggaaggcag aaccgcacac   3300

caacaatcgt cattgtctgg tccatccttc ttgcatctat cttctccttg ctgtgggtga   3360

agatcgatcc tttcatctcc ccgacacaga aagctgctgc cttggggcaa tgtggcgtca   3420

actgctgatc gagacagtga ctcttatttg aagaggctca atcaagatct gccccctcgt   3480

gtaaatacct gaggaggcta gatgggaatt ccttttgttg taggtgagga tggatttgca   3540

tctaagttat gcctctgttc attagcttct tccgtgccgg tgctgctgcg gactaagaat   3600

cacggagcct ttctaccttc catgtagcgc cagccagcag cgtaagatgt gaattttgaa   3660

gttttgttat gcgtgcagtt tattgtttta gagtaaatta tcatttgttt gtgggaactg   3720

ttcacacgag cttataatgg caatgctgtt atttaaaaaa aaaaaaaaaa gggcggccgc   3780
```

<210> SEQ ID NO 2
<211> LENGTH: 1075
<212> TYPE: PRT
<213> ORGANISM: Zea mays

<400> SEQUENCE: 2

```
Met Ala Ala Asn Lys Gly Met Val Ala Gly Ser His Asn Arg Asn Glu
 1               5                  10                  15

Phe Val Met Ile Arg His Asp Gly Asp Val Pro Gly Ser Ala Lys Pro
            20                  25                  30

Thr Lys Ser Ala Asn Gly Gln Val Cys Gln Ile Cys Gly Asp Ser Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Glu Asp Glu Glu Asp Val Asp Asp Leu Asp
            100                 105                 110

Asn Glu Phe Asn Tyr Lys Gln Gly Ser Gly Lys Gly Pro Glu Trp Gln
        115                 120                 125

Leu Gln Gly Asp Asp Ala Asp Leu Ser Ser Ser Ala Arg His Glu Pro
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Met Gln Val
    210                 215                 220

Thr Asn Lys Tyr Pro Glu Ala Arg Gly Gly Asp Met Glu Gly Thr Gly
225                 230                 235                 240

Ser Asn Gly Glu Asp Met Gln Met Val Asp Asp Ala Arg Leu Pro Leu
                245                 250                 255

Ser Arg Ile Val Pro Ile Ser Ser Asn Gln Leu Asn Leu Tyr Arg Val
            260                 265                 270
```

```
Val Ile Ile Leu Arg Leu Ile Ile Leu Cys Phe Phe Phe Gln Tyr Arg
        275                 280                 285

Val Ser His Pro Val Arg Asp Ala Tyr Gly Leu Trp Leu Val Ser Val
    290                 295                 300

Ile Cys Glu Val Trp Phe Ala Leu Ser Trp Leu Leu Asp Gln Phe Pro
305                 310                 315                 320

Lys Trp Tyr Pro Ile Asn Arg Glu Thr Tyr Leu Asp Arg Leu Ala Leu
                325                 330                 335

Arg Tyr Asp Arg Glu Gly Glu Pro Ser Gln Leu Ala Pro Ile Asp Val
            340                 345                 350

Phe Val Ser Thr Val Asp Pro Leu Lys Glu Pro Pro Leu Ile Thr Ala
        355                 360                 365

Asn Thr Val Leu Ser Ile Leu Ser Val Asp Tyr Pro Val Asp Lys Val
    370                 375                 380

Ser Cys Tyr Val Ser Asp Asp Gly Ser Ala Met Leu Thr Phe Glu Ser
385                 390                 395                 400

Leu Ser Glu Thr Ala Glu Phe Ala Arg Lys Trp Val Pro Phe Cys Lys
                405                 410                 415

Lys His Asn Ile Glu Pro Arg Ala Pro Glu Phe Tyr Phe Ala Gln Lys
            420                 425                 430

Ile Asp Tyr Leu Lys Asp Lys Ile Gln Pro Ser Phe Val Lys Glu Arg
        435                 440                 445

Arg Ala Met Lys Arg Glu Tyr Glu Glu Phe Lys Val Arg Ile Asn Ala
    450                 455                 460

Leu Val Ala Lys Ala Gln Lys Val Pro Glu Glu Gly Trp Thr Met Ala
465                 470                 475                 480

Asp Gly Thr Ala Trp Pro Gly Asn Asn Pro Arg Asp His Pro Gly Met
                485                 490                 495

Ile Gln Val Phe Leu Gly His Ser Gly Gly Leu Asp Thr Asp Gly Asn
            500                 505                 510

Glu Leu Pro Arg Leu Val Tyr Val Ser Arg Glu Lys Arg Pro Gly Phe
        515                 520                 525

Gln His His Lys Lys Ala Gly Ala Met Asn Ala Leu Ile Arg Val Ser
    530                 535                 540

Ala Val Leu Thr Asn Gly Ala Tyr Leu Leu Asn Val Asp Cys Asp His
545                 550                 555                 560

Tyr Phe Asn Ser Ser Lys Ala Leu Arg Glu Ala Met Cys Phe Met Met
                565                 570                 575

Asp Pro Ala Leu Gly Arg Lys Thr Cys Tyr Val Gln Phe Pro Gln Arg
            580                 585                 590

Phe Asp Gly Ile Asp Leu His Asp Arg Tyr Ala Asn Arg Asn Ile Val
        595                 600                 605

Phe Phe Asp Ile Asn Met Lys Gly Leu Asp Gly Ile Gln Gly Pro Val
    610                 615                 620

Tyr Val Gly Thr Gly Cys Cys Phe Asn Arg Gln Ala Leu Tyr Gly Tyr
625                 630                 635                 640

Asp Pro Val Leu Thr Glu Ala Asp Leu Glu Pro Asn Ile Val Ile Lys
                645                 650                 655

Ser Cys Cys Gly Arg Arg Lys Lys Lys Asn Lys Ser Tyr Met Asp Ser
            660                 665                 670

Gln Ser Arg Ile Met Lys Arg Thr Glu Ser Ser Ala Pro Ile Phe Asn
        675                 680                 685

Met Glu Asp Ile Glu Glu Gly Ile Glu Gly Tyr Glu Asp Glu Arg Ser
    690                 695                 700
```

```
Val Leu Met Ser Gln Arg Lys Leu Glu Lys Arg Phe Gly Gln Ser Pro
705                 710                 715                 720

Ile Phe Ile Ala Ser Thr Phe Met Thr Gln Gly Gly Ile Pro Pro Ser
                725                 730                 735

Thr Asn Pro Ala Ser Leu Leu Lys Glu Ala Ile His Val Ile Ser Cys
            740                 745                 750

Gly Tyr Glu Asp Lys Thr Glu Trp Gly Lys Glu Ile Gly Trp Ile Tyr
        755                 760                 765

Gly Ser Val Thr Glu Asp Ile Leu Thr Gly Phe Lys Met His Ala Arg
    770                 775                 780

Gly Trp Gln Ser Ile Tyr Cys Met Pro Pro Arg Pro Cys Phe Lys Gly
785                 790                 795                 800

Ser Ala Pro Ile Asn Leu Ser Asp Arg Leu Asn Gln Val Leu Arg Trp
                805                 810                 815

Ala Leu Gly Ser Val Glu Ile Leu Leu Ser Arg His Cys Pro Ile Trp
            820                 825                 830

Tyr Gly Tyr Asn Gly Arg Leu Lys Leu Leu Glu Arg Leu Ala Tyr Ile
        835                 840                 845

Asn Thr Ile Val Tyr Pro Ile Thr Ser Ile Pro Leu Ile Ala Tyr Cys
    850                 855                 860

Val Leu Pro Ala Ile Cys Leu Leu Thr Asn Lys Phe Ile Ile Pro Glu
865                 870                 875                 880

Ile Ser Asn Tyr Ala Gly Met Phe Phe Ile Leu Leu Phe Ala Ser Ile
                885                 890                 895

Phe Ala Thr Gly Ile Leu Glu Leu Arg Trp Ser Gly Val Gly Ile Glu
            900                 905                 910

Asp Trp Trp Arg Asn Glu Gln Phe Trp Val Ile Gly Gly Thr Ser Ala
        915                 920                 925

His Leu Phe Ala Val Phe Gln Gly Leu Leu Lys Val Leu Ala Gly Ile
    930                 935                 940

Asp Thr Asn Phe Thr Val Thr Ser Lys Ala Ser Asp Glu Asp Gly Asp
945                 950                 955                 960

Phe Ala Glu Leu Tyr Val Phe Lys Trp Thr Ser Leu Leu Ile Pro Pro
                965                 970                 975

Thr Thr Val Leu Val Ile Asn Leu Val Gly Met Val Ala Gly Ile Ser
            980                 985                 990

Tyr Ala Ile Asn Ser Gly Tyr Gln Ser Trp Gly Pro Leu Phe Gly Lys
        995                 1000                1005

Leu Phe Phe Ser Ile Trp Val Ile Leu His Leu Tyr Pro Phe Leu Lys
    1010                1015                1020

Gly Leu Met Gly Arg Gln Asn Arg Thr Pro Thr Ile Val Ile Val Trp
1025                1030                1035                1040

Ser Ile Leu Leu Ala Ser Ile Phe Ser Leu Leu Trp Val Lys Ile Asp
                1045                1050                1055

Pro Phe Ile Ser Pro Thr Gln Lys Ala Ala Ala Leu Gly Gln Cys Gly
            1060                1065                1070

Val Asn Cys
        1075
```

<210> SEQ ID NO 3
<211> LENGTH: 25
<212> TYPE: DNA
<213> ORGANISM: Zea mays

<400> SEQUENCE: 3
atggcggcca acaaggggat ggtgg 25

<210> SEQ ID NO 4
<211> LENGTH: 25
<212> TYPE: DNA
<213> ORGANISM: Zea mays

<400> SEQUENCE: 4
tcagcagttg acgccacatt gcccc 25

<210> SEQ ID NO 5
<211> LENGTH: 2830
<212> TYPE: DNA
<213> ORGANISM: Zea mays
<220> FEATURE:
<221> NAME/KEY: misc_feature
<222> LOCATION: 2809, 2818, 2824, 2826, 2829
<223> OTHER INFORMATION: n = A,T,C or G
<221> NAME/KEY: misc_feature
<222> LOCATION: 2809, 2818, 2824, 2826, 2829
<223> OTHER INFORMATION: n = A,T,C or G

<400> SEQUENCE: 5
tacctctaag tcgcatagtt ccgatatctc caaacgagct taacctttat cggatcgtga 60
ttgttctccg gcttatcatc ctatgtttct tctttcaata tcgtataact catccagtgg 120
aagatgctta tgggttgtgg cttgtatctg ttatttgtga agtttggttt gccttgtctt 180
ggcttctaga tcagttccca aagtggtatc ctatcaaccg tgaaacttac ctcgatagac 240
ttgcattgag atatgatagg gagggtgagc catcccagtt ggctccaatc gatgtctttg 300
ttagtacagt ggatccactt aaggaacctc ctctaattac tggcaacact gtcctgtcca 360
ttcttgctgt ggattaccct gttgacaaag tatcatgtta tgtttctgat gacggttcag 420
ctatgttgac ttttgaagcg ctatctgaaa ccgcagagtt tgcaaggaaa tgggttccct 480
tttgcaagaa acacaatatt gaacctaggg ctccagagtt ttactttgct cgaaagatag 540
attacctaaa ggacaaaata caaccttctt ttgtgaaaga aaggcgggct atgaagaggg 600
agtgtgaaga gttcaaagta cggatcgatg ccccttgttgc aaaagcgcaa aaaatacctg 660
aggagggctg gaccatggct gatggcactc cttggcctgg gaataaccct agagatcatc 720
caggaatgat ccaagtattc ttgggccaca gtggtgggct tgacacggat gggaatgagt 780
tgccacggct tgtttatgtt tctcgtgaaa agaggccagg cttccagcac cacaagaagg 840
ctggtgccat gaatgctttg attcgcgtat cagctgtcct gacgaatggt gcttatcttc 900
ttaatgtgga ttgtgatcac tacttcaata gcagcaaagc tcttagagag gctatgtgtt 960
tcatgatgga tccagcacta ggaaggaaaa cttgctatgt tcagtttcca caaagatttg 1020
atggtataga cttgcatgat cgatatgcaa accggaacat tgtcttcttt gatattaata 1080
tgaagggtct agatggcatt caaggacctg tttatgtggg aacaggatgc tgtttcaata 1140
ggcaggcctt gtatggctat gatcctgtat tgacagaagc tgatttggag cctaacatta 1200
tcattaaaag ttgctgtggc ggaagaaaaa agaaggacaa gagctatatt gattccaaaa 1260
accgtgatat gaagagaaca gaatcttcgg ctcccatctt caacatggaa gatatagaag 1320
agggatttga aggttacgag gatgaaaggt cactgcttat gtctcagaag agcttggaga 1380
aacgctttgg ccagtctcca atttttattg catccacctt tatgactcaa ggtggcatac 1440
ccccttcaac aaacccaggt tccctgctaa aggaagctat acatgtcatt agttgtggat 1500
atgaggataa aacagaatgg gggaaagaga tcggatggat atatggctct gttactgaag 1560

```
atattttaac tggtttcaag atgcatgcaa gaggttggat atccatctac tgcatgccac   1620

ttcggccttg cttcaagggt tctgctccaa ttaatctttc tgatcgtctc aaccaagtgt   1680

tacgctgggc tcttggttca gttgaaattc tacttagcag acactgtcct atctggtatg   1740

gttacaatgg aaggctaaag cttctggaga gactggcata catcaacacc attgtttatc   1800

caattacatc tatcccacta gtagcatact gcgtccttcc tgctatctgt ttactcacca   1860

acaaatttat tattcctgcg attagcaatt atgctggggc gttcttcatc ctgctttttg   1920

cttccatctt cgccactggt attttggagc ttcgatggag tggtgttggc attgaggatt   1980

ggtggagaaa tgagcagttt tgggtcattg gtggcacctc tgcacatctc tttgctgtgt   2040

tccaaggtct cttaaaagtg ctagcaggga tcgacacaaa cttcacggtc acatcaaagg   2100

caaccgatga tgatggtgat tttgctgagc tgtatgtgtt caagtggaca actcttctga   2160

tccccccac cactgtgctt gtgattaacc tggttggtat agtggctgga gtgtcgtatg   2220

ctatcaacag tggctaccaa tcatggggtc cactattcgg gaagctgttc tttgcaatct   2280

gggtgatcct ccacctctac cctttcctga agggtctcat ggggaagcag aaccgcacac   2340

cgaccatcgt catcgtttgg tccgtccttc ttgcttccat attctcgctg ctgtgggtga   2400

agatcgaccc cttcatatcc cctacccaga aggctctttc ccgtgggcag tgtggtgtaa   2460

actgctgaaa tgatccgaac tgcctgctga ataacattgc tccggcacaa tcatgatcta   2520

ccccttcgtg taaataccag aggttaggca agacttttct tggtaggtgg cgaagatgtg   2580

tcgtttaagt tcactctact gcatttgggg tgggcagcat gaaactttgt caacttatgt   2640

cgtgctactt atttgtagct aagtagcagt aagtagtgcc tgtttcatgt tgactgtcgt   2700

gactacctgt tcaccgtggg ctctggactg tcgtgatgta acctgtatgt tggaacttca   2760

agtactgatt gagctgtttg gtcaatgaca ttgagggatt ctctctctng aaattaanac   2820

aaantnggnt                                                          2830
```

<210> SEQ ID NO 6
<211> LENGTH: 821
<212> TYPE: PRT
<213> ORGANISM: Zea mays

<400> SEQUENCE: 6

```
Pro Leu Ser Arg Ile Val Pro Ile Ser Pro Asn Glu Leu Asn Leu Tyr
 1               5                  10                  15

Arg Ile Val Ile Val Leu Arg Leu Ile Ile Leu Cys Phe Phe Phe Gln
            20                  25                  30

Tyr Arg Ile Thr His Pro Val Glu Asp Ala Tyr Gly Leu Trp Leu Val
        35                  40                  45

Ser Val Ile Cys Glu Val Trp Phe Ala Leu Ser Trp Leu Leu Asp Gln
    50                  55                  60

Phe Pro Lys Trp Tyr Pro Ile Asn Arg Glu Thr Tyr Leu Asp Arg Leu
65                  70                  75                  80

Ala Leu Arg Tyr Asp Arg Glu Gly Glu Pro Ser Gln Leu Ala Pro Ile
                85                  90                  95

Asp Val Phe Val Ser Thr Val Asp Pro Leu Lys Glu Pro Pro Leu Ile
            100                 105                 110

Thr Gly Asn Thr Val Leu Ser Ile Leu Ala Val Asp Tyr Pro Val Asp
        115                 120                 125

Lys Val Ser Cys Tyr Val Ser Asp Asp Gly Ser Ala Met Leu Thr Phe
    130                 135                 140

Glu Ala Leu Ser Glu Thr Ala Glu Phe Ala Arg Lys Trp Val Pro Phe
```

-continued

```
145                 150                 155                 160

Cys Lys Lys His Asn Ile Glu Pro Arg Ala Pro Glu Phe Tyr Phe Ala
                165                 170                 175

Arg Lys Ile Asp Tyr Leu Lys Asp Lys Ile Gln Pro Ser Phe Val Lys
            180                 185                 190

Glu Arg Arg Ala Met Lys Arg Glu Cys Glu Glu Phe Lys Val Arg Ile
        195                 200                 205

Asp Ala Leu Val Ala Lys Ala Gln Lys Ile Pro Glu Glu Gly Trp Thr
    210                 215                 220

Met Ala Asp Gly Thr Pro Trp Pro Gly Asn Asn Pro Arg Asp His Pro
225                 230                 235                 240

Gly Met Ile Gln Val Phe Leu Gly His Ser Gly Gly Leu Asp Thr Asp
                245                 250                 255

Gly Asn Glu Leu Pro Arg Leu Val Tyr Val Ser Arg Glu Lys Arg Pro
            260                 265                 270

Gly Phe Gln His His Lys Lys Ala Gly Ala Met Asn Ala Leu Ile Arg
        275                 280                 285

Val Ser Ala Val Leu Thr Asn Gly Ala Tyr Leu Leu Asn Val Asp Cys
    290                 295                 300

Asp His Tyr Phe Asn Ser Ser Lys Ala Leu Arg Glu Ala Met Cys Phe
305                 310                 315                 320

Met Met Asp Pro Ala Leu Gly Arg Lys Thr Cys Tyr Val Gln Phe Pro
                325                 330                 335

Gln Arg Phe Asp Gly Ile Asp Leu His Asp Arg Tyr Ala Asn Arg Asn
            340                 345                 350

Ile Val Phe Phe Asp Ile Asn Met Lys Gly Leu Asp Gly Ile Gln Gly
        355                 360                 365

Pro Val Tyr Val Gly Thr Gly Cys Cys Phe Asn Arg Gln Ala Leu Tyr
    370                 375                 380

Gly Tyr Asp Pro Val Leu Thr Glu Ala Asp Leu Glu Pro Asn Ile Ile
385                 390                 395                 400

Ile Lys Ser Cys Cys Gly Gly Arg Lys Lys Lys Asp Lys Ser Tyr Ile
                405                 410                 415

Asp Ser Lys Asn Arg Asp Met Lys Arg Thr Glu Ser Ser Ala Pro Ile
            420                 425                 430

Phe Asn Met Glu Asp Ile Glu Glu Gly Phe Glu Gly Tyr Glu Asp Glu
        435                 440                 445

Arg Ser Leu Leu Met Ser Gln Lys Ser Leu Glu Lys Arg Phe Gly Gln
    450                 455                 460

Ser Pro Ile Phe Ile Ala Ser Thr Phe Met Thr Gln Gly Gly Ile Pro
465                 470                 475                 480

Pro Ser Thr Asn Pro Gly Ser Leu Leu Lys Glu Ala Ile His Val Ile
                485                 490                 495

Ser Cys Gly Tyr Glu Asp Lys Thr Glu Trp Gly Lys Glu Ile Gly Trp
            500                 505                 510

Ile Tyr Gly Ser Val Thr Glu Asp Ile Leu Thr Gly Phe Lys Met His
        515                 520                 525

Ala Arg Gly Trp Ile Ser Ile Tyr Cys Met Pro Leu Arg Pro Cys Phe
    530                 535                 540

Lys Gly Ser Ala Pro Ile Asn Leu Ser Asp Arg Leu Asn Gln Val Leu
545                 550                 555                 560

Arg Trp Ala Leu Gly Ser Val Glu Ile Leu Leu Ser Arg His Cys Pro
                565                 570                 575
```

```
Ile Trp Tyr Gly Tyr Asn Gly Arg Leu Lys Leu Leu Glu Arg Leu Ala
            580                 585                 590

Tyr Ile Asn Thr Ile Val Tyr Pro Ile Thr Ser Ile Pro Leu Val Ala
        595                 600                 605

Tyr Cys Val Leu Pro Ala Ile Cys Leu Leu Thr Asn Lys Phe Ile Ile
    610                 615                 620

Pro Ala Ile Ser Asn Tyr Ala Gly Ala Phe Phe Ile Leu Leu Phe Ala
625                 630                 635                 640

Ser Ile Phe Ala Thr Gly Ile Leu Glu Leu Arg Trp Ser Gly Val Gly
                645                 650                 655

Ile Glu Asp Trp Trp Arg Asn Glu Gln Phe Trp Val Ile Gly Gly Thr
            660                 665                 670

Ser Ala His Leu Phe Ala Val Phe Gln Gly Leu Leu Lys Val Leu Ala
        675                 680                 685

Gly Ile Asp Thr Asn Phe Thr Val Thr Ser Lys Ala Thr Asp Asp Asp
    690                 695                 700

Gly Asp Phe Ala Glu Leu Tyr Val Phe Lys Trp Thr Thr Leu Leu Ile
705                 710                 715                 720

Pro Pro Thr Thr Val Leu Val Ile Asn Leu Val Gly Ile Val Ala Gly
                725                 730                 735

Val Ser Tyr Ala Ile Asn Ser Gly Tyr Gln Ser Trp Gly Pro Leu Phe
            740                 745                 750

Gly Lys Leu Phe Phe Ala Ile Trp Val Ile Leu His Leu Tyr Pro Phe
        755                 760                 765

Leu Lys Gly Leu Met Gly Lys Gln Asn Arg Thr Pro Thr Ile Val Ile
    770                 775                 780

Val Trp Ser Val Leu Leu Ala Ser Ile Phe Ser Leu Leu Trp Val Lys
785                 790                 795                 800

Ile Asp Pro Phe Ile Ser Pro Thr Gln Lys Ala Leu Ser Arg Gly Gln
                805                 810                 815

Cys Gly Val Asn Cys
            820


<210> SEQ ID NO 7
<211> LENGTH: 25
<212> TYPE: DNA
<213> ORGANISM: Zea mays

<400> SEQUENCE: 7

cctctaagtc gcatagttcc gatat                                            25


<210> SEQ ID NO 8
<211> LENGTH: 25
<212> TYPE: DNA
<213> ORGANISM: Zea mays

<400> SEQUENCE: 8

tcagcagttt acaccacact gccca                                            25


<210> SEQ ID NO 9
<211> LENGTH: 3773
<212> TYPE: DNA
<213> ORGANISM: Zea mays

<400> SEQUENCE: 9

gtcgacccac gcgtccgcta ggatcaaaac cgtctcgccg ctgcaataat cttttgtcaa      60

ttcttaatcc ctcgcgtcga cagcgacagc ggaaccaact cacgttgccg cggcttcctc     120
```

```
catcggtgcg gtgccctgtc cttttctctc gtccctcctc cccccgtata gttaagcccc    180
gccccgctac tactactact agcagcagca gcgctctcgc agcgggagat gcggtgttga    240
tccgtgcccc gctcggatct cgggactggt gccggctctg cccaggcccc aggctccagg    300
ccagctccct cgacgtttct cggcgagctc gcttgccatg gagggcgacg cggacggcgt    360
gaagtcgggg aggcgcggtg gcggacaggt gtgccagatc tgcggcgacg gcgtgggcac    420
cacggcggag gggacgtct tcgccgcctg cgacgtctgc gggtttccgg tgtgccgccc    480
ctgctacgag tacgagcgca aggacggcac gcaggcgtgc cccagtgca agaccaagta    540
caagcgccac aaggggagcc cggcgatccg tggggaggaa ggagacgaca ctgatgccga    600
tagcgacttc aattaccttg catctggcaa tgaggaccag aagcagaaga ttgccgacag    660
aatgcgcagc tggcgcatga acgttggggg cagcggggat gttggtcgcc ccaagtatga    720
cagtggcgag atcgggctta ccaagtatga cagtggcgag attcctcggg gatacatccc    780
atcagtcact aacagccaga tctcaggaga aatccctggt gcttcccctg accatcatat    840
gatgtcccca actgggaaca ttggcaagcg tgctccattt ccctatgtga accattcgcc    900
aaatccgtca agggagttct ctggtagcat tgggaatgtt gcctggaaag agagggttga    960
tggctggaaa atgaagcagg acaaggggac gattcccatg acgaatggca caagcattgc   1020
tccctctgag ggtcggggtg ttggtgatat tgatgcatca actgattaca acatggaaga   1080
tgccttattg aacgacgaaa ctcgacagcc tctatctagg aaagttccac ttccttcctc   1140
caggataaat ccatacagga tggtcattgt gctgcgattg attgttctaa gcatcttctt   1200
gcactaccgt atcacaaatc ctgtgcgcaa tgcataccca ttatggcttc tatctgttat   1260
atgtgagatc tggtttgctc tttcgtggat attggatcag ttccctaagt ggtttccaat   1320
caaccgggag acgtaccttg ataggctggc attaaggtat gaccgggaag gtgagccatc   1380
tcagttggct gctgttgaca ttttcgtcag tacagtcgac ccaatgaagg agcctcctct   1440
tgtcactgcc aataccgtgc tatccattct tgctgtggat taccctgtgg ataaggtctc   1500
ttgctatgta tctgatgatg gagctgcgat gctgacattt gatgcactag ctgagacttc   1560
agagtttgct agaaaatggg taccatttgt taagaagtac aacattgaac ctagagctcc   1620
tgaatggtac ttctcccaga aaattgatta cttgaaggac aaagtgcacc cttcatttgt   1680
taaagaccgc cgggccatga agagagaata tgaagaattc aaagttaggg taaatggcct   1740
tgttgctaag gcacagaaag ttcctgagga aggatggatc atgcaagatg gcacaccatg   1800
gccaggaaac aataccaggg accatcctgg aatgattcag gttttccttg gtcacagtgg   1860
tggccttgat actgagggca atgagctacc ccgtttggtc tatgtttctc gtgaaaagcg   1920
tcctggattc cagcatcaca agaaagctgg tgccatgaat gctcttgttc gtgtctcagc   1980
tgtgcttacc aatggacaat acatgttgaa tcttgattgt gatcactaca ttaacaacag   2040
taaggctctc agggaagcta tgtgcttcct tatggaccct aacctaggaa ggagtgtctg   2100
ctacgtccag tttccccaga gattcgatgg cattgacagg aatgatcgat atgccaacag   2160
gaacaccgtg tttttcgata ttaacttgag aggtcttgat ggcatccaag gaccagttta   2220
tgtcggaact ggctgtgttt tcaaccgaac agctctatat ggttatgagc cccaattaa   2280
gcagaagaag ggtggtttct tgtcatcact atgtggcggt aggaagaagg caagcaaatc   2340
aaagaagggc tcggacaaga agaagtcgca gaagcatgtg gacagttctg tgccagtatt   2400
caaccttgaa gatatagagg agggagttga aggcgctgga tttgacgacg agaaatcact   2460
tcttatgtct caaatgagcc tggagaagag atttggccag tccgcagcgt ttgttgcctc   2520
```

```
cactctgatg gagtatggtg gtgttcctca gtccgcaact ccggagtctc ttctgaaaga   2580

agctatccat gttataagct gtggctatga ggacaagact gaatggggaa ctgagatcgg   2640

gtggatctac ggttctgtga cagaagacat tctcaccgga ttcaagatgc acgcgcgagg   2700

ctggcggtcg atctactgca tgcccaagcg gccagctttc aaggggtctg cccccatcaa   2760

tctttcggac cgtctgaacc aggtgctccg gtgggctctt gggtccgtgg agatcctctt   2820

cagccggcac tgccccctgt ggtacggcta cggagggcgg ctcaagttcc tggagagatt   2880

cgcgtacatc aacaccacca tctacccgct cacgtccatc ccgcttctca tctactgcat   2940

cctgcccgcc atctgtctgc tcaccggaaa gttcatcatt ccagagatca gcaacttcgc   3000

cagcatctgg ttcatctccc tcttcatctc gatcttcgcc acgggcatcc tggagatgag   3060

gtggagcggg gtgggcatcg acgagtggtg gaggaacgag cagttctggg tgatcggggg   3120

catctccgcg cacctcttcg ccgtgttcca gggcctgctc aaggtgctgg ccggcatcga   3180

caccaacttc accgtcacct ccaaggcctc ggacgaggac ggcgacttcg cggagctgta   3240

catgttcaag tggacgacgc tcctgatccc gcccaccacc atcctgatca tcaacctggt   3300

cggcgtcgtc gccggcatct cctacgccat caacagcgga taccagtcgt ggggcccgct   3360

cttcggcaag ctcttcttcg ccttctgggt catcgtccac ctgtacccgt tcctcaaggg   3420

cctcatgggc aggcagaacc gcaccccgac catcgtcgtc gtctgggcca tcctgctggc   3480

gtccatcttc tccttgctgt gggttcgcat cgaccccttc accacccgcg tcactggccc   3540

ggatacccag acgtgtggca tcaactgcta gggaagtgga aggtttgtac tttgtagaaa   3600

cggaggaata ccacgtgcca tctgttgtct gttaagttat atatatataa gcagcaagtg   3660

gcgttattta cagctacgta cagaccagtg gatattgttt accacaaagt tttacttgtg   3720

ttaatatgca ttcttttgtt gatataaaaa aaaaaaaaaa aaagggcggc cgc          3773
```

```
<210> SEQ ID NO 10
<211> LENGTH: 1077
<212> TYPE: PRT
<213> ORGANISM: Zea mays

<400> SEQUENCE: 10

Met Glu Gly Asp Ala Asp Gly Val Lys Ser Gly Arg Arg Gly Gly Gly
 1               5                  10                  15

Gln Val Cys Gln Ile Cys Gly Asp Gly Val Gly Thr Thr Ala Glu Gly
            20                  25                  30

Asp Val Phe Ala Ala Cys Asp Val Cys Gly Phe Pro Val Cys Arg Pro
        35                  40                  45

Cys Tyr Glu Tyr Glu Arg Lys Asp Gly Thr Gln Ala Cys Pro Gln Cys
    50                  55                  60

Lys Thr Lys Tyr Lys Arg His Lys Gly Ser Pro Ala Ile Arg Gly Glu
65                  70                  75                  80

Glu Gly Asp Asp Thr Asp Ala Asp Ser Asp Phe Asn Tyr Leu Ala Ser
                85                  90                  95

Gly Asn Glu Asp Gln Lys Gln Lys Ile Ala Asp Arg Met Arg Ser Trp
            100                 105                 110

Arg Met Asn Val Gly Gly Ser Gly Asp Val Gly Arg Pro Lys Tyr Asp
        115                 120                 125

Ser Gly Glu Ile Gly Leu Thr Lys Tyr Asp Ser Gly Glu Ile Pro Arg
    130                 135                 140

Gly Tyr Ile Pro Ser Val Thr Asn Ser Gln Ile Ser Gly Glu Ile Pro
145                 150                 155                 160
```

```
Gly Ala Ser Pro Asp His His Met Met Ser Pro Thr Gly Asn Ile Gly
                165                 170                 175

Lys Arg Ala Pro Phe Pro Tyr Val Asn His Ser Pro Asn Pro Ser Arg
            180                 185                 190

Glu Phe Ser Gly Ser Ile Gly Asn Val Ala Trp Lys Glu Arg Val Asp
        195                 200                 205

Gly Trp Lys Met Lys Gln Asp Lys Gly Thr Ile Pro Met Thr Asn Gly
    210                 215                 220

Thr Ser Ile Ala Pro Ser Glu Gly Arg Gly Val Gly Asp Ile Asp Ala
225                 230                 235                 240

Ser Thr Asp Tyr Asn Met Glu Asp Ala Leu Leu Asn Asp Glu Thr Arg
                245                 250                 255

Gln Pro Leu Ser Arg Lys Val Pro Leu Pro Ser Ser Arg Ile Asn Pro
            260                 265                 270

Tyr Arg Met Val Ile Val Leu Arg Leu Ile Val Leu Ser Ile Phe Leu
        275                 280                 285

His Tyr Arg Ile Thr Asn Pro Val Arg Asn Ala Tyr Pro Leu Trp Leu
    290                 295                 300

Leu Ser Val Ile Cys Glu Ile Trp Phe Ala Leu Ser Trp Ile Leu Asp
305                 310                 315                 320

Gln Phe Pro Lys Trp Phe Pro Ile Asn Arg Glu Thr Tyr Leu Asp Arg
                325                 330                 335

Leu Ala Leu Arg Tyr Asp Arg Glu Gly Glu Pro Ser Gln Leu Ala Ala
            340                 345                 350

Val Asp Ile Phe Val Ser Thr Val Asp Pro Met Lys Glu Pro Pro Leu
        355                 360                 365

Val Thr Ala Asn Thr Val Leu Ser Ile Leu Ala Val Asp Tyr Pro Val
    370                 375                 380

Asp Lys Val Ser Cys Tyr Val Ser Asp Asp Gly Ala Ala Met Leu Thr
385                 390                 395                 400

Phe Asp Ala Leu Ala Glu Thr Ser Glu Phe Ala Arg Lys Trp Val Pro
                405                 410                 415

Phe Val Lys Lys Tyr Asn Ile Glu Pro Arg Ala Pro Glu Trp Tyr Phe
            420                 425                 430

Ser Gln Lys Ile Asp Tyr Leu Lys Asp Lys Val His Pro Ser Phe Val
        435                 440                 445

Lys Asp Arg Arg Ala Met Lys Arg Glu Tyr Glu Glu Phe Lys Val Arg
    450                 455                 460

Val Asn Gly Leu Val Ala Lys Ala Gln Lys Val Pro Glu Glu Gly Trp
465                 470                 475                 480

Ile Met Gln Asp Gly Thr Pro Trp Pro Gly Asn Asn Thr Arg Asp His
                485                 490                 495

Pro Gly Met Ile Gln Val Phe Leu Gly His Ser Gly Gly Leu Asp Thr
            500                 505                 510

Glu Gly Asn Glu Leu Pro Arg Leu Val Tyr Val Ser Arg Glu Lys Arg
        515                 520                 525

Pro Gly Phe Gln His His Lys Lys Ala Gly Ala Met Asn Ala Leu Val
    530                 535                 540

Arg Val Ser Ala Val Leu Thr Asn Gly Gln Tyr Met Leu Asn Leu Asp
545                 550                 555                 560

Cys Asp His Tyr Ile Asn Asn Ser Lys Ala Leu Arg Glu Ala Met Cys
                565                 570                 575

Phe Leu Met Asp Pro Asn Leu Gly Arg Ser Val Cys Tyr Val Gln Phe
            580                 585                 590
```

```
Pro Gln Arg Phe Asp Gly Ile Asp Arg Asn Asp Arg Tyr Ala Asn Arg
        595                 600                 605

Asn Thr Val Phe Phe Asp Ile Asn Leu Arg Gly Leu Asp Gly Ile Gln
    610                 615                 620

Gly Pro Val Tyr Val Gly Thr Gly Cys Val Phe Asn Arg Thr Ala Leu
625                 630                 635                 640

Tyr Gly Tyr Glu Pro Pro Ile Lys Gln Lys Lys Gly Gly Phe Leu Ser
                645                 650                 655

Ser Leu Cys Gly Gly Arg Lys Lys Ala Ser Lys Ser Lys Lys Gly Ser
            660                 665                 670

Asp Lys Lys Lys Ser Gln Lys His Val Asp Ser Ser Val Pro Val Phe
        675                 680                 685

Asn Leu Glu Asp Ile Glu Glu Gly Val Glu Gly Ala Gly Phe Asp Asp
    690                 695                 700

Glu Lys Ser Leu Leu Met Ser Gln Met Ser Leu Glu Lys Arg Phe Gly
705                 710                 715                 720

Gln Ser Ala Ala Phe Val Ala Ser Thr Leu Met Glu Tyr Gly Gly Val
                725                 730                 735

Pro Gln Ser Ala Thr Pro Glu Ser Leu Leu Lys Glu Ala Ile His Val
            740                 745                 750

Ile Ser Cys Gly Tyr Glu Asp Lys Thr Glu Trp Gly Thr Glu Ile Gly
        755                 760                 765

Trp Ile Tyr Gly Ser Val Thr Glu Asp Ile Leu Thr Gly Phe Lys Met
    770                 775                 780

His Ala Arg Gly Trp Arg Ser Ile Tyr Cys Met Pro Lys Arg Pro Ala
785                 790                 795                 800

Phe Lys Gly Ser Ala Pro Ile Asn Leu Ser Asp Arg Leu Asn Gln Val
                805                 810                 815

Leu Arg Trp Ala Leu Gly Ser Val Glu Ile Leu Phe Ser Arg His Cys
            820                 825                 830

Pro Leu Trp Tyr Gly Tyr Gly Gly Arg Leu Lys Phe Leu Glu Arg Phe
        835                 840                 845

Ala Tyr Ile Asn Thr Thr Ile Tyr Pro Leu Thr Ser Ile Pro Leu Leu
    850                 855                 860

Ile Tyr Cys Ile Leu Pro Ala Ile Cys Leu Leu Thr Gly Lys Phe Ile
865                 870                 875                 880

Ile Pro Glu Ile Ser Asn Phe Ala Ser Ile Trp Phe Ile Ser Leu Phe
                885                 890                 895

Ile Ser Ile Phe Ala Thr Gly Ile Leu Glu Met Arg Trp Ser Gly Val
            900                 905                 910

Gly Ile Asp Glu Trp Trp Arg Asn Glu Gln Phe Trp Val Ile Gly Gly
        915                 920                 925

Ile Ser Ala His Leu Phe Ala Val Phe Gln Gly Leu Leu Lys Val Leu
    930                 935                 940

Ala Gly Ile Asp Thr Asn Phe Thr Val Thr Ser Lys Ala Ser Asp Glu
945                 950                 955                 960

Asp Gly Asp Phe Ala Glu Leu Tyr Met Phe Lys Trp Thr Thr Leu Leu
                965                 970                 975

Ile Pro Pro Thr Thr Ile Leu Ile Ile Asn Leu Val Gly Val Val Ala
            980                 985                 990

Gly Ile Ser Tyr Ala Ile Asn Ser Gly Tyr Gln Ser Trp Gly Pro Leu
        995                 1000                1005

Phe Gly Lys Leu Phe Phe Ala Phe Trp Val Ile Val His Leu Tyr Pro
```

```
    1010                1015                1020

Phe Leu Lys Gly Leu Met Gly Arg Gln Asn Arg Thr Pro Thr Ile Val
1025                1030                1035                1040

Val Val Trp Ala Ile Leu Leu Ala Ser Ile Phe Ser Leu Leu Trp Val
                1045                1050                1055

Arg Ile Asp Pro Phe Thr Thr Arg Val Thr Gly Pro Asp Thr Gln Thr
            1060                1065                1070

Cys Gly Ile Asn Cys
        1075


<210> SEQ ID NO 11
<211> LENGTH: 25
<212> TYPE: DNA
<213> ORGANISM: Zea mays

<400> SEQUENCE: 11

atggagggcg acgcggacgg cgtga                                          25


<210> SEQ ID NO 12
<211> LENGTH: 25
<212> TYPE: DNA
<213> ORGANISM: Zea mays

<400> SEQUENCE: 12

ctagcagttg atgccacacg tctgg                                          25


<210> SEQ ID NO 13
<211> LENGTH: 3704
<212> TYPE: DNA
<213> ORGANISM: Zea mays

<400> SEQUENCE: 13

gtcgacccac gcttccggtc ggttccgcgt cccttttccc ctcccccctc cgtcgccgcc     60

tcgagcgagc tccaccactt gctcctgcgc gaggtgaaca ctgggttagg gccactgcca    120

ccgctgggct gcctctgctt ctgcctctcc cgccagcgcg cgagcccggg ggcgattcgg    180

cgccggcacg cgggagggga agccgaggaa tgcggtgagt cggcgggggt ccggcgtttg    240

tgaactcgtg gagggctcgg attggtgcgc catggacggc ggcgacgcca cgaattcggg    300

gaagcatgtg gccgggcagg tgtgccagat ctgcggcgac ggcgtgggca ccgcggcgga    360

cggcgacctc ttcaccgcct gcgacgtctg cggcttcccc gtgtgccgcc catgctacga    420

gtacgagcgc aaggacggca cccaggcgtg cccgcagtgc aagactaagt acaagcgcca    480

caaagggagc ccaccagtac acggtgagga aaatgaggat gtggatgctg acgatgtgag    540

tgactacaac taccaagcat ctggcaacca ggatcagaag caaaagattg ctgagagaat    600

gctcacttgg cggacaaact cacgtggcag tgatattggc ctggctaagt atgacagcgg    660

tgaaattggg catgggaagt atgacagtgg tgagatccct cgtggatata tcccgtcact    720

aactcatagc cagatctcag gagagattcc tggagcttcc cctgatcata tgatgtctcc    780

tgttgggaac attggcaggc gtggacatca atttccttat gtaaatcatt ctccaaaccc    840

atcgagggag ttctccggta gccttggcaa tgttgcatgg aaagagaggg tggatggatg    900

gaaaatgaag gataaaggtg caattcctat gaccaatgga acaagcattg ctccatcaga    960

agggcgtgga gttgctgata ttgatgcttc tactgattat aacatggaag atgccttact   1020

gaatgatgaa actcggcaac ctctatctag aaaagtgcca attccttcat ccagaataaa   1080

tccgtacaga atggtcattg tgctacgttt ggctgttcta tgcatattct tgcgctaccg   1140
```

-continued

```
tatcacacat cctgtgaaca atgcatatcc actgtggctt ttatccgtca tatgtgagat   1200
ctggtttgct ttgtcctgga ttttggatca gttcccaaag tggtccccaa tcaaccgtga   1260
aacatacctt gatagactgg ctttaaggta tgaccgagaa ggtgaaccat ctcaattagc   1320
tcctgttgat atttttgtca gtactgtgga tccaatgaag gagcctcctc ttgtcactgc   1380
aaatactgtg ctttccatcc ttgctgtcga ttatccggtt gacaaggtat cttgctatgt   1440
ttcggatgat ggagctgcta tgctgacttt tgatgctctc tctgaaactt cagagtttgc   1500
tagaaaatgg gttccgttct gtaagaagta caacatagag cctagggccc cggaatggta   1560
ctttgctcag aaaattgatt acttgaaaga caaagttcaa acctcatttg tgaaagaacg   1620
ccgggccatg aagagagaat atgaagaatt caaagttcgt atcaatggtc ttgtagccaa   1680
ggcacaaaaa gttcccgagg agggatggat catgcaagat ggtacacctt ggcctgggaa   1740
caatactagg gaccatcctg gaatgattca ggttttcctg ggtcacagtg gagggcttga   1800
cgttgaaggc aatgaacttc ctcgtttggt ttatgtgtct cgtgaaaaac gtcctggatt   1860
ccaacatcac aagaaggctg gtgccatgaa tgcacttgtt cgtgtatcag ctgtccttac   1920
taatgggcaa tacatgttga atcttgattg tgaccactac atcaataata gcaaggctct   1980
tcgagaagct atgtgcttcc ttatggaccc aaacctagga aggaatgtct gttatgtcca   2040
atttcctcag aggtttgatg gtattgatag gaatgaccga tatgcaaaca ggaacactgt   2100
gtttttcgat attaacttga gaggtcttga cggcattcaa gggccagttt atgtgggaac   2160
tggttgtgtg tttaacagaa cggccttata tggttatgag cctccagtca agaaaaaaaa   2220
gccaggcttc ttctcttcgc tttgtggggg aaggaaaaag acgtcaaaat ctaagaagag   2280
ctcggaaaag aagaagtcac atagacacgc agacagttct gtaccagtat ttaatctcga   2340
agatatagag gaagggattg aaggttctca gtttgatgat gagaaatcgc tgattatgtc   2400
tcaaatgagc ttggagaaga gatttggcca gtccagtgtt tttgtagcct ctactctgat   2460
ggaatatggt ggtgttccac aatctgcaac tccagagtct cttctgaaag aagctattca   2520
tgtcatcagc tgtggctatg aggacaaaac tgactgggga actgagattg ggtggatcta   2580
tggttctgtt acagaagaca ttctcaccgg attcaagatg catgctcgag gctggcgatc   2640
aatctactgc atgcctaagc gaccagcttt caagggatct gctcctatca acctttcgga   2700
tcgtttgaat caagtgcttc ggtgggctct tggttccatt gaaattcttt tcagcaggca   2760
ttgtcccata tggtatggct atggaggccg gcttaaattc ctggagagat ttgcttatat   2820
caacacaaca atttatccac tcacatcaat cccgctcctc ctgtactgca tattgccagc   2880
agtttgtctt ctcactggga agttcatcat cccaaagatt agtaacctag agagtgtttg   2940
gtttatatcg ctctttatct caatctttgc cactggtatc cttgagatga ggtggagtgg   3000
tgttggcatt gatgaatggt ggaggaacga gcagttctgg gtcattggtg gtatttctgc   3060
gcatttattt gccgtcttcc agggtctcct gaaggtgctt gctggtatcg acacgagctt   3120
cactgtcacc tctaaggcca ctgacgaaga aggtgatttt gccgagctct acatgttcaa   3180
gtggacaacg cttctgatcc caccaaccac tattttgatc atcaacctgg tcggcgtggt   3240
cgctggcatt tcctacgcaa tcaatagcgg ttaccagtca tggggacctc ttttcgggaa   3300
gctcttcttt gcgttctggg tgattgtcca cctgtacccc ttcctcaagg gcctcatggg   3360
gaagcagaac cgcacgccga ccattgtcgt tgtctgggct atcctccttg cgtcgatctt   3420
ttccctgatg tgggttcgta tcgatccatt caccacccgg gtcactggcc ctgatatcgc   3480
gaaatgtggc atcaactgct aggatgagct gaagatagtt aaagagtgga actagacgca   3540
```

```
ttgtgcatcg taagttatca gtgggtggct ctttttatag tatggtagga acttggtcgg   3600

gagacgttaa ttacatatgc tatatgtacc tccgctggtc tttatccgta agttaatata   3660

tatactgctt tgagaattaa aaaaaaaaaa aaaagggcgg ccgc                    3704


<210> SEQ ID NO 14
<211> LENGTH: 1076
<212> TYPE: PRT
<213> ORGANISM: Zea mays

<400> SEQUENCE: 14

Met Asp Gly Gly Asp Ala Thr Asn Ser Gly Lys His Val Ala Gly Gln
 1               5                  10                  15

Val Cys Gln Ile Cys Gly Asp Gly Val Gly Thr Ala Ala Asp Gly Asp
            20                  25                  30

Leu Phe Thr Ala Cys Asp Val Cys Gly Phe Pro Val Cys Arg Pro Cys
        35                  40                  45

Tyr Glu Tyr Glu Arg Lys Asp Gly Thr Gln Ala Cys Pro Gln Cys Lys
    50                  55                  60

Thr Lys Tyr Lys Arg His Lys Gly Ser Pro Pro Val His Gly Glu Glu
65                  70                  75                  80

Asn Glu Asp Val Asp Ala Asp Asp Val Ser Asp Tyr Asn Tyr Gln Ala
                85                  90                  95

Ser Gly Asn Gln Asp Gln Lys Gln Lys Ile Ala Glu Arg Met Leu Thr
            100                 105                 110

Trp Arg Thr Asn Ser Arg Gly Ser Asp Ile Gly Leu Ala Lys Tyr Asp
        115                 120                 125

Ser Gly Glu Ile Gly His Gly Lys Tyr Asp Ser Gly Glu Ile Pro Arg
    130                 135                 140

Gly Tyr Ile Pro Ser Leu Thr His Ser Gln Ile Ser Gly Glu Ile Pro
145                 150                 155                 160

Gly Ala Ser Pro Asp His Met Met Ser Pro Val Gly Asn Ile Gly Arg
                165                 170                 175

Arg Gly His Gln Phe Pro Tyr Val Asn His Ser Pro Asn Pro Ser Arg
            180                 185                 190

Glu Phe Ser Gly Ser Leu Gly Asn Val Ala Trp Lys Glu Arg Val Asp
        195                 200                 205

Gly Trp Lys Met Lys Asp Lys Gly Ala Ile Pro Met Thr Asn Gly Thr
    210                 215                 220

Ser Ile Ala Pro Ser Glu Gly Arg Gly Val Ala Asp Ile Asp Ala Ser
225                 230                 235                 240

Thr Asp Tyr Asn Met Glu Asp Ala Leu Leu Asn Asp Glu Thr Arg Gln
                245                 250                 255

Pro Leu Ser Arg Lys Val Pro Ile Pro Ser Ser Arg Ile Asn Pro Tyr
            260                 265                 270

Arg Met Val Ile Val Leu Arg Leu Ala Val Leu Cys Ile Phe Leu Arg
        275                 280                 285

Tyr Arg Ile Thr His Pro Val Asn Asn Ala Tyr Pro Leu Trp Leu Leu
    290                 295                 300

Ser Val Ile Cys Glu Ile Trp Phe Ala Leu Ser Trp Ile Leu Asp Gln
305                 310                 315                 320

Phe Pro Lys Trp Ser Pro Ile Asn Arg Glu Thr Tyr Leu Asp Arg Leu
                325                 330                 335

Ala Leu Arg Tyr Asp Arg Glu Gly Glu Pro Ser Gln Leu Ala Pro Val
            340                 345                 350
```

```
Asp Ile Phe Val Ser Thr Val Asp Pro Met Lys Glu Pro Pro Leu Val
        355                 360                 365

Thr Ala Asn Thr Val Leu Ser Ile Leu Ala Val Asp Tyr Pro Val Asp
    370                 375                 380

Lys Val Ser Cys Tyr Val Ser Asp Asp Gly Ala Ala Met Leu Thr Phe
385                 390                 395                 400

Asp Ala Leu Ser Glu Thr Ser Glu Phe Ala Arg Lys Trp Val Pro Phe
                405                 410                 415

Cys Lys Lys Tyr Asn Ile Glu Pro Arg Ala Pro Glu Trp Tyr Phe Ala
            420                 425                 430

Gln Lys Ile Asp Tyr Leu Lys Asp Lys Val Gln Thr Ser Phe Val Lys
        435                 440                 445

Glu Arg Arg Ala Met Lys Arg Glu Tyr Glu Glu Phe Lys Val Arg Ile
    450                 455                 460

Asn Gly Leu Val Ala Lys Ala Gln Lys Val Pro Glu Glu Gly Trp Ile
465                 470                 475                 480

Met Gln Asp Gly Thr Pro Trp Pro Gly Asn Asn Thr Arg Asp His Pro
                485                 490                 495

Gly Met Ile Gln Val Phe Leu Gly His Ser Gly Gly Leu Asp Val Glu
            500                 505                 510

Gly Asn Glu Leu Pro Arg Leu Val Tyr Val Ser Arg Glu Lys Arg Pro
        515                 520                 525

Gly Phe Gln His His Lys Lys Ala Gly Ala Met Asn Ala Leu Val Arg
    530                 535                 540

Val Ser Ala Val Leu Thr Asn Gly Gln Tyr Met Leu Asn Leu Asp Cys
545                 550                 555                 560

Asp His Tyr Ile Asn Asn Ser Lys Ala Leu Arg Glu Ala Met Cys Phe
                565                 570                 575

Leu Met Asp Pro Asn Leu Gly Arg Asn Val Cys Tyr Val Gln Phe Pro
            580                 585                 590

Gln Arg Phe Asp Gly Ile Asp Arg Asn Asp Arg Tyr Ala Asn Arg Asn
        595                 600                 605

Thr Val Phe Phe Asp Ile Asn Leu Arg Gly Leu Asp Gly Ile Gln Gly
    610                 615                 620

Pro Val Tyr Val Gly Thr Gly Cys Val Phe Asn Arg Thr Ala Leu Tyr
625                 630                 635                 640

Gly Tyr Glu Pro Pro Val Lys Lys Lys Lys Pro Gly Phe Phe Ser Ser
                645                 650                 655

Leu Cys Gly Gly Arg Lys Lys Thr Ser Lys Ser Lys Lys Ser Ser Glu
            660                 665                 670

Lys Lys Lys Ser His Arg His Ala Asp Ser Ser Val Pro Val Phe Asn
        675                 680                 685

Leu Glu Asp Ile Glu Glu Gly Ile Glu Gly Ser Gln Phe Asp Asp Glu
    690                 695                 700

Lys Ser Leu Ile Met Ser Gln Met Ser Leu Glu Lys Arg Phe Gly Gln
705                 710                 715                 720

Ser Ser Val Phe Val Ala Ser Thr Leu Met Glu Tyr Gly Gly Val Pro
                725                 730                 735

Gln Ser Ala Thr Pro Glu Ser Leu Leu Lys Glu Ala Ile His Val Ile
            740                 745                 750

Ser Cys Gly Tyr Glu Asp Lys Thr Asp Trp Gly Thr Glu Ile Gly Trp
        755                 760                 765

Ile Tyr Gly Ser Val Thr Glu Asp Ile Leu Thr Gly Phe Lys Met His
    770                 775                 780
```

```
Ala Arg Gly Trp Arg Ser Ile Tyr Cys Met Pro Lys Arg Pro Ala Phe
785                 790                 795                 800

Lys Gly Ser Ala Pro Ile Asn Leu Ser Asp Arg Leu Asn Gln Val Leu
                805                 810                 815

Arg Trp Ala Leu Gly Ser Ile Glu Ile Leu Phe Ser Arg His Cys Pro
            820                 825                 830

Ile Trp Tyr Gly Tyr Gly Gly Arg Leu Lys Phe Leu Glu Arg Phe Ala
        835                 840                 845

Tyr Ile Asn Thr Thr Ile Tyr Pro Leu Thr Ser Ile Pro Leu Leu Leu
    850                 855                 860

Tyr Cys Ile Leu Pro Ala Val Cys Leu Leu Thr Gly Lys Phe Ile Ile
865                 870                 875                 880

Pro Lys Ile Ser Asn Leu Glu Ser Val Trp Phe Ile Ser Leu Phe Ile
                885                 890                 895

Ser Ile Phe Ala Thr Gly Ile Leu Glu Met Arg Trp Ser Gly Val Gly
            900                 905                 910

Ile Asp Glu Trp Trp Arg Asn Glu Gln Phe Trp Val Ile Gly Gly Ile
        915                 920                 925

Ser Ala His Leu Phe Ala Val Phe Gln Gly Leu Leu Lys Val Leu Ala
    930                 935                 940

Gly Ile Asp Thr Ser Phe Thr Val Thr Ser Lys Ala Thr Asp Glu Glu
945                 950                 955                 960

Gly Asp Phe Ala Glu Leu Tyr Met Phe Lys Trp Thr Thr Leu Leu Ile
                965                 970                 975

Pro Pro Thr Thr Ile Leu Ile Ile Asn Leu Val Gly Val Val Ala Gly
            980                 985                 990

Ile Ser Tyr Ala Ile Asn Ser Gly Tyr Gln Ser Trp Gly Pro Leu Phe
        995                 1000                1005

Gly Lys Leu Phe Phe Ala Phe Trp Val Ile Val His Leu Tyr Pro Phe
    1010                1015                1020

Leu Lys Gly Leu Met Gly Lys Gln Asn Arg Thr Pro Thr Ile Val Val
1025                1030                1035                1040

Val Trp Ala Ile Leu Leu Ala Ser Ile Phe Ser Leu Met Trp Val Arg
                1045                1050                1055

Ile Asp Pro Phe Thr Thr Arg Val Thr Gly Pro Asp Ile Ala Lys Cys
            1060                1065                1070

Gly Ile Asn Cys
        1075


<210> SEQ ID NO 15
<211> LENGTH: 25
<212> TYPE: DNA
<213> ORGANISM: Zea mays

<400> SEQUENCE: 15

atggacggcg gcgacgccac gaatt                                           25


<210> SEQ ID NO 16
<211> LENGTH: 25
<212> TYPE: DNA
<213> ORGANISM: Zea mays

<400> SEQUENCE: 16

ctagcagttg atgccacatt tcgcg                                           25


<210> SEQ ID NO 17
```

<211> LENGTH: 3813
<212> TYPE: DNA
<213> ORGANISM: Zea mays

<400> SEQUENCE: 17

```
ccacagctca tataccaaga gccggagcag cttagcgcag cccagagcgg cgccgcgcca     60

agcacaaccc ccacccgcca cagccgcgtg cgcatgtgag cggtcgccgc ggccgggaga    120

ccagaggagg ggaggactac gtgcatttcg ctgtgccgcc gccgcggggt tcgtgcgcga    180

gcgagatccg gcggggcggg gcggggggcc tgagatggag gctagcgcgg ggctggtggc    240

cggctcgcat aaccggaacg agctggtggt gatccgccgc gaccgcgagt cgggagccgc    300

gggcggcggc gcggcgcgcc gggcggaggc gccgtgccag atatgcggcg acgaggtcgg    360

ggtgggcttc gacggggagc ccttcgtggc gtgcaacgag tgcgccttcc ccgtctgccg    420

cgcctgctac gagtacgagc gccgcgaggg ctcgcaagcg tgcccgcagt gcaggacccg    480

ctacaagcgc ctcaagggct gcccgcgggt ggccggcgac gaggaggagg acggcgtcga    540

cgacctggag ggcgagttcg gcctgcagga cggcgccgcc cacgaggacg acccgcagta    600

cgtcgccgag tccatgctca gggcgcagat gagctacggc cgcggcggcg acgcgcaccc    660

cggcttcagc cccgtcccca acgtgccgct cctcaccaac ggccagatgg ttgatgacat    720

cccgccggag cagcacgcgc tcgtgccgtc ctacatgagc ggcggcggcg gcgggggcaa    780

gaggatccac ccgctccctt tcgcagatcc caaccttcca gtgcaaccga gatccatgga    840

cccgtccaag gatctggccg cctacggata tggcagcgtg gcctggaagg agagaatgga    900

gggctggaag cagaagcagg agcgcctgca gcatgtcagg agcgagggtg gcggtgattg    960

ggatggcgac gatgcagatc tgccactaat ggatgaagct aggcagccat tgtccagaaa   1020

agtccctata tcatcaagcc gaattaatcc ctacaggatg attatcgtta tccggttggt   1080

ggttttgggt ttcttcttcc actaccgagt gatgcatccg gcgaaagatg catttgcatt   1140

gtggctcata tctgtaatct gtgaaatctg gtttgcgatg tcctggattc ttgatcagtt   1200

cccaaagtgg cttccaatcg agagagagac ttacctggac cgtttgtcac taaggtttga   1260

caaggaaggt caaccctctc agcttgctcc aatcgacttc tttgtcagta cggttgatcc   1320

cacaaaggaa cctcccttgg tcacagcgaa cactgtcctt tccatccttt ctgtggatta   1380

tccggttgag aaggtctcct gctatgtttc tgatgatggt gctgcaatgc ttacgtttga   1440

agcattgtct gaaacatctg aatttgcaaa gaaatgggtt cctttcagca aaaagtttaa   1500

tatcgagcct cgtgctcctg agtggtactt ccaacagaag atagactacc tgaaagacaa   1560

ggttgctgct tcatttgtta gggagaggag ggcgatgaag agagaatacg aggaattcaa   1620

ggtaaggatc aatgccttgg ttgcaaaagc ccaaaaggtt cctgaggaag gatggacaat   1680

gcaagatgga agcccctggc ctggaaacaa cgtacgcgat catcctggaa tgattcaggt   1740

attccttggc caaagtggcg gtcgtgatgt ggaaggaaat gagttgcctc gcctggttta   1800

tgtctcgaga gaaaagaggc caggttataa ccatcacaag aaggctggtg ccatgaatgc   1860

actggtccgt gtctctgctg tcttatcaaa tgctgcatac ctattgaact tggactgtga   1920

tcactacatc aacaatagca aggccataaa agaggctatg tgtttcatga tggatccttt   1980

ggtggggaag aaagtgtgct atgtacagtt ccctcagagg tttgatggta ttgacaaaaa   2040

tgatcgatac gctaacagga acgttgtctt ttttgacatc aacatgaaag gtttggacgg   2100

tattcaagga cccatttatg tgggtactgg atgtgttttc agacggcagg cactgtatgg   2160

ttatgatgct cctaaaacga agaagccacc atcaagaact tgcaactgct ggcccaagtg   2220
```

```
gtgcctctct tgctgctgca gcaggaacaa gaataaaaag aagactacaa aaccaaagac   2280
ggagaagaag aaaagattat ttttcaagaa agcagaaaac ccatctcctg catatgcttt   2340
gggtgaaatt gatgaaggtg ctccaggtgc tgatatcgag aaggccggaa tcgtaaatca   2400
acagaaacta gagaagaaat ttgggcagtc ttctgttttt gtcgcatcaa cacttcttga   2460
gaacggaggg accctgaaga gcgcaagtcc agcttctctt ctgaaggaag ctatacatgt   2520
tatcagctgc ggctacgaag acaagaccga ctggggaaaa gagattggct ggatttacgg   2580
atcgatcaca gaggatatct tgactggatt taagatgcac tgccatggct ggcggtctat   2640
ttactgcatc ccgaagcggc ctgcattcaa aggttctgcg cctctgaacc tttccgaccg   2700
tcttcaccag gtccttcgct gggcccttgg gtccgtcgaa atttcttca gcaagcactg    2760
cccactttgg tacggatacg gcggcgggct aaaattcctg gaaaggtttt cttatatcaa   2820
ctccatcgtt tatccctgga cgtccattcc tctcctggct tactgtacct tgcctgccat   2880
ctgcctgctc acggggaagt ttatcacacc agagcttacc aatgtcgcca gtatctggtt   2940
catggcactt ttcatctgca tctccgtgac cggcatcctg gaaatgaggt ggagtggcgt   3000
ggccatcgac gactggtgga ggaacgagca gttctgggtc atcggaggcg tttcggcgca   3060
tctgttcgcg gtgttccagg gcctgctgaa ggtgttcgcc ggcatcgaca cgagcttcac   3120
cgtgacgtcg aaggccgggg acgacgagga gttctcggag ctgtacacgt tcaagtggac   3180
caccctgctg ataccccga ccacgctcct cctgctgaac ttcatcgggg tggtggccgg    3240
gatctcgaac gcgatcaaca acgggtacga gtcgtggggc cccctgttcg ggaagctctt   3300
cttcgccttc tgggtgatcg tccacctgta cccgttcctc aagggtctgg tggggaggca   3360
gaacaggacg ccgacgatcg tcatcgtctg gtccatcctg ctggcctcga tcttctcgct   3420
cctgtgggtc cgcgtcgacc cgttcctcgc caagagcaac ggcccgctcc tggaggagtg   3480
tggcctggac tgcaactgaa gtgggggccc cctgtcactc gaagttctgt cacgggcgaa   3540
ttacgcctga tttttgttg ttgttgttgt tggaattctt tgctgtagat agaaaccaca    3600
tgtccacggc atctctgctg tgtccattgg agcaggagag aggtgcctgc tgctgtttgt   3660
tgagtaaatt aaaagtttta aagttataca gtgatgcaca ttccagtgcc cagtgtattc   3720
ccttttaca gtctgtatat tagcgacaaa ggacatattg gttaggagtt tgattctttt    3780
gtaaaaaaa aaaaaaaaa aaaaaaaaa aaa                                  3813
```

<210> SEQ ID NO 18
<211> LENGTH: 1094
<212> TYPE: PRT
<213> ORGANISM: Zea mays

<400> SEQUENCE: 18

```
Met Glu Ala Ser Ala Gly Leu Val Ala Gly Ser His Asn Arg Asn Glu
 1               5                  10                  15

Leu Val Val Ile Arg Arg Asp Arg Glu Ser Gly Ala Ala Gly Gly Gly
            20                  25                  30

Ala Ala Arg Arg Ala Glu Ala Pro Cys Gln Ile Cys Gly Asp Glu Val
        35                  40                  45

Gly Val Gly Phe Asp Gly Glu Pro Phe Val Ala Cys Asn Glu Cys Ala
    50                  55                  60

Phe Pro Val Cys Arg Ala Cys Tyr Glu Tyr Glu Arg Arg Glu Gly Ser
65                  70                  75                  80

Gln Ala Cys Pro Gln Cys Arg Thr Arg Tyr Lys Arg Leu Lys Gly Cys
                85                  90                  95
```

```
Pro Arg Val Ala Gly Asp Glu Glu Glu Asp Gly Val Asp Asp Leu Glu
            100                 105                 110

Gly Glu Phe Gly Leu Gln Asp Gly Ala Ala His Glu Asp Asp Pro Gln
        115                 120                 125

Tyr Val Ala Glu Ser Met Leu Arg Ala Gln Met Ser Tyr Gly Arg Gly
    130                 135                 140

Gly Asp Ala His Pro Gly Phe Ser Pro Val Pro Asn Val Pro Leu Leu
145                 150                 155                 160

Thr Asn Gly Gln Met Val Asp Asp Ile Pro Pro Glu Gln His Ala Leu
                165                 170                 175

Val Pro Ser Tyr Met Ser Gly Gly Gly Gly Gly Gly Lys Arg Ile His
            180                 185                 190

Pro Leu Pro Phe Ala Asp Pro Asn Leu Pro Val Gln Pro Arg Ser Met
        195                 200                 205

Asp Pro Ser Lys Asp Leu Ala Ala Tyr Gly Tyr Gly Ser Val Ala Trp
    210                 215                 220

Lys Glu Arg Met Glu Gly Trp Lys Gln Lys Gln Glu Arg Leu Gln His
225                 230                 235                 240

Val Arg Ser Glu Gly Gly Gly Asp Trp Asp Gly Asp Asp Ala Asp Leu
                245                 250                 255

Pro Leu Met Asp Glu Ala Arg Gln Pro Leu Ser Arg Lys Val Pro Ile
            260                 265                 270

Ser Ser Ser Arg Ile Asn Pro Tyr Arg Met Ile Ile Val Ile Arg Leu
        275                 280                 285

Val Val Leu Gly Phe Phe Phe His Tyr Arg Val Met His Pro Ala Lys
    290                 295                 300

Asp Ala Phe Ala Leu Trp Leu Ile Ser Val Ile Cys Glu Ile Trp Phe
305                 310                 315                 320

Ala Met Ser Trp Ile Leu Asp Gln Phe Pro Lys Trp Leu Pro Ile Glu
                325                 330                 335

Arg Glu Thr Tyr Leu Asp Arg Leu Ser Leu Arg Phe Asp Lys Glu Gly
            340                 345                 350

Gln Pro Ser Gln Leu Ala Pro Ile Asp Phe Phe Val Ser Thr Val Asp
        355                 360                 365

Pro Thr Lys Glu Pro Pro Leu Val Thr Ala Asn Thr Val Leu Ser Ile
    370                 375                 380

Leu Ser Val Asp Tyr Pro Val Glu Lys Val Ser Cys Tyr Val Ser Asp
385                 390                 395                 400

Asp Gly Ala Ala Met Leu Thr Phe Glu Ala Leu Ser Glu Thr Ser Glu
                405                 410                 415

Phe Ala Lys Lys Trp Val Pro Phe Ser Lys Lys Phe Asn Ile Glu Pro
            420                 425                 430

Arg Ala Pro Glu Trp Tyr Phe Gln Gln Lys Ile Asp Tyr Leu Lys Asp
        435                 440                 445

Lys Val Ala Ala Ser Phe Val Arg Glu Arg Arg Ala Met Lys Arg Glu
    450                 455                 460

Tyr Glu Glu Phe Lys Val Arg Ile Asn Ala Leu Val Ala Lys Ala Gln
465                 470                 475                 480

Lys Val Pro Glu Glu Gly Trp Thr Met Gln Asp Gly Ser Pro Trp Pro
                485                 490                 495

Gly Asn Asn Val Arg Asp His Pro Gly Met Ile Gln Val Phe Leu Gly
            500                 505                 510

Gln Ser Gly Gly Arg Asp Val Glu Gly Asn Glu Leu Pro Arg Leu Val
        515                 520                 525
```

```
Tyr Val Ser Arg Glu Lys Arg Pro Gly Tyr Asn His His Lys Lys Ala
    530                 535                 540

Gly Ala Met Asn Ala Leu Val Arg Val Ser Ala Val Leu Ser Asn Ala
545                 550                 555                 560

Ala Tyr Leu Leu Asn Leu Asp Cys Asp His Tyr Ile Asn Asn Ser Lys
                565                 570                 575

Ala Ile Lys Glu Ala Met Cys Phe Met Met Asp Pro Leu Val Gly Lys
            580                 585                 590

Lys Val Cys Tyr Val Gln Phe Pro Gln Arg Phe Asp Gly Ile Asp Lys
        595                 600                 605

Asn Asp Arg Tyr Ala Asn Arg Asn Val Val Phe Phe Asp Ile Asn Met
    610                 615                 620

Lys Gly Leu Asp Gly Ile Gln Gly Pro Ile Tyr Val Gly Thr Gly Cys
625                 630                 635                 640

Val Phe Arg Arg Gln Ala Leu Tyr Gly Tyr Asp Ala Pro Lys Thr Lys
                645                 650                 655

Lys Pro Pro Ser Arg Thr Cys Asn Cys Trp Pro Lys Trp Cys Leu Ser
            660                 665                 670

Cys Cys Cys Ser Arg Asn Lys Asn Lys Lys Lys Thr Thr Lys Pro Lys
        675                 680                 685

Thr Glu Lys Lys Lys Arg Leu Phe Phe Lys Lys Ala Glu Asn Pro Ser
    690                 695                 700

Pro Ala Tyr Ala Leu Gly Glu Ile Asp Glu Gly Ala Pro Gly Ala Asp
705                 710                 715                 720

Ile Glu Lys Ala Gly Ile Val Asn Gln Gln Lys Leu Glu Lys Lys Phe
                725                 730                 735

Gly Gln Ser Ser Val Phe Val Ala Ser Thr Leu Leu Glu Asn Gly Gly
            740                 745                 750

Thr Leu Lys Ser Ala Ser Pro Ala Ser Leu Leu Lys Glu Ala Ile His
        755                 760                 765

Val Ile Ser Cys Gly Tyr Glu Asp Lys Thr Asp Trp Gly Lys Glu Ile
    770                 775                 780

Gly Trp Ile Tyr Gly Ser Ile Thr Glu Asp Ile Leu Thr Gly Phe Lys
785                 790                 795                 800

Met His Cys His Gly Trp Arg Ser Ile Tyr Cys Ile Pro Lys Arg Pro
                805                 810                 815

Ala Phe Lys Gly Ser Ala Pro Leu Asn Leu Ser Asp Arg Leu His Gln
            820                 825                 830

Val Leu Arg Trp Ala Leu Gly Ser Val Glu Ile Phe Phe Ser Lys His
        835                 840                 845

Cys Pro Leu Trp Tyr Gly Tyr Gly Gly Gly Leu Lys Phe Leu Glu Arg
    850                 855                 860

Phe Ser Tyr Ile Asn Ser Ile Val Tyr Pro Trp Thr Ser Ile Pro Leu
865                 870                 875                 880

Leu Ala Tyr Cys Thr Leu Pro Ala Ile Cys Leu Leu Thr Gly Lys Phe
                885                 890                 895

Ile Thr Pro Glu Leu Thr Asn Val Ala Ser Ile Trp Phe Met Ala Leu
            900                 905                 910

Phe Ile Cys Ile Ser Val Thr Gly Ile Leu Glu Met Arg Trp Ser Gly
        915                 920                 925

Val Ala Ile Asp Asp Trp Trp Arg Asn Glu Gln Phe Trp Val Ile Gly
    930                 935                 940

Gly Val Ser Ala His Leu Phe Ala Val Phe Gln Gly Leu Leu Lys Val
```

```
945                 950                 955                 960

Phe Ala Gly Ile Asp Thr Ser Phe Thr Val Thr Ser Lys Ala Gly Asp
                965                 970                 975

Asp Glu Glu Phe Ser Glu Leu Tyr Thr Phe Lys Trp Thr Thr Leu Leu
            980                 985                 990

Ile Pro Pro Thr Thr Leu Leu Leu Leu Asn Phe Ile Gly Val Val Ala
        995                 1000                1005

Gly Ile Ser Asn Ala Ile Asn Asn Gly Tyr Glu Ser Trp Gly Pro Leu
    1010                1015                1020

Phe Gly Lys Leu Phe Phe Ala Phe Trp Val Ile Val His Leu Tyr Pro
1025                1030                1035                1040

Phe Leu Lys Gly Leu Val Gly Arg Gln Asn Arg Thr Pro Thr Ile Val
                1045                1050                1055

Ile Val Trp Ser Ile Leu Leu Ala Ser Ile Phe Ser Leu Leu Trp Val
            1060                1065                1070

Arg Val Asp Pro Phe Leu Ala Lys Ser Asn Gly Pro Leu Leu Glu Glu
        1075                1080                1085

Cys Gly Leu Asp Cys Asn
    1090


<210> SEQ ID NO 19
<211> LENGTH: 25
<212> TYPE: DNA
<213> ORGANISM: Zea mays

<400> SEQUENCE: 19

atggaggcta gcgcggggct ggtgg                                            25


<210> SEQ ID NO 20
<211> LENGTH: 25
<212> TYPE: DNA
<213> ORGANISM: Zea mays

<400> SEQUENCE: 20

tcagttgcag tccaggccac actcc                                            25


<210> SEQ ID NO 21
<211> LENGTH: 3799
<212> TYPE: DNA
<213> ORGANISM: Zea mays
<220> FEATURE:
<221> NAME/KEY: misc_feature
<222> LOCATION: 3757, 3775, 3777, 3782
<223> OTHER INFORMATION: n = A,T,C or G

<400> SEQUENCE: 21

caactcacgt tgccgcggct tcctccatcg gtgcggtgcc ctgtcctttt ctctcctcca      60

cctccctagt ccctcctccc ccccgcatac atagctacta ctagtagcac cacgctcgca     120

gcgggagatg cggtgctgat ccgtgcccct gctcggatct cgggagtggt gccgacttgt     180

gtcgcttcgg ctctgcctag gccagctcct tgtcggttct gggcgagctc gcctgccatg     240

gagggcgacg cggacggcgt gaagtcgggg aggcgcgggg gagggcaggt gtgccagatc     300

tgcggcgatg gcgtgggcac tacggcggag ggagacgtct tcaccgcctg cgacgtctgc     360

gggttcccgg tgtgccgccc ctgctacgag tacgagcgca aggacggcac acaagcgtgc     420

ccccagtgca aaaacaagta caagcgccac aaggggagtc cagcgatccg aggggaggaa     480

ggagacgata ctgatgccga tgatgctagc gacttcaact accctgcatc tggcaatgac     540

gaccagaagc agaagattgc tgacaggatg cgcagctggc gcatgaatgc tgggggcagc     600
```

```
ggggatgttg gccgccccaa gtatgacagt ggtgagatcg ggcttaccaa gtacgacagt    660

ggtgagatcc ctcggggata catcccgtca gtcactaaca gccagatttc gggagaaatc    720

cctggtgctt cccctgacca tcatatgatg tctcctactg ggaacattgg caggcgcgcc    780

ccatttccct atatgaatca ttcatcaaat ccgtcgaggg aattctctgg tagcgttggg    840

aatgttgcct ggaaagagag ggttgatggc tggaaaatga agcaggacaa gggaacaatt    900

cccatgacga atggcacaag cattgctccc tctgagggcc ggggtgttgg tgatattgat    960

gcatcaactg attacaacat ggaagatgcc ttattaaacg atgaaactcg ccagcctcta   1020

tctaggaaag ttccacttcc ttcctccagg ataaatccat acaggatggt cattgtgcta   1080

cgattgattg ttctaagcat cttcttgcac taccggatca caaatcctgt gcgtaatgca   1140

tacccactgt ggcttctatc tgttatatgt gagatctggt ttgctctttc ctggatattg   1200

gatcagtttc caaagtggtt tccaatcaac cgcgagactt accttgatag actcgcatta   1260

aggtatgacc gggaaggtga gccatctcag ttggctgctg ttgacatttt tgtcagtact   1320

gtcgacccaa tgaaggagcc tcctcttgtc actgccaata ccgtgctatc cattctcgct   1380

gtggactatc ctgtggataa ggtctcttgc tatgtatctg atgatggagc tgctatgctg   1440

acatttgatg cactagctga gacttcagag tttgctagaa aatgggtgcc atttgttaag   1500

aagtacaaca ttgaacctag agctcctgaa tggtacttct cccagaaaat tgattacttg   1560

aaggacaaag tgcacccttc atttgttaaa gaccgccggg ccatgaagag agaatatgaa   1620

gaattcaaaa ttagggtaaa tggccttgtt gctaaggcac aaaaagtccc tgaggaagga   1680

tggatcatgc aagatggcac accatggcca ggaaacaata ccagggacca tcctggaatg   1740

attcaggttt tccttggtca cagtggtggt cttgatactg agggtaatga gctaccccgt   1800

ttggtctatg tttctcgtga aaaacgtcct ggattccagc atcacaagaa agctggtgcc   1860

atgaatgctc ttgtccgcgt ctcagctgtg cttaccaatg gacaatacat gttgaatctt   1920

gattgtgatc actacatcaa caacagtaag gctctcaggg aagctatgtg cttccttatg   1980

gatcctaacc taggaaggag tgtctgctat gttcagtttc cccagaggtt cgatggtatt   2040

gataggaatg atcgatatgc caacaggaac accgtgtttt tcgatattaa cttgagaggt   2100

cttgatggca tccaaggacc agtttatgtg ggcactggct gtgttttcaa cagaacagct   2160

ctatatggtt atgagccccc aattaagcaa aagaagggtg gtttcttgtc atcactatgt   2220

ggtggcagga agaagggaag caaatcaaag aagggctcag acaagaaaaa gtcacagaag   2280

catgtggaca gttctgtgcc agtattcaat cttgaagata tagaggaggg agttgaaggc   2340

gctggatttg atgatgagaa atcacttctt atgtctcaaa tgagcttgga gaagagattt   2400

ggccaatctg cagcttttgt tgcgtccact ctgatggaat atggtggtgt tcctcagtct   2460

gcgactccag aatctcttct gaaagaagct atccatgtca taagttgtgg ctacgaggac   2520

aagattgaat ggggaactga gattgggtgg atctatggtt ctgtgacgga agatattctc   2580

actgggttca agatgcacgc acgaggctgg cggtcgatct actgcatgcc taagcggccg   2640

gccttcaagg gatcggctcc catcaatctc tcagaccgtc tgaaccaggt gctccggtgg   2700

gctctcggtt cagtggaaat ccttttcagc cggcattgcc ccctatggta cgggtacgga   2760

ggacgcctga agttcttgga gagattcgcc tacatcaaca ccaccatcta cccgctcacg   2820

tccctcccgc tcctcattta ctgtatcctg cctgccatct gcctgctcac ggggaagttc   2880

atcatcccag agatcagcaa cttcgctagt atctggttca tctctctctt catctcgatc   2940

ttcgccacgg gtatcctgga gatgaggtgg agcggcgtgg gcatcgacga gtggtggagg   3000
```

```
aacgagcagt tctgggtcat cggaggcatc tccgcccacc tcttcgccgt cttccagggc   3060

ctcctcaagg tgcttgccgg catcgacacc aacttcaccg tcacctccaa ggcctcggat   3120

gaagacggcg acttcgcgga gctgtacatg ttcaagtgga cgacacttct gatcccgccc   3180

accaccatcc tgatcatcaa cctggtcggc gttgttgccg gcatctccta cgccatcaac   3240

agcgggtacc agtcgtgggg tccgctcttc ggcaagctct tcttcgcctt ctgggtgatc   3300

gttcacctgt acccgttcct caagggtctc atgggtcggc agaaccgcac cccgaccatc   3360

gtggttgtct gggcgatcct gctggcgtcg atcttctcct tgctgtgggt tcgcatcgat   3420

ccgttcacca accgcgtcac tggcccggat actcgaacgt gtggcatcaa ctgctaggga   3480

ggtggaaggt ttgtagaaac agagagatac cacgaatgtg ccgctgccac aaattgtctg   3540

ttagtaagtt atataggcag gtggcgttat ttacagctac gtacacacaa ggggatactc   3600

cgtttatcac tggtgtgcat tcttttgttg atataagtta ctatatatac gtattgcttc   3660

tactttgtgg agagtggctg acaggaccag ttttgtaatg ttatgaacag caaagaaata   3720

agttagtttc caaaaaaaaa aaaaaaaaaa aaaaaanaaa aaaaaaaaaa aaaananaaa   3780

anaaaaaaaa aaaaaacccc                                               3799


<210> SEQ ID NO 22
<211> LENGTH: 1079
<212> TYPE: PRT
<213> ORGANISM: Zea mays

<400> SEQUENCE: 22

Met Glu Gly Asp Ala Asp Gly Val Lys Ser Gly Arg Arg Gly Gly Gly
1               5                   10                  15

Gln Val Cys Gln Ile Cys Gly Asp Gly Val Gly Thr Thr Ala Glu Gly
            20                  25                  30

Asp Val Phe Thr Ala Cys Asp Val Cys Gly Phe Pro Val Cys Arg Pro
        35                  40                  45

Cys Tyr Glu Tyr Glu Arg Lys Asp Gly Thr Gln Ala Cys Pro Gln Cys
    50                  55                  60

Lys Asn Lys Tyr Lys Arg His Lys Gly Ser Pro Ala Ile Arg Gly Glu
65                  70                  75                  80

Glu Gly Asp Asp Thr Asp Ala Asp Asp Ala Ser Asp Phe Asn Tyr Pro
                85                  90                  95

Ala Ser Gly Asn Asp Asp Gln Lys Gln Lys Ile Ala Asp Arg Met Arg
            100                 105                 110

Ser Trp Arg Met Asn Ala Gly Gly Ser Gly Asp Val Gly Arg Pro Lys
        115                 120                 125

Tyr Asp Ser Gly Glu Ile Gly Leu Thr Lys Tyr Asp Ser Gly Glu Ile
    130                 135                 140

Pro Arg Gly Tyr Ile Pro Ser Val Thr Asn Ser Gln Ile Ser Gly Glu
145                 150                 155                 160

Ile Pro Gly Ala Ser Pro Asp His His Met Met Ser Pro Thr Gly Asn
                165                 170                 175

Ile Gly Arg Arg Ala Pro Phe Pro Tyr Met Asn His Ser Ser Asn Pro
            180                 185                 190

Ser Arg Glu Phe Ser Gly Ser Val Gly Asn Val Ala Trp Lys Glu Arg
        195                 200                 205

Val Asp Gly Trp Lys Met Lys Gln Asp Lys Gly Thr Ile Pro Met Thr
    210                 215                 220

Asn Gly Thr Ser Ile Ala Pro Ser Glu Gly Arg Gly Val Gly Asp Ile
```

```
225                 230                 235                 240

Asp Ala Ser Thr Asp Tyr Asn Met Glu Asp Ala Leu Leu Asn Asp Glu
                245                 250                 255

Thr Arg Gln Pro Leu Ser Arg Lys Val Pro Leu Pro Ser Ser Arg Ile
            260                 265                 270

Asn Pro Tyr Arg Met Val Ile Val Leu Arg Leu Ile Val Leu Ser Ile
        275                 280                 285

Phe Leu His Tyr Arg Ile Thr Asn Pro Val Arg Asn Ala Tyr Pro Leu
    290                 295                 300

Trp Leu Leu Ser Val Ile Cys Glu Ile Trp Phe Ala Leu Ser Trp Ile
305                 310                 315                 320

Leu Asp Gln Phe Pro Lys Trp Phe Pro Ile Asn Arg Glu Thr Tyr Leu
                325                 330                 335

Asp Arg Leu Ala Leu Arg Tyr Asp Arg Glu Gly Glu Pro Ser Gln Leu
            340                 345                 350

Ala Ala Val Asp Ile Phe Val Ser Thr Val Asp Pro Met Lys Glu Pro
        355                 360                 365

Pro Leu Val Thr Ala Asn Thr Val Leu Ser Ile Leu Ala Val Asp Tyr
    370                 375                 380

Pro Val Asp Lys Val Ser Cys Tyr Val Ser Asp Asp Gly Ala Ala Met
385                 390                 395                 400

Leu Thr Phe Asp Ala Leu Ala Glu Thr Ser Glu Phe Ala Arg Lys Trp
                405                 410                 415

Val Pro Phe Val Lys Lys Tyr Asn Ile Glu Pro Arg Ala Pro Glu Trp
            420                 425                 430

Tyr Phe Ser Gln Lys Ile Asp Tyr Leu Lys Asp Lys Val His Pro Ser
        435                 440                 445

Phe Val Lys Asp Arg Arg Ala Met Lys Arg Glu Tyr Glu Glu Phe Lys
    450                 455                 460

Ile Arg Val Asn Gly Leu Val Ala Lys Ala Gln Lys Val Pro Glu Glu
465                 470                 475                 480

Gly Trp Ile Met Gln Asp Gly Thr Pro Trp Pro Gly Asn Asn Thr Arg
                485                 490                 495

Asp His Pro Gly Met Ile Gln Val Phe Leu Gly His Ser Gly Gly Leu
            500                 505                 510

Asp Thr Glu Gly Asn Glu Leu Pro Arg Leu Val Tyr Val Ser Arg Glu
        515                 520                 525

Lys Arg Pro Gly Phe Gln His His Lys Lys Ala Gly Ala Met Asn Ala
    530                 535                 540

Leu Val Arg Val Ser Ala Val Leu Thr Asn Gly Gln Tyr Met Leu Asn
545                 550                 555                 560

Leu Asp Cys Asp His Tyr Ile Asn Asn Ser Lys Ala Leu Arg Glu Ala
                565                 570                 575

Met Cys Phe Leu Met Asp Pro Asn Leu Gly Arg Ser Val Cys Tyr Val
            580                 585                 590

Gln Phe Pro Gln Arg Phe Asp Gly Ile Asp Arg Asn Asp Arg Tyr Ala
        595                 600                 605

Asn Arg Asn Thr Val Phe Phe Asp Ile Asn Leu Arg Gly Leu Asp Gly
    610                 615                 620

Ile Gln Gly Pro Val Tyr Val Gly Thr Gly Cys Val Phe Asn Arg Thr
625                 630                 635                 640

Ala Leu Tyr Gly Tyr Glu Pro Pro Ile Lys Gln Lys Lys Gly Gly Phe
                645                 650                 655
```

```
Leu Ser Ser Leu Cys Gly Gly Arg Lys Lys Gly Ser Lys Ser Lys Lys
            660                 665                 670

Gly Ser Asp Lys Lys Lys Ser Gln Lys His Val Asp Ser Ser Val Pro
        675                 680                 685

Val Phe Asn Leu Glu Asp Ile Glu Glu Gly Val Glu Gly Ala Gly Phe
    690                 695                 700

Asp Asp Glu Lys Ser Leu Leu Met Ser Gln Met Ser Leu Glu Lys Arg
705                 710                 715                 720

Phe Gly Gln Ser Ala Ala Phe Val Ala Ser Thr Leu Met Glu Tyr Gly
                725                 730                 735

Gly Val Pro Gln Ser Ala Thr Pro Glu Ser Leu Leu Lys Glu Ala Ile
            740                 745                 750

His Val Ile Ser Cys Gly Tyr Glu Asp Lys Ile Glu Trp Gly Thr Glu
        755                 760                 765

Ile Gly Trp Ile Tyr Gly Ser Val Thr Glu Asp Ile Leu Thr Gly Phe
    770                 775                 780

Lys Met His Ala Arg Gly Trp Arg Ser Ile Tyr Cys Met Pro Lys Arg
785                 790                 795                 800

Pro Ala Phe Lys Gly Ser Ala Pro Ile Asn Leu Ser Asp Arg Leu Asn
                805                 810                 815

Gln Val Leu Arg Trp Ala Leu Gly Ser Val Glu Ile Leu Phe Ser Arg
            820                 825                 830

His Cys Pro Leu Trp Tyr Gly Tyr Gly Gly Arg Leu Lys Phe Leu Glu
        835                 840                 845

Arg Phe Ala Tyr Ile Asn Thr Thr Ile Tyr Pro Leu Thr Ser Leu Pro
    850                 855                 860

Leu Leu Ile Tyr Cys Ile Leu Pro Ala Ile Cys Leu Leu Thr Gly Lys
865                 870                 875                 880

Phe Ile Ile Pro Glu Ile Ser Asn Phe Ala Ser Ile Trp Phe Ile Ser
                885                 890                 895

Leu Phe Ile Ser Ile Phe Ala Thr Gly Ile Leu Glu Met Arg Trp Ser
            900                 905                 910

Gly Val Gly Ile Asp Glu Trp Trp Arg Asn Glu Gln Phe Trp Val Ile
        915                 920                 925

Gly Gly Ile Ser Ala His Leu Phe Ala Val Phe Gln Gly Leu Leu Lys
    930                 935                 940

Val Leu Ala Gly Ile Asp Thr Asn Phe Thr Val Thr Ser Lys Ala Ser
945                 950                 955                 960

Asp Glu Asp Gly Asp Phe Ala Glu Leu Tyr Met Phe Lys Trp Thr Thr
                965                 970                 975

Leu Leu Ile Pro Pro Thr Thr Ile Leu Ile Ile Asn Leu Val Gly Val
            980                 985                 990

Val Ala Gly Ile Ser Tyr Ala Ile Asn Ser Gly Tyr Gln Ser Trp Gly
        995                 1000                1005

Pro Leu Phe Gly Lys Leu Phe Phe Ala Phe Trp Val Ile Val His Leu
    1010                1015                1020

Tyr Pro Phe Leu Lys Gly Leu Met Gly Arg Gln Asn Arg Thr Pro Thr
1025                1030                1035                1040

Ile Val Val Val Trp Ala Ile Leu Leu Ala Ser Ile Phe Ser Leu Leu
                1045                1050                1055

Trp Val Arg Ile Asp Pro Phe Thr Asn Arg Val Thr Gly Pro Asp Thr
            1060                1065                1070

Arg Thr Cys Gly Ile Asn Cys
        1075
```

<210> SEQ ID NO 23
<211> LENGTH: 25
<212> TYPE: DNA
<213> ORGANISM: Zea mays

<400> SEQUENCE: 23
atggagggcg acgcggacgg cgtga 25

<210> SEQ ID NO 24
<211> LENGTH: 25
<212> TYPE: DNA
<213> ORGANISM: Zea mays

<400> SEQUENCE: 24
ctagcagttg atgccacacg ttcga 25

<210> SEQ ID NO 25
<211> LENGTH: 3470
<212> TYPE: DNA
<213> ORGANISM: Zea mays

<400> SEQUENCE: 25
gcccccggtc gatcgctcgg caatcggcat ggacgccggc tcggtcaccg gtggcctcgc 60
cgcgggctcg cacatgcggg acgagctgca tgtcatgcgc gcccgcgagg agccgaacgc 120
caaggtccgg agcgccgacg tgaagacgtg ccgcgtgtgc gccgacgagg tcgggacgcg 180
ggaggacggg cagcccttcg tggcgtgcgc cgagtgcggc ttccccgtct gccggccctg 240
ctacgagtac gagcgcagcg agggcacgca gtgctgcccg cagtgcaaca cccgctacaa 300
gcgccagaaa gggtgcccga gggtggaagg ggacgaggag gagggcccgg agatggacga 360
cttcgaggac gagttccccg ccaagagccc caagaagcct cacgagcctg tcgcgttcga 420
cgtctactcg gagaacggcg agcacccggc gcagaaatgg cggacgggtg gccagacgct 480
gtcgtccttc accggaagcg tcgccgggaa ggacctggag gcggagaggg agatggaggg 540
gagcatggag tggaaggacc ggatcgacaa gtggaagacc aagcaggaga agaggggcaa 600
gctcaaccac gacgacagcg acgacgacga cgacaagaac gaagacgagt acatgctgct 660
tgccgaggcc cgacagccgc tgtggcgcaa ggttccgatc ccgtcgagca tgatcaaccc 720
gtaccgcatc gtcatcgtgc tccgcctggt ggtgctctgc ttcttcctca agttccggat 780
cacgacgccc gccacggacg ccgtgcctct gtggctggcg tccgtcatct gcgagctctg 840
gttcgccttc tcctggatcc tggaccagct gccaaagtgg gcgccggtga cgcgggagac 900
gtacctggac cgcctggcgc tgcggtacga ccgtgagggc gaggcgtgcc ggctgtcccc 960
catcgacttc ttcgtcagca cggtggaccc gctcaaggag ccgcccatca tcaccgccaa 1020
caccgtgctg tccatcctcg ccgtcgacta ccccgtggac cgcgtcagct gctacgtctc 1080
cgacgacggc gcgtccatgc tgctcttcga cgcgctgtcc gagaccgccg agttcgcgcg 1140
ccgctgggtg cccttctgca agaagttcgc cgtggagccg cgcgccccgg agttctactt 1200
ctcgcagaag atcgactacc tcaaggacaa ggtgcagccg acgttcgtca aggagcgccg 1260
cgccatgaag agggagtacg aggagttcaa ggtgcgcatc aacgcgctgg tggccaaggc 1320
gcagaagaag cccgaggagg ggtgggtcat gcaggacggc acgccgtggc ccgggaacaa 1380
cacgcgcgac cacccgggta tgatccaggt ctacctcggc aaccagggcg cgctggacgt 1440
ggagggccac gagctgccgc gcctcgtcta cgtgtcccgt gagaagcgcc ccgggtacaa 1500
ccaccacaag aaggcgggcg ccatgaacgc gctggtgcgc gtctccgccg tgctcaccaa 1560

```
cgcgcccttc atcctcaacc tcgactgcga ccactacgtc aacaacagca aggccgtgcg   1620

cgaggccatg tgcttcctca tggacccgca gctggggaag aagctctgct acgtccagtt   1680

cccgcagcgc ttcgatggca tcgatcgcca cgaccgatac gccaaccgca acgtcgtctt   1740

cttcgacatc aacatgaagg ggctggacgg catccagggc ccggtgtacg tcggcacggg   1800

gtgcgtgttc aaccgccagg cgctgtacgg ctacgacccg ccgcggcccg agaagcggcc   1860

caagatgacg tgcgactgct ggccgtcgtg gtgctgctgc tgctgctgct tcggcggcgg   1920

caagcgcggc aaggcgcgca aggacaagaa gggcgacggc ggcgaggagc cgcgccgggg   1980

cctgctcggc ttctacagga agcggagcaa gaaggacaag ctcggcggcg ggtcggtggc   2040

cggcagcaag aagggcggcg ggctgtacaa gaagcaccag cgcgcgttcg agctggagga   2100

gatcgaggag gggctggagg ggtacgacga gctggagcgc tcctcgctca tgtcgcagaa   2160

gagcttcgag aagcggttcg gccagtcgcc cgtgttcatc gcctccacgc tcgtcgagga   2220

cggcggcctg ccgcagggcg ccgccgccga ccccgccgcg ctcatcaagg aggccatcca   2280

cgtcatcagc tgcggatacg aggagaagac cgagtggggc aaggagattg ggtggatcta   2340

tgggtcggtg acagaggata tcctgacggg gttcaagatg cactgccggg ggtggaagtc   2400

cgtgtactgc acgccgacac ggccggcgtt caaggggtcg gcgcccatca acttgtctga   2460

tcgtctccac caggtgctgc gctgggcgct ggggtccgtg gagatcttca tgagccgcca   2520

ctgcccgctc cggtacgcct acggcggccg gctcaagtgg ctggagcgct tcgcctacac   2580

caacaccatc gtgtacccct tcacctccat cccgctcctc gcctactgca ccatccccgc   2640

cgtctgcctg ctcaccggca agttcatcat tcccacgctg aacaacctcg ccagcatctg   2700

gttcatcgcg ctcttcctgt ccatcatcgc gacgagcgtc ctggagctgc ggtggagcgg   2760

ggtgagcatc gaggactggt ggcgcaacga gcagttctgg gtcatcggcg gcgtgtccgc   2820

gcatctcttc gccgtgttcc agggcttcct caaggttctg ggcggcgtgg acaccagctt   2880

caccgtcacc tccaaggcgg ccggcgacga ggccgacgcc ttcggggacc tctacctctt   2940

caagtggacc accctgctgg tgccccccac cacgctcatc atcatcaaca tggtgggcat   3000

cgtggccggc gtgtccgacg ccgtcaacaa cggctacggc tcctggggcc cgctcttcgg   3060

caagctcttc ttctccttct gggtcatcgt ccacctctac ccgttcctca aggggctcat   3120

ggggaggcag aaccggacgc ccaccatcgt cgtgctctgg tccatcctcc tcgcctccat   3180

cttctcgctc gtctgggtca ggatcgaccc gtttatcccg aaggccaagg gccccatcct   3240

caagccatgc ggagtcgagt gctgagctca cctagctacc ttcttgttgc atgtacggac   3300

gccgccgtgc gtttggacat acaggcactt ttgggccagg ctactcatgt tcgacttttt   3360

ttttaatttt gtacaagatt tgtgatcgag tgactgagtg agacagagtg ttgggtgtaa   3420

gaactgtgat ggaattcact caaattaatg gacatttttt ttcttcaaaa               3470
```

```
<210> SEQ ID NO 26
<211> LENGTH: 1078
<212> TYPE: PRT
<213> ORGANISM: Zea mays

<400> SEQUENCE: 26

Met Asp Ala Gly Ser Val Thr Gly Gly Leu Ala Ala Gly Ser His Met
 1               5                  10                  15

Arg Asp Glu Leu His Val Met Arg Ala Arg Glu Glu Pro Asn Ala Lys
            20                  25                  30

Val Arg Ser Ala Asp Val Lys Thr Cys Arg Val Cys Ala Asp Glu Val
```

```
        35                  40                  45

Gly Thr Arg Glu Asp Gly Gln Pro Phe Val Ala Cys Ala Glu Cys Gly
    50                  55                  60

Phe Pro Val Cys Arg Pro Cys Tyr Glu Tyr Glu Arg Ser Glu Gly Thr
65                  70                  75                  80

Gln Cys Cys Pro Gln Cys Asn Thr Arg Tyr Lys Arg Gln Lys Gly Cys
                85                  90                  95

Pro Arg Val Glu Gly Asp Glu Glu Glu Gly Pro Glu Met Asp Asp Phe
            100                 105                 110

Glu Asp Glu Phe Pro Ala Lys Ser Pro Lys Lys Pro His Glu Pro Val
        115                 120                 125

Ala Phe Asp Val Tyr Ser Glu Asn Gly Glu His Pro Ala Gln Lys Trp
    130                 135                 140

Arg Thr Gly Gly Gln Thr Leu Ser Ser Phe Thr Gly Ser Val Ala Gly
145                 150                 155                 160

Lys Asp Leu Glu Ala Glu Arg Glu Met Glu Gly Ser Met Glu Trp Lys
                165                 170                 175

Asp Arg Ile Asp Lys Trp Lys Thr Lys Gln Glu Lys Arg Gly Lys Leu
            180                 185                 190

Asn His Asp Asp Ser Asp Asp Asp Asp Asp Lys Asn Glu Asp Glu Tyr
        195                 200                 205

Met Leu Leu Ala Glu Ala Arg Gln Pro Leu Trp Arg Lys Val Pro Ile
    210                 215                 220

Pro Ser Ser Met Ile Asn Pro Tyr Arg Ile Val Ile Val Leu Arg Leu
225                 230                 235                 240

Val Val Leu Cys Phe Phe Leu Lys Phe Arg Ile Thr Thr Pro Ala Thr
                245                 250                 255

Asp Ala Val Pro Leu Trp Leu Ala Ser Val Ile Cys Glu Leu Trp Phe
            260                 265                 270

Ala Phe Ser Trp Ile Leu Asp Gln Leu Pro Lys Trp Ala Pro Val Thr
        275                 280                 285

Arg Glu Thr Tyr Leu Asp Arg Leu Ala Leu Arg Tyr Asp Arg Glu Gly
    290                 295                 300

Glu Ala Cys Arg Leu Ser Pro Ile Asp Phe Phe Val Ser Thr Val Asp
305                 310                 315                 320

Pro Leu Lys Glu Pro Pro Ile Ile Thr Ala Asn Thr Val Leu Ser Ile
                325                 330                 335

Leu Ala Val Asp Tyr Pro Val Asp Arg Val Ser Cys Tyr Val Ser Asp
            340                 345                 350

Asp Gly Ala Ser Met Leu Leu Phe Asp Ala Leu Ser Glu Thr Ala Glu
        355                 360                 365

Phe Ala Arg Arg Trp Val Pro Phe Cys Lys Lys Phe Ala Val Glu Pro
    370                 375                 380

Arg Ala Pro Glu Phe Tyr Phe Ser Gln Lys Ile Asp Tyr Leu Lys Asp
385                 390                 395                 400

Lys Val Gln Pro Thr Phe Val Lys Glu Arg Arg Ala Met Lys Arg Glu
                405                 410                 415

Tyr Glu Glu Phe Lys Val Arg Ile Asn Ala Leu Val Ala Lys Ala Gln
            420                 425                 430

Lys Lys Pro Glu Glu Gly Trp Val Met Gln Asp Gly Thr Pro Trp Pro
        435                 440                 445

Gly Asn Asn Thr Arg Asp His Pro Gly Met Ile Gln Val Tyr Leu Gly
    450                 455                 460
```

```
Asn Gln Gly Ala Leu Asp Val Glu Gly His Glu Leu Pro Arg Leu Val
465                 470                 475                 480

Tyr Val Ser Arg Glu Lys Arg Pro Gly Tyr Asn His His Lys Lys Ala
                485                 490                 495

Gly Ala Met Asn Ala Leu Val Arg Val Ser Ala Val Leu Thr Asn Ala
            500                 505                 510

Pro Phe Ile Leu Asn Leu Asp Cys Asp His Tyr Val Asn Asn Ser Lys
        515                 520                 525

Ala Val Arg Glu Ala Met Cys Phe Leu Met Asp Pro Gln Leu Gly Lys
    530                 535                 540

Lys Leu Cys Tyr Val Gln Phe Pro Gln Arg Phe Asp Gly Ile Asp Arg
545                 550                 555                 560

His Asp Arg Tyr Ala Asn Arg Asn Val Val Phe Phe Asp Ile Asn Met
                565                 570                 575

Lys Gly Leu Asp Gly Ile Gln Gly Pro Val Tyr Val Gly Thr Gly Cys
            580                 585                 590

Val Phe Asn Arg Gln Ala Leu Tyr Gly Tyr Asp Pro Pro Arg Pro Glu
        595                 600                 605

Lys Arg Pro Lys Met Thr Cys Asp Cys Trp Pro Ser Trp Cys Cys Cys
    610                 615                 620

Cys Cys Cys Phe Gly Gly Gly Lys Arg Gly Lys Ala Arg Lys Asp Lys
625                 630                 635                 640

Lys Gly Asp Gly Gly Glu Glu Pro Arg Arg Gly Leu Leu Gly Phe Tyr
                645                 650                 655

Arg Lys Arg Ser Lys Lys Asp Lys Leu Gly Gly Gly Ser Val Ala Gly
            660                 665                 670

Ser Lys Lys Gly Gly Gly Leu Tyr Lys Lys His Gln Arg Ala Phe Glu
        675                 680                 685

Leu Glu Glu Ile Glu Glu Gly Leu Glu Gly Tyr Asp Glu Leu Glu Arg
    690                 695                 700

Ser Ser Leu Met Ser Gln Lys Ser Phe Glu Lys Arg Phe Gly Gln Ser
705                 710                 715                 720

Pro Val Phe Ile Ala Ser Thr Leu Val Glu Asp Gly Gly Leu Pro Gln
                725                 730                 735

Gly Ala Ala Ala Asp Pro Ala Ala Leu Ile Lys Glu Ala Ile His Val
            740                 745                 750

Ile Ser Cys Gly Tyr Glu Glu Lys Thr Glu Trp Gly Lys Glu Ile Gly
        755                 760                 765

Trp Ile Tyr Gly Ser Val Thr Glu Asp Ile Leu Thr Gly Phe Lys Met
    770                 775                 780

His Cys Arg Gly Trp Lys Ser Val Tyr Cys Thr Pro Thr Arg Pro Ala
785                 790                 795                 800

Phe Lys Gly Ser Ala Pro Ile Asn Leu Ser Asp Arg Leu His Gln Val
                805                 810                 815

Leu Arg Trp Ala Leu Gly Ser Val Glu Ile Phe Met Ser Arg His Cys
            820                 825                 830

Pro Leu Arg Tyr Ala Tyr Gly Gly Arg Leu Lys Trp Leu Glu Arg Phe
        835                 840                 845

Ala Tyr Thr Asn Thr Ile Val Tyr Pro Phe Thr Ser Ile Pro Leu Leu
    850                 855                 860

Ala Tyr Cys Thr Ile Pro Ala Val Cys Leu Leu Thr Gly Lys Phe Ile
865                 870                 875                 880

Ile Pro Thr Leu Asn Asn Leu Ala Ser Ile Trp Phe Ile Ala Leu Phe
                885                 890                 895
```

```
Leu Ser Ile Ile Ala Thr Ser Val Leu Glu Leu Arg Trp Ser Gly Val
            900                 905                 910

Ser Ile Glu Asp Trp Trp Arg Asn Glu Gln Phe Trp Val Ile Gly Gly
        915                 920                 925

Val Ser Ala His Leu Phe Ala Val Phe Gln Gly Phe Leu Lys Val Leu
    930                 935                 940

Gly Gly Val Asp Thr Ser Phe Thr Val Thr Ser Lys Ala Ala Gly Asp
945                 950                 955                 960

Glu Ala Asp Ala Phe Gly Asp Leu Tyr Leu Phe Lys Trp Thr Thr Leu
                965                 970                 975

Leu Val Pro Pro Thr Thr Leu Ile Ile Ile Asn Met Val Gly Ile Val
            980                 985                 990

Ala Gly Val Ser Asp Ala Val Asn Asn Gly Tyr Gly Ser Trp Gly Pro
        995                 1000                1005

Leu Phe Gly Lys Leu Phe Phe Ser Phe Trp Val Ile Val His Leu Tyr
    1010                1015                1020

Pro Phe Leu Lys Gly Leu Met Gly Arg Gln Asn Arg Thr Pro Thr Ile
1025                1030                1035                1040

Val Val Leu Trp Ser Ile Leu Leu Ala Ser Ile Phe Ser Leu Val Trp
                1045                1050                1055

Val Arg Ile Asp Pro Phe Ile Pro Lys Ala Lys Gly Pro Ile Leu Lys
            1060                1065                1070

Pro Cys Gly Val Glu Cys
        1075


<210> SEQ ID NO 27
<211> LENGTH: 3231
<212> TYPE: DNA
<213> ORGANISM: Zea mays

<400> SEQUENCE: 27

ccacgcgtcc gggaggggcc atgatggagt cggcggcggc ccagtcctgc gcggcgtgcg      60

gggacgacgc gcgcgctgcc tgccgcgcgt gcagctacgc gctctgcagg gcgtgcctcg     120

acgaggacgc cgccgagggc cgcaccacat gcgcgcgctg cggaggggac tacgccgcta     180

tcaacccagc gcgcgccagc gagggaaccg aggcggagga ggaggtggtg gagaaccacc     240

acaccgccgg tggcctgcgt gagagggtca ccatgggcag ccacctcaat gatcgccagg     300

atgaagtaag ccacgccagg accatgagca gcttgtcggg aattggtagt gaattgaatg     360

atgaatctgg taagcccatc tggaagaaca gggtggagag ttggaaggaa aagaagaatg     420

agaagaaagc ctcggccaaa aagactgcag ctaaagcaca gcctccgcct gtcgaagaac     480

agatcatgga tgaaaaagac ttgacagatg catatgagcc actctcccgg gtcatcccaa     540

tatcaaagaa caagctcaca ccttacagag cagtgatcat tatgcggtta attgttcttg     600

ggctcttctt tcactaccgt atcaccaatc ctgttaacag tgcctttggt ctctggatga     660

catcagttat atgtgagatc tggtttggtt tctcctggat attggatcaa ttcccgaagt     720

ggtatcctat caatcgtgag acttatgttg ataggctgat tgcacgatat ggagatggtg     780

aagaatctgg gttagcacct gtagatttct ttgtcagtac agtggatcca ttgaaagagc     840

ctccactaat cactgcaaac actgtgctgt ctattcttgc tgtggactat cccgttgaga     900

agatctcatg ctatgtatct gatgatggtt ctgctatgct cacatttgaa tcgctcgcag     960

agactgcaga atatgctaga aagtgggtgc cgttttgcaa gaagtacgcc attgagccac    1020

gagctcctga gttctacttc tcacagaaaa ttgactactt gaaggacaag atacacccat    1080
```

```
cttttgtcaa ggagcgtagg gctatgaaga gagactatga agagtacaag gtgaggataa   1140

atgctttggt tgccaaggct caaaagacac ctgatgaagg ctggatcatg caagacggta   1200

caccatggcc tgggaacaat cctcgtgacc accctggcat gatccaggtt ttcctgggtg   1260

agactggtgc acgggacttt gatggaaatg aacttcctcg gttagtgtat gtgtcaagag   1320

agaaaagacc aggctaccaa caccacaaga aggcaggggc tatgaatgct ctggtccgag   1380

tgtctgctgt tctgacaaat gccccttaca ttcttaatct tgattgtgat cactatgtta   1440

acaacagcaa agctgttcgt gaagcaatgt gcttcatgat ggaccctact gttggcagag   1500

atgtctgcta tgtacaattc ccccagaggt tcgatggcat tgatcgcagt gatcgatatg   1560

ccaataggaa cgttgtgttc tttgatgtta atatgaaagg acttgatggc ctccaaggcc   1620

cagtttatgt gggaactggt tgttgtttca ataggcaagc actttatggt tatgggcctc   1680

catctctgcc cgcacttcca aagtcttcga tttgttcctg gtgttgctgc tgctgtccca   1740

agaaaaaggt tgaaagaagt gagagggaaa tcaacagaga ctctcggcga gaagacctcg   1800

agtctgccat tttaaccttt cgcgaaattg acaactacga tgagtacgag aggtccatgc   1860

tcatctctca gatgagcttc gagaagtctt ttgggctgtc ctcggtcttt attgaatcga   1920

cccttatgga gaatgggggc gtccctgaat ctgcaaaccc atctacccta attaaagaag   1980

ccattcatgt cattagctgt ggatatgaag agaaaactga atggggaaaa gagattggct   2040

ggatctatgg ttcagttaca gaggatattc tgactgggtt taagatgcac tgccgtggct   2100

ggagatccat ctactgcatg ccggtgagac ctgcattcaa gggatcagcc ccaatcaatc   2160

tttccgatcg tcttcaccaa gttctccggt gggctcttgt ttctgtcgag atcttcttca   2220

gtcggcactg cccgctgtgg tacggttacg gtggcggccg tctgaaatgg ctccagaggc   2280

tctcctacat caacaccatc gtgtacccgt tcacttctct tcctctcgtt gcctactgtt   2340

gcctgcctgc catttgcctg ctcacaggaa agttcattat acctacgctg tccaacgctg   2400

caacgatatg gtttcttggc ctcttcatgt ccatcatcgt gacgagcgtg ttggagctgc   2460

ggtggagtgg catcgggatc gaggactggt ggcgcaacga gcagttctgg gtcatcggag   2520

gcgtgtccgc gcacctgttc gccgtgttcc agggtatcct caagatgatt gccgggctgg   2580

acaccaactt cacggtcacg gcaaaggcca cggacgacac tgagttcggg gagctgtacc   2640

tgttcaagtg gacgacggtg ctgatcccgc ccacaagcat cctggtgctg aacctggtgg   2700

gcgtggtggc tgggttctcg gccgcgctca acagcggcta cgagtcctgg ggcccgctct   2760

tcggtaaggt gttcttcgcc atgtgggtga tcatgcacct gtacccgttc ctcaagggtc   2820

tcatgggccg ccagaaccgc acgccgacca tcgtggtgct ctggtccgtc ctcctcgcct   2880

ccgtcttctc cctcctgtgg gtcaagatcg acccattcgt tggaggaacc gagaccgtca   2940

acaccaacaa ctgcaacaca catctgctga ttcaccatcg gtcagctgct gtcgtgccgc   3000

ggcggacgtg tttctggtgt tgcaaacgtg ggttgcctgc ctgatgcggg tctcctctgt   3060

ctatctcgca tctgggcttt tgccccagga tctgaagcgg gtggtgtagg ttagctttat   3120

tttgcgtcca agtgttgatt gatgttgtct gtgttatgaa aagttttggt ggtgaaacct   3180

gaaatgttaa aattcggctc aattgtgaga aaaaaaaaaa aaaaaaaaaa a            3231
```

<210> SEQ ID NO 28
<211> LENGTH: 1007
<212> TYPE: PRT
<213> ORGANISM: Zea mays

<400> SEQUENCE: 28

```
Met Met Glu Ser Ala Ala Ala Gln Ser Cys Ala Ala Cys Gly Asp Asp
 1               5                  10                  15

Ala Arg Ala Ala Cys Arg Ala Cys Ser Tyr Ala Leu Cys Arg Ala Cys
            20                  25                  30

Leu Asp Glu Asp Ala Ala Glu Gly Arg Thr Thr Cys Ala Arg Cys Gly
        35                  40                  45

Gly Asp Tyr Ala Ala Ile Asn Pro Ala Arg Ala Ser Glu Gly Thr Glu
    50                  55                  60

Ala Glu Glu Glu Val Val Glu Asn His His Thr Ala Gly Gly Leu Arg
65                  70                  75                  80

Glu Arg Val Thr Met Gly Ser His Leu Asn Asp Arg Gln Asp Glu Val
                85                  90                  95

Ser His Ala Arg Thr Met Ser Ser Leu Ser Gly Ile Gly Ser Glu Leu
            100                 105                 110

Asn Asp Glu Ser Gly Lys Pro Ile Trp Lys Asn Arg Val Glu Ser Trp
        115                 120                 125

Lys Glu Lys Lys Asn Glu Lys Lys Ala Ser Ala Lys Lys Thr Ala Ala
    130                 135                 140

Lys Ala Gln Pro Pro Pro Val Glu Glu Gln Ile Met Asp Glu Lys Asp
145                 150                 155                 160

Leu Thr Asp Ala Tyr Glu Pro Leu Ser Arg Val Ile Pro Ile Ser Lys
                165                 170                 175

Asn Lys Leu Thr Pro Tyr Arg Ala Val Ile Ile Met Arg Leu Ile Val
            180                 185                 190

Leu Gly Leu Phe Phe His Tyr Arg Ile Thr Asn Pro Val Asn Ser Ala
        195                 200                 205

Phe Gly Leu Trp Met Thr Ser Val Ile Cys Glu Ile Trp Phe Gly Phe
    210                 215                 220

Ser Trp Ile Leu Asp Gln Phe Pro Lys Trp Tyr Pro Ile Asn Arg Glu
225                 230                 235                 240

Thr Tyr Val Asp Arg Leu Ile Ala Arg Tyr Gly Asp Gly Glu Glu Ser
                245                 250                 255

Gly Leu Ala Pro Val Asp Phe Phe Val Ser Thr Val Asp Pro Leu Lys
            260                 265                 270

Glu Pro Pro Leu Ile Thr Ala Asn Thr Val Leu Ser Ile Leu Ala Val
        275                 280                 285

Asp Tyr Pro Val Glu Lys Ile Ser Cys Tyr Val Ser Asp Asp Gly Ser
    290                 295                 300

Ala Met Leu Thr Phe Glu Ser Leu Ala Glu Thr Ala Glu Tyr Ala Arg
305                 310                 315                 320

Lys Trp Val Pro Phe Cys Lys Lys Tyr Ala Ile Glu Pro Arg Ala Pro
                325                 330                 335

Glu Phe Tyr Phe Ser Gln Lys Ile Asp Tyr Leu Lys Asp Lys Ile His
            340                 345                 350

Pro Ser Phe Val Lys Glu Arg Arg Ala Met Lys Arg Asp Tyr Glu Glu
        355                 360                 365

Tyr Lys Val Arg Ile Asn Ala Leu Val Ala Lys Ala Gln Lys Thr Pro
    370                 375                 380

Asp Glu Gly Trp Ile Met Gln Asp Gly Thr Pro Trp Pro Gly Asn Asn
385                 390                 395                 400

Pro Arg Asp His Pro Gly Met Ile Gln Val Phe Leu Gly Glu Thr Gly
                405                 410                 415

Ala Arg Asp Phe Asp Gly Asn Glu Leu Pro Arg Leu Val Tyr Val Ser
```

```
            420                 425                 430

Arg Glu Lys Arg Pro Gly Tyr Gln His His Lys Lys Ala Gly Ala Met
        435                 440                 445

Asn Ala Leu Val Arg Val Ser Ala Val Leu Thr Asn Ala Pro Tyr Ile
    450                 455                 460

Leu Asn Leu Asp Cys Asp His Tyr Val Asn Asn Ser Lys Ala Val Arg
465                 470                 475                 480

Glu Ala Met Cys Phe Met Met Asp Pro Thr Val Gly Arg Asp Val Cys
                485                 490                 495

Tyr Val Gln Phe Pro Gln Arg Phe Asp Gly Ile Asp Arg Ser Asp Arg
            500                 505                 510

Tyr Ala Asn Arg Asn Val Val Phe Phe Asp Val Asn Met Lys Gly Leu
        515                 520                 525

Asp Gly Leu Gln Gly Pro Val Tyr Val Gly Thr Gly Cys Cys Phe Asn
    530                 535                 540

Arg Gln Ala Leu Tyr Gly Tyr Gly Pro Pro Ser Leu Pro Ala Leu Pro
545                 550                 555                 560

Lys Ser Ser Ile Cys Ser Trp Cys Cys Cys Cys Cys Pro Lys Lys Lys
                565                 570                 575

Val Glu Arg Ser Glu Arg Glu Ile Asn Arg Asp Ser Arg Arg Glu Asp
            580                 585                 590

Leu Glu Ser Ala Ile Phe Asn Leu Arg Glu Ile Asp Asn Tyr Asp Glu
        595                 600                 605

Tyr Glu Arg Ser Met Leu Ile Ser Gln Met Ser Phe Glu Lys Ser Phe
    610                 615                 620

Gly Leu Ser Ser Val Phe Ile Glu Ser Thr Leu Met Glu Asn Gly Gly
625                 630                 635                 640

Val Pro Glu Ser Ala Asn Pro Ser Thr Leu Ile Lys Glu Ala Ile His
                645                 650                 655

Val Ile Ser Cys Gly Tyr Glu Glu Lys Thr Glu Trp Gly Lys Glu Ile
            660                 665                 670

Gly Trp Ile Tyr Gly Ser Val Thr Glu Asp Ile Leu Thr Gly Phe Lys
        675                 680                 685

Met His Cys Arg Gly Trp Arg Ser Ile Tyr Cys Met Pro Val Arg Pro
    690                 695                 700

Ala Phe Lys Gly Ser Ala Pro Ile Asn Leu Ser Asp Arg Leu His Gln
705                 710                 715                 720

Val Leu Arg Trp Ala Leu Val Ser Val Glu Ile Phe Phe Ser Arg His
                725                 730                 735

Cys Pro Leu Trp Tyr Gly Tyr Gly Gly Gly Arg Leu Lys Trp Leu Gln
            740                 745                 750

Arg Leu Ser Tyr Ile Asn Thr Ile Val Tyr Pro Phe Thr Ser Leu Pro
        755                 760                 765

Leu Val Ala Tyr Cys Cys Leu Pro Ala Ile Cys Leu Leu Thr Gly Lys
    770                 775                 780

Phe Ile Ile Pro Thr Leu Ser Asn Ala Ala Thr Ile Trp Phe Leu Gly
785                 790                 795                 800

Leu Phe Met Ser Ile Ile Val Thr Ser Val Leu Glu Leu Arg Trp Ser
                805                 810                 815

Gly Ile Gly Ile Glu Asp Trp Trp Arg Asn Glu Gln Phe Trp Val Ile
            820                 825                 830

Gly Gly Val Ser Ala His Leu Phe Ala Val Phe Gln Gly Ile Leu Lys
        835                 840                 845
```

```
Met Ile Ala Gly Leu Asp Thr Asn Phe Thr Val Thr Ala Lys Ala Thr
    850                 855                 860

Asp Asp Thr Glu Phe Gly Glu Leu Tyr Leu Phe Lys Trp Thr Thr Val
865                 870                 875                 880

Leu Ile Pro Pro Thr Ser Ile Leu Val Leu Asn Leu Val Gly Val Val
                885                 890                 895

Ala Gly Phe Ser Ala Ala Leu Asn Ser Gly Tyr Glu Ser Trp Gly Pro
            900                 905                 910

Leu Phe Gly Lys Val Phe Phe Ala Met Trp Val Ile Met His Leu Tyr
        915                 920                 925

Pro Phe Leu Lys Gly Leu Met Gly Arg Gln Asn Arg Thr Pro Thr Ile
    930                 935                 940

Val Val Leu Trp Ser Val Leu Leu Ala Ser Val Phe Ser Leu Leu Trp
945                 950                 955                 960

Val Lys Ile Asp Pro Phe Val Gly Gly Thr Glu Thr Val Asn Thr Asn
                965                 970                 975

Asn Cys Asn Thr His Leu Leu Ile His His Arg Ser Ala Ala Val Val
            980                 985                 990

Pro Arg Arg Thr Cys Phe Trp Cys Cys Lys Arg Gly Leu Pro Ala
        995                 1000                1005
```

<210> SEQ ID NO 29
<211> LENGTH: 3028
<212> TYPE: DNA
<213> ORGANISM: Zea mays

<400> SEQUENCE: 29

```
cacgagttca acatcgacga cgagaatcag cagaggcagc tggagggcaa catgcagaac      60

agccagatca ccgaggcgat gctgcacggc aggatgagct acgggagggg ccccgacgac     120

ggcgacggca acaacacccc gcagatcccg cccatcatca ccggctcccg ctccgtgccg     180

gtgagcggtg agtttccgat taccaacggg tatggccacg gcgaggtctc gtcttccctg     240

cacaagcgca tccatccgta ccctgtgtct gagccaggga gtgccaagtg ggacgagaag     300

aaagaagtga gctggaagga gaggatggac gactggaagt ccaagcaggg catcctcggc     360

ggcggcgccg atcccgaaga catggacgcc gacgtggcac tgaacgacga ggcgaggcag     420

ccgctgtcga ggaaggtgtc gatcgcgtcg agcaaggtga acccgtaccg gatggtgatc     480

gtggtgcgtc tcgttgtgct cgccttcttc ctccggtacc gtatcctgca ccccgtcccg     540

gacgccatcg ggctgtggct cgtctccatc atctgcgaga tctggttcgc catctcctgg     600

atcctcgacc agttccccaa gtggttcccc atcgaccgcg agacgtacct cgaccgcctc     660

tccctcaggt acgagaggga aggggagccg tcgctgctgt cggcggtgga cctgttcgtg     720

agcacggtgg acccgctcaa ggagccgccg ctggtgaccg ccaacaccgt gctctccatc     780

ctcgccgtag actaccccgt ggacaaggtc tcctgctacg tctccgacga cggcgcgtcg     840

atgctgacgt tcgagtcgct gtcggagacg gccgagttcg cgcgcaagtg ggtgcccttc     900

tgcaagaagt tcggcatcga gccccgcgcc ccggagttct acttctcgct caaggtcgac     960

tacctcaagg acaaggtgca gcccaccttc gtgcaggagc gccgcgccat gaagagagag    1020

tatgaggagt tcaaggtccg gatcaacgcg ctggtggcca aggccatgaa ggtgccggca    1080

gaggggtgga tcatgaagga cggcacgccg tggcccggga acaacacccg cgaccacccc    1140

ggcatgatcc aggtgttcct gggccacagc ggcggccacg acaccgaggg caacgagctg    1200

ccccgcctcg tgtacgtctc ccgtgagaag cgcccgggat tccagcacca caagaaggcc    1260
```

```
ggcgccatga acgctctgat tcgcgtctcc gccgtgctga ccaacgcgcc attcatgctc   1320

aacttggact gtgatcacta catcaacaac agcaaggcca tccgggaggc catgtgcttc   1380

ctcatggacc ctcaggtcgg ccggaaggtc tgctacgttc agttcccgca gaggttcgac   1440

ggcatcgacg tgcacgaccg atacgctaac aggaacaccg tcttcttcga catcaacatg   1500

aaggggctgg acggcatcca aggcccggtg tacgtcggga cagggtgcgt gttccggcgc   1560

caggcgctct acggctacaa ccctcccaag ggacccaaga ggcccaagat ggtgacctgc   1620

gactgctgcc cgtgcttcgg ccgcaagaag cggaaacacg ccaaggacgg gctgccggag   1680

ggcaccgctg atatgggagt agatagcgac aaggagatgc tcatgtccca catgaacttc   1740

gagaagcggt tcgggcagtc cgcggcgttc gtcacgtcga cgctgatgga ggaaggcggc   1800

gtccctcctt cgtcgagccc cgccgcgctc ctcaaggagg ccatccatgt catcagctgc   1860

ggctacgagg acaagaccga ctgggggctg gagctggggt ggatctacgg gtcgatcacg   1920

gaggacatcc tgacggggtt caagatgcac tgccgcgggt ggcgctccgt gtactgcatg   1980

ccgaagcggg cggcgttcaa ggggtcggcg ccgatcaatc tatcggaccg tctcaaccag   2040

gtgctccggt gggcgctggg gtccgtcgag atcttcttca gccggcacag ccccctgctg   2100

tacggctaca agaacggcaa cctcaagtgg ctggagcgct tcgcctacat caacaccacc   2160

atctacccct tcacctcgct cccgctgctc gcctactgca ccctccccgc cgtctgcctc   2220

ctcaccggca agttcatcat gccgtcgatt agcacgttcg ccagcctctt cttcatcgcc   2280

ctcttcatgt ccatcttcgc gacgggcatc ctggagatgc ggtggagcgg ggtgagcatc   2340

gaggagtggt ggaggaacga gcagttctgg gtcatcggcg gcgtgtccgc gcatctcttc   2400

gccgtcgtgc agggcctgct caaggtcctc gccgggatcg acaccaactt caccgtcacc   2460

tccaaggcca ccggcgacga ggacgacgag ttcgccgagc tctacgcctt caagtggacc   2520

acgctcctca tcccgcccac cacgctgctc atcattaacg tcatcggcgt cgtggccggc   2580

atctccgacg ccatcaacaa cgggtaccag tcctgggggc ccctcttcgg caagctcttc   2640

ttcgccttct gggtcatcgt ccacctctac ccgttcctca aggggctcat ggggcgccag   2700

aacaggacgc ccaccgttgt tgtcatctgg tccattctgc tggcctccat cttctccctg   2760

ctctgggtca ggatcgaccc tttcatcgtc aggaccaagg gcccggacgt caggcagtgt   2820

ggcatcaatt gctgagctgt ttattaaggt tcaaaattct ggagcttgtg catagggaga   2880

aaaaaacaat ttagaaattt tgtaaggttg ttgtgtctgt aatgttatgg tacccagaat   2940

tgtcggacga ggaattgaac aaaggacaag gtttgattgt taaatggcaa aaaaaaaaaa   3000

aaaaaaaaaa aaaaaaaaaa aaaaaaaa                                      3028
```

<210> SEQ ID NO 30
<211> LENGTH: 927
<212> TYPE: PRT
<213> ORGANISM: Zea mays

<400> SEQUENCE: 30

```
Met Gln Asn Ser Gln Ile Thr Glu Ala Met Leu His Gly Arg Met Ser
 1               5                  10                  15

Tyr Gly Arg Gly Pro Asp Asp Gly Asp Gly Asn Asn Thr Pro Gln Ile
            20                  25                  30

Pro Pro Ile Ile Thr Gly Ser Arg Ser Val Pro Val Ser Gly Glu Phe
        35                  40                  45

Pro Ile Thr Asn Gly Tyr Gly His Gly Glu Val Ser Ser Ser Leu His
    50                  55                  60
```

-continued

```
Lys Arg Ile His Pro Tyr Pro Val Ser Glu Pro Gly Ser Ala Lys Trp
65                  70                  75                  80

Asp Glu Lys Lys Glu Val Ser Trp Lys Glu Arg Met Asp Asp Trp Lys
                85                  90                  95

Ser Lys Gln Gly Ile Leu Gly Gly Gly Ala Asp Pro Glu Asp Met Asp
            100                 105                 110

Ala Asp Val Ala Leu Asn Asp Glu Ala Arg Gln Pro Leu Ser Arg Lys
        115                 120                 125

Val Ser Ile Ala Ser Ser Lys Val Asn Pro Tyr Arg Met Val Ile Val
    130                 135                 140

Val Arg Leu Val Val Leu Ala Phe Phe Leu Arg Tyr Arg Ile Leu His
145                 150                 155                 160

Pro Val Pro Asp Ala Ile Gly Leu Trp Leu Val Ser Ile Ile Cys Glu
                165                 170                 175

Ile Trp Phe Ala Ile Ser Trp Ile Leu Asp Gln Phe Pro Lys Trp Phe
            180                 185                 190

Pro Ile Asp Arg Glu Thr Tyr Leu Asp Arg Leu Ser Leu Arg Tyr Glu
        195                 200                 205

Arg Glu Gly Glu Pro Ser Leu Leu Ser Ala Val Asp Leu Phe Val Ser
    210                 215                 220

Thr Val Asp Pro Leu Lys Glu Pro Pro Leu Val Thr Ala Asn Thr Val
225                 230                 235                 240

Leu Ser Ile Leu Ala Val Asp Tyr Pro Val Asp Lys Val Ser Cys Tyr
                245                 250                 255

Val Ser Asp Asp Gly Ala Ser Met Leu Thr Phe Glu Ser Leu Ser Glu
            260                 265                 270

Thr Ala Glu Phe Ala Arg Lys Trp Val Pro Phe Cys Lys Lys Phe Gly
        275                 280                 285

Ile Glu Pro Arg Ala Pro Glu Phe Tyr Phe Ser Leu Lys Val Asp Tyr
    290                 295                 300

Leu Lys Asp Lys Val Gln Pro Thr Phe Val Gln Glu Arg Arg Ala Met
305                 310                 315                 320

Lys Arg Glu Tyr Glu Glu Phe Lys Val Arg Ile Asn Ala Leu Val Ala
                325                 330                 335

Lys Ala Met Lys Val Pro Ala Glu Gly Trp Ile Met Lys Asp Gly Thr
            340                 345                 350

Pro Trp Pro Gly Asn Asn Thr Arg Asp His Pro Gly Met Ile Gln Val
        355                 360                 365

Phe Leu Gly His Ser Gly Gly His Asp Thr Glu Gly Asn Glu Leu Pro
    370                 375                 380

Arg Leu Val Tyr Val Ser Arg Glu Lys Arg Pro Gly Phe Gln His His
385                 390                 395                 400

Lys Lys Ala Gly Ala Met Asn Ala Leu Ile Arg Val Ser Ala Val Leu
                405                 410                 415

Thr Asn Ala Pro Phe Met Leu Asn Leu Asp Cys Asp His Tyr Ile Asn
            420                 425                 430

Asn Ser Lys Ala Ile Arg Glu Ala Met Cys Phe Leu Met Asp Pro Gln
        435                 440                 445

Val Gly Arg Lys Val Cys Tyr Val Gln Phe Pro Gln Arg Phe Asp Gly
    450                 455                 460

Ile Asp Val His Asp Arg Tyr Ala Asn Arg Asn Thr Val Phe Phe Asp
465                 470                 475                 480

Ile Asn Met Lys Gly Leu Asp Gly Ile Gln Gly Pro Val Tyr Val Gly
                485                 490                 495
```

```
Thr Gly Cys Val Phe Arg Arg Gln Ala Leu Tyr Gly Tyr Asn Pro Pro
            500                 505                 510

Lys Gly Pro Lys Arg Pro Lys Met Val Thr Cys Asp Cys Cys Pro Cys
        515                 520                 525

Phe Gly Arg Lys Lys Arg Lys His Ala Lys Asp Gly Leu Pro Glu Gly
    530                 535                 540

Thr Ala Asp Met Gly Val Asp Ser Asp Lys Glu Met Leu Met Ser His
545                 550                 555                 560

Met Asn Phe Glu Lys Arg Phe Gly Gln Ser Ala Ala Phe Val Thr Ser
                565                 570                 575

Thr Leu Met Glu Glu Gly Gly Val Pro Pro Ser Ser Ser Pro Ala Ala
            580                 585                 590

Leu Leu Lys Glu Ala Ile His Val Ile Ser Cys Gly Tyr Glu Asp Lys
        595                 600                 605

Thr Asp Trp Gly Leu Glu Leu Gly Trp Ile Tyr Gly Ser Ile Thr Glu
    610                 615                 620

Asp Ile Leu Thr Gly Phe Lys Met His Cys Arg Gly Trp Arg Ser Val
625                 630                 635                 640

Tyr Cys Met Pro Lys Arg Ala Ala Phe Lys Gly Ser Ala Pro Ile Asn
                645                 650                 655

Leu Ser Asp Arg Leu Asn Gln Val Leu Arg Trp Ala Leu Gly Ser Val
            660                 665                 670

Glu Ile Phe Phe Ser Arg His Ser Pro Leu Leu Tyr Gly Tyr Lys Asn
        675                 680                 685

Gly Asn Leu Lys Trp Leu Glu Arg Phe Ala Tyr Ile Asn Thr Thr Ile
    690                 695                 700

Tyr Pro Phe Thr Ser Leu Pro Leu Leu Ala Tyr Cys Thr Leu Pro Ala
705                 710                 715                 720

Val Cys Leu Leu Thr Gly Lys Phe Ile Met Pro Ser Ile Ser Thr Phe
                725                 730                 735

Ala Ser Leu Phe Phe Ile Ala Leu Phe Met Ser Ile Phe Ala Thr Gly
            740                 745                 750

Ile Leu Glu Met Arg Trp Ser Gly Val Ser Ile Glu Glu Trp Trp Arg
        755                 760                 765

Asn Glu Gln Phe Trp Val Ile Gly Gly Val Ser Ala His Leu Phe Ala
    770                 775                 780

Val Val Gln Gly Leu Leu Lys Val Leu Ala Gly Ile Asp Thr Asn Phe
785                 790                 795                 800

Thr Val Thr Ser Lys Ala Thr Gly Asp Glu Asp Asp Glu Phe Ala Glu
                805                 810                 815

Leu Tyr Ala Phe Lys Trp Thr Thr Leu Leu Ile Pro Pro Thr Thr Leu
            820                 825                 830

Leu Ile Ile Asn Val Ile Gly Val Val Ala Gly Ile Ser Asp Ala Ile
        835                 840                 845

Asn Asn Gly Tyr Gln Ser Trp Gly Pro Leu Phe Gly Lys Leu Phe Phe
    850                 855                 860

Ala Phe Trp Val Ile Val His Leu Tyr Pro Phe Leu Lys Gly Leu Met
865                 870                 875                 880

Gly Arg Gln Asn Arg Thr Pro Thr Val Val Val Ile Trp Ser Ile Leu
                885                 890                 895

Leu Ala Ser Ile Phe Ser Leu Leu Trp Val Arg Ile Asp Pro Phe Ile
            900                 905                 910

Val Arg Thr Lys Gly Pro Asp Val Arg Gln Cys Gly Ile Asn Cys
```

915 920 925

<210> SEQ ID NO 31
<211> LENGTH: 36
<212> TYPE: DNA
<213> ORGANISM: Artificial Sequence
<220> FEATURE:
<223> OTHER INFORMATION: Sal-A20 oligonucleotide

<400> SEQUENCE: 31
tcgacccacg cgtccgaaaa aaaaaaaaaa aaaaaa 36

<210> SEQ ID NO 32
<211> LENGTH: 28
<212> TYPE: DNA
<213> ORGANISM: Artificial Sequence
<220> FEATURE:
<223> OTHER INFORMATION: GSP1 forward primer

<400> SEQUENCE: 32
tacgatgagt acgagaggtc catgctca 28

<210> SEQ ID NO 33
<211> LENGTH: 26
<212> TYPE: DNA
<213> ORGANISM: Artificial Sequence
<220> FEATURE:
<223> OTHER INFORMATION: GSP2 reverse primer

<400> SEQUENCE: 33
ggcaaaagcc cagatgcgag atagac 26

<210> SEQ ID NO 34
<211> LENGTH: 32
<212> TYPE: DNA
<213> ORGANISM: Artificial Sequence
<220> FEATURE:
<223> OTHER INFORMATION: Mu TIR primer

<400> SEQUENCE: 34
agagaagcca acgccawcgc ctcyatttcg tc 32

<210> SEQ ID NO 35
<211> LENGTH: 9
<212> TYPE: DNA
<213> ORGANISM: Zea mays

<400> SEQUENCE: 35 tggcggccg 9

<210> SEQ ID NO 36
<211> LENGTH: 9
<212> TYPE: DNA
<213> ORGANISM: Zea mays

<400> SEQUENCE: 36 tctgaaatg 9

<210> SEQ ID NO 37
<211> LENGTH: 9
<212> TYPE: DNA
<213> ORGANISM: Zea mays

<400> SEQUENCE: 37 gcccacaag 9

<210> SEQ ID NO 38
<211> LENGTH: 9
<212> TYPE: DNA
<213> ORGANISM: Zea mays

<400> SEQUENCE: 38 catcctggt 9

<210> SEQ ID NO 39
<211> LENGTH: 9
<212> TYPE: DNA
<213> ORGANISM: Zea mays

<400> SEQUENCE: 39 gtgttcttc 9

<210> SEQ ID NO 40
<211> LENGTH: 9
<212> TYPE: DNA
<213> ORGANISM: Zea mays

<400> SEQUENCE: 40 gccatgtgg 9

<210> SEQ ID NO 41
<211> LENGTH: 3568
<212> TYPE: DNA
<213> ORGANISM: Zea mays
<220> FEATURE:
<221> NAME/KEY: misc_feature
<222> LOCATION: 3487
<223> OTHER INFORMATION: n = A,T,C or G

<400> SEQUENCE: 41
gtcgacccac gcgtccggag ctcgtcgtca tccgccgcga tggcgagcca gggccgaagc 60
ccatggacca gcggaacggc caggtgtgcc agatttgcgg cgacgacgtg ggcgcaacc 120 ccgacgggga gcctttcgtg gcctgcaacg agtgcgcctt ccccatctgc cgggactgct 180
acgagtacga gcgccgcgag ggcacgcaga actgccccca gtgcaagacc cgcttcaagc 240
gcttcaaggg gtgcgcgcgc gtgcccgggg acgaggagga ggacggcgtc gacgacctgg 300
agaacgagtt caactggagc gacaagcacg actcccagta cctcgccgag tccatgctcc 360
acgcccacat gagctacggc cgcggcgccg acctcgacgg cgtgccgcag ccattccacc 420
ccatccccaa tgttcccctc ctcaccaacg gacagatggt cgatgacatc ccgccggacc 480
agcacgccct tgtgccctcg ttcgtgggtg gcggggggaa gaggattcac cctctcccgt 540
acgcggatcc caaccttcct gtgcaaccga ggtctatgga cccttccaag gatctcgccg 600
catatggcta cgggagcgta gcatggaagg agaggatgga gagctggaag cagaagcagg 660
agaggatgca ccagacgagg aacgatggcg gcggcgatga tggtgatgat gcagatctac 720
cactaatgga tgaagctaga cagccattgt ccagaaagat cccgcttcct tcaagccaaa 780
tcaaccccta taggatgatt ataataattc ggctagtggt tttgtgtttc ttcttccact 840
accgagtgat gcatccggtg cctgatgcat ttgctttatg gctcatatct gtgatctgtg 900
aaatttggtt tgccatgtct tggattcttg accagtttcc aaagtggttt cctatcgaga 960
gggaaaccta tcttgaccgg ctgagtttaa ggtttgacaa ggaagggcat ccttctcaac 1020
tcgcccctgt tgatttcttt gtcagtacgg ttgatccctt gaaggaacct ccattggtca 1080
ctgctaatac tgttctatct atcctttcgg tggattatcc agttgataag gtttcatgct 1140

-continued

```
acgtttctga tgatggtgct gccatgctga catttgaagc attgtctgaa acatctgaat   1200
ttgcaaagaa atgggttcct ttctgcaaaa gatatagcct tgagcctcgt gctccagagt   1260
ggtacttcca acagaagata gactacctga aagacaaggt ggcgccaaac tttgttagag   1320
aacggagagc aatgaagaga gagtatgagg aattcaaggt cagaatcaat gccttggttg   1380
ctaaagccca aaaggttcct gaggaaggat ggacaatgca ggatggaact ccatggcccg   1440
gaaataatgt ccgtgatcat cctggaatga ttcaggtttt ccttggtcaa agtggtggcc   1500
atgatgtgga aggaaatgag ctgcctcgat tggtttatgt ttcaagagaa aaacggccag   1560
gctacaacca tcacaagaag gctggtgcta tgaatgcatt ggtccgagtc tctgctgtac   1620
taactaatgc tccttatttg ctgaacttgg attgtgatca ctatatcaat aatagtaagg   1680
ctataaagga agcaatgtgt tttatgatgg atcctttgct tggaaagaaa gtttgctatg   1740
tgcagtttcc tcaaagattt gatgggattg atcgccatga tcgatatgct aacagaaatg   1800
ttgtcttttt cgatatcaac atgaaaggtt tggatggtat ccagggccca atttatgtgg   1860
gtactggatg tgtcttcaga aggcaggcat tatatggcta cgatgctccc aaaacaaaga   1920
agccaccatc aagaacttgc aactgctggc caaagtggtg catttgctgt tgctgttttg   1980
gtaacaggaa gaccaagaag aagaccaaga cctctaaacc taaatttgag aagataaaga   2040
aactttttaa gaaaaaggaa aatcaagccc ctgcatatgc tcttggtgaa attgatgaag   2100
ccgctccagg agctgaaaat gaaaaggcta gtattgtaaa tcaacagaag ttggaaaaga   2160
aatttggcca gtcttcagtt tttgttgcat ccacacttct tgagaatggt ggaaccctga   2220
agagtgccag tccagcttct cttctgaagg aagctataca tgtcatcagt tgtggatatg   2280
aagacaaaac aggctgggga aaagatattg gttggattta tggatcagtc acagaagata   2340
ttcttactgg gtttaagatg cactgccatg gttggcggtc aatttactgc atacctaaac   2400
gggccgcctt caaaggttcc gcacctctca atctttccga tcgttttcac caggttcttc   2460
ggtgggctct tggttcaatt gaaattttgt tcagcaacca ctgccctctc tggtatgggt   2520
atggtggtgg actaaagttc ctggaaaggt ttccgtacat taactccatc gtataccctt   2580
ggacatctat cccgctcttg gcctattgca cattgcctgc catctgcttg ctgacaggga   2640
aatttatcac gccagagctt aacaatgttg ccagcctctg gttcatgtca cttttcatct   2700
gcatttttgc tacgagcatc ctggaaatga gatggagtgg tgtaggcatc gatgactggt   2760
ggagaaacga gcagttttgg gtcattggag gcgtgtcttc acatctcttt gctgtgttcc   2820
agggactcct caaggtcata gctggtgtag acacgagctt cactgtgaca tccaagggcg   2880
gagacgacga ggagttctca gagctgtaca cattcaaatg gacgaccctt ctgatacctc   2940
cgacaaccct gctcctactg aacttcattg gagtggtagc tggcatctcc aatgcgatca   3000
acaacggata tgaatcatgg ggccccctgt tcgggaagct cttctttgca ttttgggtga   3060
tcgtccatct ttacccgttc ctcaagggtc tggttgggag gcagaacagg acgccaacga   3120
ttgtcattgt ctggtccatc ctcctggctt cgatcttctc gctgctttgg gtccggatcg   3180
acccgttcct tgcgaaggat gatggtcccc tgttggagga gtgtggtctg gattgcaact   3240
aggaggtcag cacgtggact tccccgtcag tgtgtggtcg aagaagtatt tttgcagatg   3300
ttttgtgccc atatttcttt actcaatttt tgtccctctg tagattgaaa caaggggtga   3360
aggggaaaaa aagtacttgt atttcttttg ttccatggtg gtggtggtgg tgggcggctc   3420
agcctcgtga gtgcaatatt gggcaaaccg gaggttgcgg caaccttgtg cagttcgtcc   3480
acgaatntac tagggatgat cgcgaccaat caatcaatcg atgaccgagt tcaattgttc   3540
```

```
aaaaaaaaaa aaaaaaaagg gcggccgc                                      3568


<210> SEQ ID NO 42
<211> LENGTH: 1059
<212> TYPE: PRT
<213> ORGANISM: Zea mays

<400> SEQUENCE: 42

Met Asp Gln Arg Asn Gly Gln Val Cys Gln Ile Cys Gly Asp Asp Val
 1               5                  10                  15

Gly Arg Asn Pro Asp Gly Glu Pro Phe Val Ala Cys Asn Glu Cys Ala
            20                  25                  30

Phe Pro Ile Cys Arg Asp Cys Tyr Glu Tyr Glu Arg Arg Glu Gly Thr
        35                  40                  45

Gln Asn Cys Pro Gln Cys Lys Thr Arg Phe Lys Arg Phe Lys Gly Cys
    50                  55                  60

Ala Arg Val Pro Gly Asp Glu Glu Glu Asp Gly Val Asp Asp Leu Glu
65                  70                  75                  80

Asn Glu Phe Asn Trp Ser Asp Lys His Asp Ser Gln Tyr Leu Ala Glu
                85                  90                  95

Ser Met Leu His Ala His Met Ser Tyr Gly Arg Gly Ala Asp Leu Asp
            100                 105                 110

Gly Val Pro Gln Pro Phe His Pro Ile Pro Asn Val Pro Leu Leu Thr
        115                 120                 125

Asn Gly Gln Met Val Asp Asp Ile Pro Pro Asp Gln His Ala Leu Val
    130                 135                 140

Pro Ser Phe Val Gly Gly Gly Gly Lys Arg Ile His Pro Leu Pro Tyr
145                 150                 155                 160

Ala Asp Pro Asn Leu Pro Val Gln Pro Arg Ser Met Asp Pro Ser Lys
                165                 170                 175

Asp Leu Ala Ala Tyr Gly Tyr Gly Ser Val Ala Trp Lys Glu Arg Met
            180                 185                 190

Glu Ser Trp Lys Gln Lys Gln Glu Arg Met His Gln Thr Arg Asn Asp
        195                 200                 205

Gly Gly Gly Asp Asp Gly Asp Asp Ala Asp Leu Pro Leu Met Asp Glu
    210                 215                 220

Ala Arg Gln Pro Leu Ser Arg Lys Ile Pro Leu Pro Ser Ser Gln Ile
225                 230                 235                 240

Asn Pro Tyr Arg Met Ile Ile Ile Ile Arg Leu Val Val Leu Cys Phe
                245                 250                 255

Phe Phe His Tyr Arg Val Met His Pro Val Pro Asp Ala Phe Ala Leu
            260                 265                 270

Trp Leu Ile Ser Val Ile Cys Glu Ile Trp Phe Ala Met Ser Trp Ile
        275                 280                 285

Leu Asp Gln Phe Pro Lys Trp Phe Pro Ile Glu Arg Glu Thr Tyr Leu
    290                 295                 300

Asp Arg Leu Ser Leu Arg Phe Asp Lys Glu Gly His Pro Ser Gln Leu
305                 310                 315                 320

Ala Pro Val Asp Phe Phe Val Ser Thr Val Asp Pro Leu Lys Glu Pro
                325                 330                 335

Pro Leu Val Thr Ala Asn Thr Val Leu Ser Ile Leu Ser Val Asp Tyr
            340                 345                 350

Pro Val Asp Lys Val Ser Cys Tyr Val Ser Asp Asp Gly Ala Ala Met
        355                 360                 365

Leu Thr Phe Glu Ala Leu Ser Glu Thr Ser Glu Phe Ala Lys Lys Trp
```

```
    370                 375                 380

Val Pro Phe Cys Lys Arg Tyr Ser Leu Glu Pro Arg Ala Pro Glu Trp
385                 390                 395                 400

Tyr Phe Gln Gln Lys Ile Asp Tyr Leu Lys Asp Lys Val Ala Pro Asn
                405                 410                 415

Phe Val Arg Glu Arg Arg Ala Met Lys Arg Glu Tyr Glu Glu Phe Lys
            420                 425                 430

Val Arg Ile Asn Ala Leu Val Ala Lys Ala Gln Lys Val Pro Glu Glu
        435                 440                 445

Gly Trp Thr Met Gln Asp Gly Thr Pro Trp Pro Gly Asn Asn Val Arg
    450                 455                 460

Asp His Pro Gly Met Ile Gln Val Phe Leu Gly Gln Ser Gly Gly His
465                 470                 475                 480

Asp Val Glu Gly Asn Glu Leu Pro Arg Leu Val Tyr Val Ser Arg Glu
                485                 490                 495

Lys Arg Pro Gly Tyr Asn His His Lys Lys Ala Gly Ala Met Asn Ala
            500                 505                 510

Leu Val Arg Val Ser Ala Val Leu Thr Asn Ala Pro Tyr Leu Leu Asn
        515                 520                 525

Leu Asp Cys Asp His Tyr Ile Asn Asn Ser Lys Ala Ile Lys Glu Ala
    530                 535                 540

Met Cys Phe Met Met Asp Pro Leu Leu Gly Lys Lys Val Cys Tyr Val
545                 550                 555                 560

Gln Phe Pro Gln Arg Phe Asp Gly Ile Asp Arg His Asp Arg Tyr Ala
                565                 570                 575

Asn Arg Asn Val Val Phe Phe Asp Ile Asn Met Lys Gly Leu Asp Gly
            580                 585                 590

Ile Gln Gly Pro Ile Tyr Val Gly Thr Gly Cys Val Phe Arg Arg Gln
        595                 600                 605

Ala Leu Tyr Gly Tyr Asp Ala Pro Lys Thr Lys Lys Pro Pro Ser Arg
    610                 615                 620

Thr Cys Asn Cys Trp Pro Lys Trp Cys Ile Cys Cys Cys Cys Phe Gly
625                 630                 635                 640

Asn Arg Lys Thr Lys Lys Lys Thr Lys Thr Ser Lys Pro Lys Phe Glu
                645                 650                 655

Lys Ile Lys Lys Leu Phe Lys Lys Lys Glu Asn Gln Ala Pro Ala Tyr
            660                 665                 670

Ala Leu Gly Glu Ile Asp Glu Ala Ala Pro Gly Ala Glu Asn Glu Lys
        675                 680                 685

Ala Ser Ile Val Asn Gln Gln Lys Leu Glu Lys Lys Phe Gly Gln Ser
    690                 695                 700

Ser Val Phe Val Ala Ser Thr Leu Leu Glu Asn Gly Gly Thr Leu Lys
705                 710                 715                 720

Ser Ala Ser Pro Ala Ser Leu Leu Lys Glu Ala Ile His Val Ile Ser
                725                 730                 735

Cys Gly Tyr Glu Asp Lys Thr Gly Trp Gly Lys Asp Ile Gly Trp Ile
            740                 745                 750

Tyr Gly Ser Val Thr Glu Asp Ile Leu Thr Gly Phe Lys Met His Cys
        755                 760                 765

His Gly Trp Arg Ser Ile Tyr Cys Ile Pro Lys Arg Ala Ala Phe Lys
    770                 775                 780

Gly Ser Ala Pro Leu Asn Leu Ser Asp Arg Phe His Gln Val Leu Arg
785                 790                 795                 800
```

```
Trp Ala Leu Gly Ser Ile Glu Ile Leu Phe Ser Asn His Cys Pro Leu
                805                 810                 815

Trp Tyr Gly Tyr Gly Gly Gly Leu Lys Phe Leu Glu Arg Phe Ser Tyr
            820                 825                 830

Ile Asn Ser Ile Val Tyr Pro Trp Thr Ser Ile Pro Leu Leu Ala Tyr
        835                 840                 845

Cys Thr Leu Pro Ala Ile Cys Leu Leu Thr Gly Lys Phe Ile Thr Pro
    850                 855                 860

Glu Leu Asn Asn Val Ala Ser Leu Trp Phe Met Ser Leu Phe Ile Cys
865                 870                 875                 880

Ile Phe Ala Thr Ser Ile Leu Glu Met Arg Trp Ser Gly Val Gly Ile
                885                 890                 895

Asp Asp Trp Trp Arg Asn Glu Gln Phe Trp Val Ile Gly Gly Val Ser
            900                 905                 910

Ser His Leu Phe Ala Val Phe Gln Gly Leu Leu Lys Val Ile Ala Gly
        915                 920                 925

Val Asp Thr Ser Phe Thr Val Thr Ser Lys Gly Gly Asp Asp Glu Glu
    930                 935                 940

Phe Ser Glu Leu Tyr Thr Phe Lys Trp Thr Thr Leu Leu Ile Pro Pro
945                 950                 955                 960

Thr Thr Leu Leu Leu Leu Asn Phe Ile Gly Val Val Ala Gly Ile Ser
                965                 970                 975

Asn Ala Ile Asn Asn Gly Tyr Glu Ser Trp Gly Pro Leu Phe Gly Lys
            980                 985                 990

Leu Phe Phe Ala Phe Trp Val Ile Val His Leu Tyr Pro Phe Leu Lys
        995                 1000                1005

Gly Leu Val Gly Arg Gln Asn Arg Thr Pro Thr Ile Val Ile Val Trp
    1010                1015                1020

Ser Ile Leu Leu Ala Ser Ile Phe Ser Leu Leu Trp Val Arg Ile Asp
1025                1030                1035                1040

Pro Phe Leu Ala Lys Asp Asp Gly Pro Leu Leu Glu Glu Cys Gly Leu
                1045                1050                1055

Asp Cys Asn
```

<210> SEQ ID NO 43
<211> LENGTH: 25
<212> TYPE: DNA
<213> ORGANISM: Artificial Sequence
<220> FEATURE:
<223> OTHER INFORMATION: amplicon

<400> SEQUENCE: 43
atggaccagc ggaacggcca ggtgt 25

<210> SEQ ID NO 44
<211> LENGTH: 25
<212> TYPE: DNA
<213> ORGANISM: Artificial Sequence
<220> FEATURE:
<223> OTHER INFORMATION: amplicon

<400> SEQUENCE: 44
ctagttgcaa tccagaccac actcc 25

<210> SEQ ID NO 45
<211> LENGTH: 3725
<212> TYPE: DNA
<213> ORGANISM: Zea mays

<400> SEQUENCE: 45

```
gcagcagcag caccaccact gcgcggcatt gcagcgagca agcgggaggg atctggggca     60
tggtggcggt cgctgccgct gccgctcgga tctagagggc cgcacgggct gattgccctc    120
cgccggcctc gtcggtgtcg gtggagtgtg aatcggtgtg tgtaggagga gcgcggagat    180
ggcggccaac aaggggatgg tggcaggctc tcacaaccgc aacgagttcg tcatgatccg    240
ccacgacggc gacgcgcctg tcccggctaa gcccacgaag agtgcgaatg ggcaggtctg    300
ccagatttgt ggcgacactg ttggcgtttc agccactggt gatgtctttg ttgcctgcaa    360
tgagtgtgcc ttccctgtct gccgcccttg ctatgagtac gagcgcaagg aagggaacca    420
atgctgccct cagtgcaaga ctagatacaa gagacagaaa ggtagccctc gagttcatgg    480
tgatgatgag gaggaagatg ttgatgacct ggacaatgaa ttcaactata agcaaggcaa    540
tgggaagggc ccagagtggc agcttcaagg agatgacgct gatctgtctt catctgctcg    600
ccatgaccca caccatcgga ttccacgcct tacaagtgga caacagatat ctggagagat    660
ccctgatgca tcccctgacc gtcattctat ccgcagtcca acatcgagct atgttgatcc    720
aagcgttcca gttcctgtga ggattgtgga cccctcgaag gacttgaatt cctatgggct    780
taatagtgtt gactggaagg aaagagttga gagctggagg gttaaacagg acaaaaatat    840
gttgcaagtg actaataaat atccagaggc tagaggagac atggagggga ctggctcaaa    900
tggagaagat atgcaaatgg ttgatgatgc acgcctacct ttgagccgca ttgtgccaat    960
ttcctcaaac cagctcaacc tttaccggat agtaatcatt ctccgtctta tcatcctgtg   1020
cttcttcttc caatatcgta tcagtcatcc agtgcgtaat gcttatggat tgtggctagt   1080
atctgttatc tgtgaggtct ggtttgcctt gtcctggctt ctagatcagt tcccaaaatg   1140
gtatccaatc aaccgtgaga catatctcga caggcttgca ttgaggtatg atagagaggg   1200
agagccatca cagctggctc ccattgatgt ctttgtcagt acagtggatc cattgaagga   1260
acctccactg atcacagcca acactgtttt gtccattctt gctgtggatt accctgttga   1320
caaagtgtca tgctatgttt ctgatgatgg ctcagctatg ctgacttttg agtctctctc   1380
tgaaactgcc gaatttgcta gaaagtgggt tccctttttgt aagaagcaca atattgaacc   1440
aagagctcca gaattttact ttgctcaaaa aatagattac ctgaaggaca aaattcaacc   1500
ttcatttgtt aaggaaagac gagcaatgaa gagagagtat gaagaattca aaataagaat   1560
caatgccctt gttgccaaag cacagaaagt gcctgaagag gggtggacca tggctgatgg   1620
aactgcttgg cctgggaata accctaggga ccatcctggc atgattcagg tgttcttggg   1680
gcacagtggt gggcttgaca ctgatggaaa tgaattacca cgtcttgtct atgtctctcg   1740
tgaaaagaga ccaggctttc agcatcacaa gaaggctggt gcaatgaatg cactgattcg   1800
tgtatctgct gtgctgacaa atggtgccta tcttctcaat gtggattgtg accattactt   1860
caatagcagc aaagctctta gagaagcaat gtgcttcatg atggatccag ctctaggaag   1920
gaaaacttgt tatgtacaat ttccacaaag atttgatggc attgacttgc acgatcgata   1980
tgctaatagg aacatagtct tctttgatat caacatgaaa ggtctagatg gcattcaggg   2040
tccagtctat gtgggaacag gatgctgttt caataggcag gctttgtatg gatatgatcc   2100
tgttttgact gaagctgatc tggaacctaa cattgttgtt aagagctgct gtggtagaag   2160
gaagagaaag aacaagagtt atatggatag tcaaagccgt attatgaaga gaacagaatc   2220
ttcagctccc atctttaaca tggaagacat cgaggagggt attgaaggtt atgaggatga   2280
aaggtcagtg cttatgtccc agaggaaatt ggagaaacgc tttggtcagt ctccaatctt   2340
```

```
cattgcatcc acctttatga ctcaaggtgg cataccacct tcaacaaacc cagcttctct   2400

actgaaggaa gctatccatg ttatcagctg tgggtacgag gacaaaactg aatggggaaa   2460

agagattggc tggatctatg gttcagttac agaggatatt ctgactgggt ttaaaatgca   2520

tgcaagaggc tggcaatcaa tctactgcat gccaccacga ccttgtttca agggttctgc   2580

accaatcaat ctttctgatc gtcttaatca ggtgctccgt tgggctcttg ggtcagtgga   2640

aattctgctt agcagacatt gtcctatatg gtatggctac aatgggcgat tgaagctttt   2700

ggagaggctg gcttacatta acaccattgt ttatccaatc acatctgttc cgcttatcgc   2760

ctattgtgtg cttcctgcta tctgtcttct taccaataaa tttatcattc ctgagattag   2820

taattatgct ggaatgttct tcattcttct ttttgcctcc attttcgcaa ctggtatatt   2880

ggagctcaga tggagtggtg ttggcattga agattggtgg agaaatgagc agttttgggt   2940

tattggtggc acctctgccc atctcttcgc ggtgttccag ggtctgctga aagtgttggc   3000

tgggattgat accaacttca cagttacctc aaaggcatct gatgaggatg gcgactttgc   3060

tgagctatat gtgttcaagt ggaccagttt gctcatccct ccgaccactg ttcttgtcat   3120

taacctggtc ggaatggtgg caggaatttc gtatgccatt aacagcggct accaatcctg   3180

gggtccgctc tttggaaagc tgttcttctc gatctgggtg atcctccatc tctacccctt   3240

cctcaagggt ctcatgggca ggcagaaccg cacgccaaca atcgtcatcg tttggtccat   3300

cctccttgcg tctatcttct ccttgctgtg ggtgaagatc gatcctttca tctccccgac   3360

acagaaagct gccgccttgg ggcaatgtgg tgtgaactgc tgatccagat tgtgactctt   3420

atctgaagag gctcagccaa agatctgccc cctcgtgtaa atacctgagg gggctagatg   3480

ggaatttttt gttgtagatg aggatggatc tgcatccaag ttatgcctct gtttattagc   3540

ttcttcggtg ccggtgctgc tgcagacaat catggagcct ttctaccttg cttgtagtgc   3600

tggccagcag cgtaaattgt gaattctgca ttttttttata cgtggtgttt attgttttag   3660

agtaaattat catttgtttg aggtaactat tcacacgaac tatatggcaa tgctgttatt   3720

taaaa                                                                3725
```

<210> SEQ ID NO 46
<211> LENGTH: 1074
<212> TYPE: PRT
<213> ORGANISM: Zea mays

<400> SEQUENCE: 46

```
Met Ala Ala Asn Lys Gly Met Val Ala Gly Ser His Asn Arg Asn Glu
1               5                   10                  15

Phe Val Met Ile Arg His Asp Gly Asp Ala Pro Val Pro Ala Lys Pro
            20                  25                  30

Thr Lys Ser Ala Asn Gly Gln Val Cys Gln Ile Cys Gly Asp Thr Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Asp Glu Glu Glu Asp Val Asp Asp Leu Asp
            100                 105                 110

Asn Glu Phe Asn Tyr Lys Gln Gly Asn Gly Lys Gly Pro Glu Trp Gln
        115                 120                 125
```

```
Leu Gln Gly Asp Asp Ala Asp Leu Ser Ser Ser Ala Arg His Asp Pro
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Leu Gln Val
    210                 215                 220

Thr Asn Lys Tyr Pro Glu Ala Arg Gly Asp Met Glu Gly Thr Gly Ser
225                 230                 235                 240

Asn Gly Glu Asp Met Gln Met Val Asp Asp Ala Arg Leu Pro Leu Ser
                245                 250                 255

Arg Ile Val Pro Ile Ser Ser Asn Gln Leu Asn Leu Tyr Arg Ile Val
            260                 265                 270

Ile Ile Leu Arg Leu Ile Ile Leu Cys Phe Phe Phe Gln Tyr Arg Ile
        275                 280                 285

Ser His Pro Val Arg Asn Ala Tyr Gly Leu Trp Leu Val Ser Val Ile
    290                 295                 300

Cys Glu Val Trp Phe Ala Leu Ser Trp Leu Leu Asp Gln Phe Pro Lys
305                 310                 315                 320

Trp Tyr Pro Ile Asn Arg Glu Thr Tyr Leu Asp Arg Leu Ala Leu Arg
                325                 330                 335

Tyr Asp Arg Glu Gly Glu Pro Ser Gln Leu Ala Pro Ile Asp Val Phe
            340                 345                 350

Val Ser Thr Val Asp Pro Leu Lys Glu Pro Pro Leu Ile Thr Ala Asn
        355                 360                 365

Thr Val Leu Ser Ile Leu Ala Val Asp Tyr Pro Val Asp Lys Val Ser
    370                 375                 380

Cys Tyr Val Ser Asp Asp Gly Ser Ala Met Leu Thr Phe Glu Ser Leu
385                 390                 395                 400

Ser Glu Thr Ala Glu Phe Ala Arg Lys Trp Val Pro Phe Cys Lys Lys
                405                 410                 415

His Asn Ile Glu Pro Arg Ala Pro Glu Phe Tyr Phe Ala Gln Lys Ile
            420                 425                 430

Asp Tyr Leu Lys Asp Lys Ile Gln Pro Ser Phe Val Lys Glu Arg Arg
        435                 440                 445

Ala Met Lys Arg Glu Tyr Glu Glu Phe Lys Ile Arg Ile Asn Ala Leu
    450                 455                 460

Val Ala Lys Ala Gln Lys Val Pro Glu Glu Gly Trp Thr Met Ala Asp
465                 470                 475                 480

Gly Thr Ala Trp Pro Gly Asn Asn Pro Arg Asp His Pro Gly Met Ile
                485                 490                 495

Gln Val Phe Leu Gly His Ser Gly Gly Leu Asp Thr Asp Gly Asn Glu
            500                 505                 510

Leu Pro Arg Leu Val Tyr Val Ser Arg Glu Lys Arg Pro Gly Phe Gln
        515                 520                 525

His His Lys Lys Ala Gly Ala Met Asn Ala Leu Ile Arg Val Ser Ala
    530                 535                 540

Val Leu Thr Asn Gly Ala Tyr Leu Leu Asn Val Asp Cys Asp His Tyr
545                 550                 555                 560
```

```
Phe Asn Ser Ser Lys Ala Leu Arg Glu Ala Met Cys Phe Met Met Asp
                565                 570                 575

Pro Ala Leu Gly Arg Lys Thr Cys Tyr Val Gln Phe Pro Gln Arg Phe
            580                 585                 590

Asp Gly Ile Asp Leu His Asp Arg Tyr Ala Asn Arg Asn Ile Val Phe
        595                 600                 605

Phe Asp Ile Asn Met Lys Gly Leu Asp Gly Ile Gln Gly Pro Val Tyr
    610                 615                 620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Val Val Lys Ser
                645                 650                 655

Cys Cys Gly Arg Arg Lys Arg Lys Asn Lys Ser Tyr Met Asp Ser Gln
            660                 665                 670

Ser Arg Ile Met Lys Arg Thr Glu Ser Ser Ala Pro Ile Phe Asn Met
        675                 680                 685

Glu Asp Ile Glu Glu Gly Ile Glu Gly Tyr Glu Asp Glu Arg Ser Val
    690                 695                 700

Leu Met Ser Gln Arg Lys Leu Glu Lys Arg Phe Gly Gln Ser Pro Ile
705                 710                 715                 720

Phe Ile Ala Ser Thr Phe Met Thr Gln Gly Gly Ile Pro Pro Ser Thr
                725                 730                 735

Asn Pro Ala Ser Leu Leu Lys Glu Ala Ile His Val Ile Ser Cys Gly
            740                 745                 750

Tyr Glu Asp Lys Thr Glu Trp Gly Lys Glu Ile Gly Trp Ile Tyr Gly
        755                 760                 765

Ser Val Thr Glu Asp Ile Leu Thr Gly Phe Lys Met His Ala Arg Gly
    770                 775                 780

Trp Gln Ser Ile Tyr Cys Met Pro Pro Arg Pro Cys Phe Lys Gly Ser
785                 790                 795                 800

Ala Pro Ile Asn Leu Ser Asp Arg Leu Asn Gln Val Leu Arg Trp Ala
                805                 810                 815

Leu Gly Ser Val Glu Ile Leu Leu Ser Arg His Cys Pro Ile Trp Tyr
            820                 825                 830

Gly Tyr Asn Gly Arg Leu Lys Leu Leu Glu Arg Leu Ala Tyr Ile Asn
        835                 840                 845

Thr Ile Val Tyr Pro Ile Thr Ser Val Pro Leu Ile Ala Tyr Cys Val
    850                 855                 860

Leu Pro Ala Ile Cys Leu Leu Thr Asn Lys Phe Ile Ile Pro Glu Ile
865                 870                 875                 880

Ser Asn Tyr Ala Gly Met Phe Phe Ile Leu Leu Phe Ala Ser Ile Phe
                885                 890                 895

Ala Thr Gly Ile Leu Glu Leu Arg Trp Ser Gly Val Gly Ile Glu Asp
            900                 905                 910

Trp Trp Arg Asn Glu Gln Phe Trp Val Ile Gly Gly Thr Ser Ala His
        915                 920                 925

Leu Phe Ala Val Phe Gln Gly Leu Leu Lys Val Leu Ala Gly Ile Asp
    930                 935                 940

Thr Asn Phe Thr Val Thr Ser Lys Ala Ser Asp Glu Asp Gly Asp Phe
945                 950                 955                 960

Ala Glu Leu Tyr Val Phe Lys Trp Thr Ser Leu Leu Ile Pro Pro Thr
                965                 970                 975

Thr Val Leu Val Ile Asn Leu Val Gly Met Val Ala Gly Ile Ser Tyr
```

```
            980                 985                 990

Ala Ile Asn Ser Gly Tyr Gln Ser Trp Gly Pro Leu Phe Gly Lys Leu
        995                 1000                1005

Phe Phe Ser Ile Trp Val Ile Leu His Leu Tyr Pro Phe Leu Lys Gly
    1010                1015                1020

Leu Met Gly Arg Gln Asn Arg Thr Pro Thr Ile Val Ile Val Trp Ser
1025                1030                1035                1040

Ile Leu Leu Ala Ser Ile Phe Ser Leu Leu Trp Val Lys Ile Asp Pro
                1045                1050                1055

Phe Ile Ser Pro Thr Gln Lys Ala Ala Ala Leu Gly Gln Cys Gly Val
            1060                1065                1070

Asn Cys


<210> SEQ ID NO 47
<211> LENGTH: 25
<212> TYPE: DNA
<213> ORGANISM: Artificial Sequence
<220> FEATURE:
<223> OTHER INFORMATION: amplicon

<400> SEQUENCE: 47

atggcggcca acaaggggat ggtgg                                          25


<210> SEQ ID NO 48
<211> LENGTH: 25
<212> TYPE: DNA
<213> ORGANISM: Artificial Sequence
<220> FEATURE:
<223> OTHER INFORMATION: amplicon

<400> SEQUENCE: 48

tcagcagttc acaccacatt gcccc                                          25


<210> SEQ ID NO 49
<211> LENGTH: 3969
<212> TYPE: DNA
<213> ORGANISM: Zea mays

<400> SEQUENCE: 49

cttctccctc gtcggtgcgg cgtggcgcgg ctcggcgttc ggtgagaaac cactcggggg     60

atgaggatct gctgctagag tgagaggagc tacggtcagt atcctctgcc ttcgtcggcg    120

gcggaagtgg aggggaggaa gcgatggagg cgagcgccgg gctggtggcc ggctcccaca    180

accgcaacga gctcgtcgtc atccgccgcg acggcgatcc cgggccgaag ccgccgcggg    240

agcagaacgg gcaggtgtgc cagatttgcg gcgacgacgt cggccttgcc cccggcgggg    300

acccccttcgt ggcgtgcaac gagtgcgcct tccccgtctg ccgggactgc tacgaatacg    360

agcgccggga gggcacgcag aactgccccc agtgcaagac tcgatacaag cgcctcaagg    420

gctgccaacg tgtgaccggt gacgaggagg aggacggcgt cgatgacctg gacaacgagt    480

tcaactggga cggccatgac tcgcagtctg tggccgagtc catgctctac ggccacatga    540

gctacggccg tggaggtgac cctaatggcg cgccacaagc tttccagctc aaccccaatg    600

ttccactcct caccaacggg caaatggtgg atgacatccc accggagcag cacgcgctgg    660

tgccttcttt catgggtggt gggggaaaga ggatacatcc ccttccttat gcggatccca    720

gcttacctgt gcaacccagg tctatggacc catccaagga tcttgctgca tatgggtatg    780

gtagtgttgc ttggaaggaa cggatggaga attggaagca gagacaagag aggatgcacc    840

agacggggaa tgatggtggt ggtgatgatg gtgacgatgc tgatctacca ctaatggatg    900
```

```
aagcaagaca acaactgtcc aggaaaattc cacttccatc aagccagatt aatccatata    960
ggatgattat cattattcgg cttgtggttt tggggttctt cttccactac cgagtgatgc   1020
atccggtgaa tgatgcattt gctttgtggc tcatatctgt tatctgtgaa atctggtttg   1080
ccatgtcttg gattcttgat caattcccaa agtggttccc tattgagaga gagacttacc   1140
tagaccggct gtcactgagg ttcgacaagg aaggccagcc atctcaactt gctccaattg   1200
atttctttgt cagtacggtt gatcccttaa aggaacctcc tttggtcaca acaaatactg   1260
ttctatctat cctttcggtg gattatcctg ttgataaggt ttcttgctat gtttctgatg   1320
atggtgctgc aatgctaacg tttgaagcat tatctgaaac atctgaattt gcaaagaaat   1380
gggttccttt ctgcaaacgg tacaatattg aacctcgcgc tccagagtgg tacttccaac   1440
agaagataga ctacttgaaa gacaaggtgg cagcaaactt tgttagggag aggagagcaa   1500
tgaagagaga gtatgaggaa ttcaaggtga gaatcaatgc cttagttgcc aaagcccaga   1560
aagttcctga agaaggatgg acaatgcaag atggaacccc ctggcctgga aacaatgttc   1620
gtgatcatcc tggaatgatt caggtcttcc ttggccaaag cggaggcctt gactgtgagg   1680
gaaatgaact gccacgattg gtttatgttt ctagagagaa acgaccaggc tataaccatc   1740
ataagaaagc tggtgctatg aatgcattgg tccgagtctc tgctgtacta acaaatgctc   1800
catatttgtt aaacttggat tgtgatcact acatcaacaa cagcaaggct ataaaggaag   1860
caatgtgttt tatgatggac cctttactag gaaagaaggt ttgctatgta cagttccctc   1920
aaagatttga tgggattgat cgccatgacc gatatgctaa ccggaatgtt gtcttttttg   1980
atatcaacat gaaaggtttg gatggtattc agggtccaat ttatgttggt actggatgtg   2040
tatttagaag gcaggcatta tatggttatg atgcccccaa aacaaagaag ccaccatcaa   2100
ggacttgcaa ctgctggccc aagtggtgct tttgctgttg ctgctttggc aataggaagc   2160
aaaagaagac taccaaaccc aaaacagaga agaaaaagtt attatttttc aagaaagaag   2220
agaaccaatc ccctgcatat gctcttggtg aaattgacga agctgctcca ggagctgaga   2280
atgaaaaggc cggtattgta aatcaacaaa aattagaaaa gaaatttggc caatcttctg   2340
tttttgttac atccacactt ctcgagaatg gtggaacctt gaagagtgca agtcctgctt   2400
ctcttttgaa agaagctata catgtcatta gttgtggtta tgaagacaag acagactggg   2460
gaaaagagat tggctggatc tatggatcag ttacagaaga tattctaact ggtttcaaga   2520
tgcattgtca tggttggcgg tcaatttact gcatacctaa acgggttgca ttcaaaggtt   2580
ctgcacctct gaatctttca gatcgtcttc accaggtgct tcggtgggct cttgggtcta   2640
ttgagatctt cttcagcaat cattgccctc tttggtatgg gtatggtggc ggtctgaaat   2700
ttttggaaag attttcctac atcaactcca tcgtgtatcc ttggacatct attcccctct   2760
tggcttactg tacattgcct gccatctgtt tattgacagg gaaatttatc actccagagc   2820
tgaataatgt tgccagcctg tggttcatgt cactttttat ctgcattttt gctacgagca   2880
tcctagaaat gagatggagt ggtgttggaa ttgatgactg gtggaggaat gagcagttct   2940
gggtcattgg aggtgtgtcc tcacacctct ttgctgtgtt ccagggactt ctcaaggtca   3000
tagctggtgt tgatacaagc ttcaccgtga catcaaaggg tggagatgat gaggagttct   3060
cagagctata tacattcaaa tggactacct tattgatacc tcctaccacc ttgcttctat   3120
tgaacttcat tggtgtggtc gctggcgttt caaatgcgat caataacgga tatgagtcat   3180
ggggcccccct ctttgggaag ctattctttg cattttgggt gattgtccat ctttatccct   3240
ttctcaaagg tttggttgga aggcaaaaca ggacaccaac gattgtcatc gtctggtcca   3300
```

```
ttctgctggc ttcaatcttc tcgctccttt gggttcggat tgatcctttc cttgcgaagg   3360

atgatggtcc gcttcttgag gagtgtggtt tggattgcaa ctaggatgtc agtgcatcag   3420

ctcccccaat ctgcatatgc ttgaagtata ttttctggtg tttgtcccca tattcagtgt   3480

ctgtagataa gagacatgaa atgtcccaag tttcttttga tccatggtga acctacttaa   3540

tatctgagag atatactggg ggaaaatgga ggctgcggca atccttgtgc agttgggccg   3600

tggaatacag catatgcaag tgtttgattg tgcagcattc tttattactt ggtcgcaata   3660

tagatgggct gagccgaaca gcaaggtatt ttgattctgc actgctcccg tgtacaaact   3720

tggttctcaa taaggcaggc aggaatgcat ctgccagtgg aacagagcaa cctgcacatt   3780

atttatgtat gcctgttcat tggagggctt gttcattaca tgttcgtcta tactagaaaa   3840

aacagaatat tagcattaat ctatagttaa ttaaagtatg taaatgcgcc tgtttttgt    3900

tgtgtactgt aatcatctga gttggttttg tgaaaaaaaa aaaaaaaaaa aaaaaaaaaa   3960

aaaaaaaaa                                                           3969
```

```
<210> SEQ ID NO 50
<211> LENGTH: 1086
<212> TYPE: PRT
<213> ORGANISM: Zea mays

<400> SEQUENCE: 50

Met Glu Ala Ser Ala Gly Leu Val Ala Gly Ser His Asn Arg Asn Glu
1               5                   10                  15

Leu Val Val Ile Arg Arg Asp Gly Asp Pro Gly Pro Lys Pro Pro Arg
            20                  25                  30

Glu Gln Asn Gly Gln Val Cys Gln Ile Cys Gly Asp Asp Val Gly Leu
        35                  40                  45

Ala Pro Gly Gly Asp Pro Phe Val Ala Cys Asn Glu Cys Ala Phe Pro
    50                  55                  60

Val Cys Arg Asp Cys Tyr Glu Tyr Glu Arg Arg Glu Gly Thr Gln Asn
65                  70                  75                  80

Cys Pro Gln Cys Lys Thr Arg Tyr Lys Arg Leu Lys Gly Cys Gln Arg
                85                  90                  95

Val Thr Gly Asp Glu Glu Glu Asp Gly Val Asp Asp Leu Asp Asn Glu
            100                 105                 110

Phe Asn Trp Asp Gly His Asp Ser Gln Ser Val Ala Glu Ser Met Leu
        115                 120                 125

Tyr Gly His Met Ser Tyr Gly Arg Gly Gly Asp Pro Asn Gly Ala Pro
    130                 135                 140

Gln Ala Phe Gln Leu Asn Pro Asn Val Pro Leu Leu Thr Asn Gly Gln
145                 150                 155                 160

Met Val Asp Asp Ile Pro Pro Glu Gln His Ala Leu Val Pro Ser Phe
                165                 170                 175

Met Gly Gly Gly Gly Lys Arg Ile His Pro Leu Pro Tyr Ala Asp Pro
            180                 185                 190

Ser Leu Pro Val Gln Pro Arg Ser Met Asp Pro Ser Lys Asp Leu Ala
        195                 200                 205

Ala Tyr Gly Tyr Gly Ser Val Ala Trp Lys Glu Arg Met Glu Asn Trp
    210                 215                 220

Lys Gln Arg Gln Glu Arg Met His Gln Thr Gly Asn Asp Gly Gly Gly
225                 230                 235                 240

Asp Asp Gly Asp Asp Ala Asp Leu Pro Leu Met Asp Glu Ala Arg Gln
                245                 250                 255
```

```
Gln Leu Ser Arg Lys Ile Pro Leu Pro Ser Ser Gln Ile Asn Pro Tyr
            260                 265                 270

Arg Met Ile Ile Ile Ile Arg Leu Val Val Leu Gly Phe Phe Phe His
        275                 280                 285

Tyr Arg Val Met His Pro Val Asn Asp Ala Phe Ala Leu Trp Leu Ile
    290                 295                 300

Ser Val Ile Cys Glu Ile Trp Phe Ala Met Ser Trp Ile Leu Asp Gln
305                 310                 315                 320

Phe Pro Lys Trp Phe Pro Ile Glu Arg Glu Thr Tyr Leu Asp Arg Leu
                325                 330                 335

Ser Leu Arg Phe Asp Lys Glu Gly Gln Pro Ser Gln Leu Ala Pro Ile
            340                 345                 350

Asp Phe Phe Val Ser Thr Val Asp Pro Leu Lys Glu Pro Pro Leu Val
        355                 360                 365

Thr Thr Asn Thr Val Leu Ser Ile Leu Ser Val Asp Tyr Pro Val Asp
    370                 375                 380

Lys Val Ser Cys Tyr Val Ser Asp Asp Gly Ala Ala Met Leu Thr Phe
385                 390                 395                 400

Glu Ala Leu Ser Glu Thr Ser Glu Phe Ala Lys Lys Trp Val Pro Phe
                405                 410                 415

Cys Lys Arg Tyr Asn Ile Glu Pro Arg Ala Pro Glu Trp Tyr Phe Gln
            420                 425                 430

Gln Lys Ile Asp Tyr Leu Lys Asp Lys Val Ala Ala Asn Phe Val Arg
        435                 440                 445

Glu Arg Arg Ala Met Lys Arg Glu Tyr Glu Glu Phe Lys Val Arg Ile
    450                 455                 460

Asn Ala Leu Val Ala Lys Ala Gln Lys Val Pro Glu Glu Gly Trp Thr
465                 470                 475                 480

Met Gln Asp Gly Thr Pro Trp Pro Gly Asn Asn Val Arg Asp His Pro
                485                 490                 495

Gly Met Ile Gln Val Phe Leu Gly Gln Ser Gly Gly Leu Asp Cys Glu
            500                 505                 510

Gly Asn Glu Leu Pro Arg Leu Val Tyr Val Ser Arg Glu Lys Arg Pro
        515                 520                 525

Gly Tyr Asn His His Lys Lys Ala Gly Ala Met Asn Ala Leu Val Arg
    530                 535                 540

Val Ser Ala Val Leu Thr Asn Ala Pro Tyr Leu Leu Asn Leu Asp Cys
545                 550                 555                 560

Asp His Tyr Ile Asn Asn Ser Lys Ala Ile Lys Glu Ala Met Cys Phe
                565                 570                 575

Met Met Asp Pro Leu Leu Gly Lys Lys Val Cys Tyr Val Gln Phe Pro
            580                 585                 590

Gln Arg Phe Asp Gly Ile Asp Arg His Asp Arg Tyr Ala Asn Arg Asn
        595                 600                 605

Val Val Phe Phe Asp Ile Asn Met Lys Gly Leu Asp Gly Ile Gln Gly
    610                 615                 620

Pro Ile Tyr Val Gly Thr Gly Cys Val Phe Arg Arg Gln Ala Leu Tyr
625                 630                 635                 640

Gly Tyr Asp Ala Pro Lys Thr Lys Lys Pro Pro Ser Arg Thr Cys Asn
                645                 650                 655

Cys Trp Pro Lys Trp Cys Phe Cys Cys Cys Cys Phe Gly Asn Arg Lys
            660                 665                 670

Gln Lys Lys Thr Thr Lys Pro Lys Thr Glu Lys Lys Lys Leu Leu Phe
```

```
        675                 680                 685

Phe Lys Lys Glu Glu Asn Gln Ser Pro Ala Tyr Ala Leu Gly Glu Ile
    690                 695                 700

Asp Glu Ala Ala Pro Gly Ala Glu Asn Glu Lys Ala Gly Ile Val Asn
705                 710                 715                 720

Gln Gln Lys Leu Glu Lys Lys Phe Gly Gln Ser Ser Val Phe Val Thr
                725                 730                 735

Ser Thr Leu Leu Glu Asn Gly Gly Thr Leu Lys Ser Ala Ser Pro Ala
            740                 745                 750

Ser Leu Leu Lys Glu Ala Ile His Val Ile Ser Cys Gly Tyr Glu Asp
        755                 760                 765

Lys Thr Asp Trp Gly Lys Glu Ile Gly Trp Ile Tyr Gly Ser Val Thr
    770                 775                 780

Glu Asp Ile Leu Thr Gly Phe Lys Met His Cys His Gly Trp Arg Ser
785                 790                 795                 800

Ile Tyr Cys Ile Pro Lys Arg Val Ala Phe Lys Gly Ser Ala Pro Leu
                805                 810                 815

Asn Leu Ser Asp Arg Leu His Gln Val Leu Arg Trp Ala Leu Gly Ser
            820                 825                 830

Ile Glu Ile Phe Phe Ser Asn His Cys Pro Leu Trp Tyr Gly Tyr Gly
        835                 840                 845

Gly Gly Leu Lys Phe Leu Glu Arg Phe Ser Tyr Ile Asn Ser Ile Val
    850                 855                 860

Tyr Pro Trp Thr Ser Ile Pro Leu Leu Ala Tyr Cys Thr Leu Pro Ala
865                 870                 875                 880

Ile Cys Leu Leu Thr Gly Lys Phe Ile Thr Pro Glu Leu Asn Asn Val
                885                 890                 895

Ala Ser Leu Trp Phe Met Ser Leu Phe Ile Cys Ile Phe Ala Thr Ser
            900                 905                 910

Ile Leu Glu Met Arg Trp Ser Gly Val Gly Ile Asp Asp Trp Trp Arg
        915                 920                 925

Asn Glu Gln Phe Trp Val Ile Gly Gly Val Ser Ser His Leu Phe Ala
    930                 935                 940

Val Phe Gln Gly Leu Leu Lys Val Ile Ala Gly Val Asp Thr Ser Phe
945                 950                 955                 960

Thr Val Thr Ser Lys Gly Gly Asp Asp Glu Glu Phe Ser Glu Leu Tyr
                965                 970                 975

Thr Phe Lys Trp Thr Thr Leu Leu Ile Pro Pro Thr Thr Leu Leu Leu
            980                 985                 990

Leu Asn Phe Ile Gly Val Val Ala Gly Val Ser Asn Ala Ile Asn Asn
        995                 1000                1005

Gly Tyr Glu Ser Trp Gly Pro Leu Phe Gly Lys Leu Phe Phe Ala Phe
    1010                1015                1020

Trp Val Ile Val His Leu Tyr Pro Phe Leu Lys Gly Leu Val Gly Arg
1025                1030                1035                1040

Gln Asn Arg Thr Pro Thr Ile Val Ile Val Trp Ser Ile Leu Leu Ala
                1045                1050                1055

Ser Ile Phe Ser Leu Leu Trp Val Arg Ile Asp Pro Phe Leu Ala Lys
            1060                1065                1070

Asp Asp Gly Pro Leu Leu Glu Glu Cys Gly Leu Asp Cys Asn
        1075                1080                1085


<210> SEQ ID NO 51
<211> LENGTH: 25
```

```
<212> TYPE: DNA
<213> ORGANISM: Artificial Sequence
<220> FEATURE:
<223> OTHER INFORMATION: amplicon

<400> SEQUENCE: 51

atggaggcga gcgccgggct ggtgg                                        25


<210> SEQ ID NO 52
<211> LENGTH: 25
<212> TYPE: DNA
<213> ORGANISM: Artificial Sequence
<220> FEATURE:
<223> OTHER INFORMATION: amplicon

<400> SEQUENCE: 52

ctagttgcaa tccaaaccac actcc                                        25
```